United States Patent
Yuan et al.

(10) Patent No.: US 6,214,572 B1
(45) Date of Patent: Apr. 10, 2001

(54) PROGRAMMED CELL DEATH AND ICH-3

(75) Inventors: Junying Yuan, Newton; Suyue Wang, Brookline, both of MA (US); Masayuki Miura, Osaka (JP)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/908,436

(22) Filed: Aug. 7, 1997

Related U.S. Application Data

(60) Provisional application No. 60/023,937, filed on Aug. 9, 1996.

(51) Int. Cl.[7] ............... A61K 31/715; A61K 38/00; A61K 38/46; C12N 5/00

(52) U.S. Cl. ............... 435/23; 424/94.65; 435/375; 514/2; 514/12; 514/21; 514/54; 530/350

(58) Field of Search ............... 514/2, 12, 21, 514/54; 530/350; 435/375, 23; 424/94.65

(56) References Cited

PUBLICATIONS

Wang, S., et al., Identification and characterization of Ich–3, a member of the interleukin–1 beta converting enzyme (ICE)/Ced–3 family and an upstream regulator of ICE. J. Biol. Chem. 271(34):20580–20587, Aug. 23, 1996.*

Laine, VJO, et al., Lipopolysaccharide induced apoptosis of rat pancreatic acinar cells. Gut, 38:747–752, 1996.*

Allsopp, T.E. et al., "The Proto–Oncogene bcl–2 Can Selectively Rescue Neurotrophic Factor–Dependent Neurons," *Cell* 73:295–307 (1993).

Ankarcrona, M. et al., "Interleukin–1β–Induced Nitric Oxide Production Activates Apoptosis in Pancreatic RINm5F Cells," *Exp. Cell Res.* 213:172–177 (1994).

Apasov, S. et al., "Cell–mediated cytotoxicity: contact and secreted factors," *Curr. Opin. Immunol.* 5:404–410 (1993).

Barr, P.J. and L.D. Tomei, "Apoptosis and Its Role in Human Disease," *Bio/Technol.* 12:487–493 (1994).

Casciola–Rosen, L.A. et al., "Specific Cleavage of the 70–kDa Protein Component of the U1 Small Nuclear Ribonucleoprotein Is a Characteristic Biochemical Feature of Apoptotic Cell Death," *J. Biol. Chem.* 269:30757–30760 (1994).

Cerretti, D.P. et al., "Molecular Cloning of the Interleukin–1β Converting Enzyme," *Science* 256:97–100 (1992).

Cohen, J.J. and R.C. Duke, "Glucocorticoid Activation of a Calcium–Dependent Endonuclease in Thymocyte Nuclei Leads to Cell Death," *J. Immunol.* 132:38–42 (1984).

Cohen, J.J. and R.C. Duke, "Apoptosis and Programmed Cell Death in Immunity," *Annu. Rev. Immunol.* 10:267–293 (1992).

Darmon, A.J. et al., "The Cytotoxic T Cell Proteinase Granzyme B Does Not Activate Interleukin–1β–converting Enzyme," *J. Biol. Chem.* 269:32043–32046 (1994).

Darmon, A.J. et al., "Activation of the apoptotic protease CPP32 by cytotoxic T–cell–derived granzyme B," *Nature* 377:446–448 (Oct. 1995).

Dinarello, C.A., "Interleukin–1 and Interleukin–1 Antagonism," *Blood* 77:1627–1652 (1991).

Dinarello, C.A. et al., "Anticytokine Strategies in the Treatment of the Systemic Inflammatory Response Syndrome," *J. Amer. Med. Assoc.* 269:1829–1835 (1993).

Duan, H. et al., "ICE–LAP3, a Novel Mammalian Homologue of the *Caenorhabditis elegans* Cell Death Protein Ced–3 Is Activated during Fas– and Tumor Necrosis Factor–induced Apoptosis," *J. Biol. Chem.* 271:1621–1625 (Jan. 1996).

Ellis, H.M. and H.R. Horvitz, "Genetic Control of Programmed Cell Death in the Nematode *C. elegans*," *Cell* 44:817–829 (1986).

Ellis, R.E. et al., "Mechanisms and Functions of Cell Death," *Annu. Rev. Cell Biol.* 7:663–697 (1991).

Ellis, R.E. and H.R. Horvitz, "Two *C. elegans* genes control the programmed deaths of specific cells in the pharynx," *Develop.* 112:591–603 (1991).

Enari, M. et al., "Involvement of an ICE–like protease in Fas–mediated apoptosis," *Nature* 375:78–81 (May 1995).

Faucheau, C. et al., "A novel human protease similar to the interleukin–1β converting enzyme induces apoptosis in transfected cells," *EMBO J.* 14:1914–1922 (May 1995).

Fernandes–Alnemri, T. et al., "CPP32, a Novel Human Apoptotic Protein with Homology to *Caenorhabditis elegans* Cell Death Protein Ced–3 and Mammalian Interleukin–1β–converting Enzyme," *J. Biol. Chem.* 269:30761–30764 (1994).

Fernandes–Alnemri, T. et al., "Mch2, a New Member of the Apoptotic Ced–3/ICE Cysteine Protease Gene Family," *Cancer Res.* 55:2737–2742 (Jul. 1995).

Fernandes–Alnemri, T. et al., "Mch3, a Novel Human Apoptotic Cysteine Protease Highly Related to CPP32," *Cancer Res.* 55:6045–6052 (Dec. 1995).

Flaws, J.A. et al., "Interleukin–1β–Converting Enzyme–Related Proteases (IRPs) and Mammalian Cell Death: Dissociation of IRP–Induced Oligonucleosomal Endonuclease Activity from Morphological Apoptosis in Granulosa Cells of the Ovarian Follicle," *Endocrinol.* 136:5042–5053 (Nov. 1995).

(List continued on next page.)

*Primary Examiner*—David Saunders
*Assistant Examiner*—Mary Beth Tung
(74) *Attorney, Agent, or Firm*—Sterne, Kessler, Goldstein & Fox P.L.L.C.

(57) ABSTRACT

This invention relates to modulation of programmed cell death. It also relates to transgenic non-human animals comprising a disrupted Ich-3 gene and methods of making these animals. The Ich-3 mutant animals exhibit resistance to septic shock and defects in follficulogenesis. This invention also relates to methods of using the transgenic animals to screen for compounds to treat septic shock and defective folliculogenesis. Moreover, this invention also relates to methods of treating septic shock in normal individuals by inhibiting ICH-3.

12 Claims, 21 Drawing Sheets

OTHER PUBLICATIONS

Friedlander, R.M. et al., "Functional Role of Interleukin 1β (IL–1β) in IL–1β–converting Enzyme–mediated Apoptosis," *J. Exp. Med. 184*:717–724 (Aug. 1996).

Gagliardini, V. et al., "Prevention of Vertebrate Neuronal Death by the crmA Gene," *Science 263*:826–828 (1994).

Glücksmann, A., "Cell Deaths in Normal Vertebrate Ontogeny," In: *Biological Reviews of the Cambridge Philosophical Society,* Fox, H.M., ed., Cambridge at the University Press, pp. 59–86 (1951).

Haimovitz–Friedman, A. et al., "Ionizing Radiation Acts on Cellular Membranes to Generate Ceramide and Initiate Apoptosis," *J. Exp. Med. 180*:525–535 (1994).

Hazuda, D.J. et al., "Structure–Function Mapping of Interleukin 1 Precursors," *J. Biol. Chem. 266*:7081–7086 (1991).

Heusel, J.W. et al., "Cytotoxic Lymphocytes Require Granzyme B for the Rapid Induction of DNA Fragmentation and Apoptosis in Allogeneic Target Cells," *Cell 76*:977–987 (1994).

Kamens, J. et al., "Identification and Characterization of ICH–2, a Novel Member of the Interleukin–1β–converting Enzyme Family of Cysteine Proteases," *J. Biol. Chem. 270*:15250–15256 (Jun. 1995).

Karp, J.E. and S. Broder, "New Directions in Molecular Medicine," *Cancer Res. 54*:653–665 (1994).

Kuida, K. et al., "Altered Cytokine Export and Apoptosis in Mice Deficient in Interleukin–1β Converting Enzyme," *Science 267*:2000–2003 (Mar. 1995).

Kumar, S. et al., "Induction of apoptosis by the mouse Nedd2 gene, which encodes a protein similar to the product of the *Caenorhabditis elegans* cell death gene ced–3 and the mammalian IL–1β–converting enzyme," *Genes & Develop. 8*:1613–1626 (1994).

Lazebnik, Y.A. et al., "Cleavage of poly(ADP–ribose) polymerase by a proteinase with properties like ICE," *Nature 371*:346–347 (1994).

Lazebnik, Y.A. et al., "Studies of the lamin proteinase reveal multiple parallel biochemical pathways during apoptotic execution," *Proc. Natl. Acad. Sci. USA 92*:9042–9046 (Sep. 1995).

Li, P. et al., "Mice Deficient in IL–1β–Converting Enzyme Are Defective in Production of Mature IL–1β and Resistant to Endotoxic Shock," *Cell 80*:401–411 (Feb. 1995).

Li, W. et al., "Prevention of apoptosis in CNTF–dependent neurons by a mutant ICE and by viral protein CrmA but not by proto–oncogene product Bcl–2," *Cell Death & Differ. 3*:105–112 (Jan. 1996).

Lippke, J.A. et al., "Identification and Characterization of CPP32/Mch2 Homolog 1, a Novel Cysteine Protease Similar to CPP32," *J. Biol. Chem. 271*:1825–1828 (Jan. 1996).

Los, M. et al., "Requirement of an ICE/CED–3 protease for Fas/APO–1–mediated apoptosis," *Nature 375*:81–83 (May 1995).

Martin, D.P et al., "Inhibitors of Protein Synthesis and RNA Synthesis Prevent Neuronal Death Caused by Nerve Growth Factor Deprivation," *J. Cell Biol. 106*:829–844 (1988).

Masayuki, M. et al., "Apoptosis of the Neural Cells. Regulation of apoptosis by ICE/CED–3," *Adv. Neurol. Sci. 40*:Abstract (1996).

Mathias, S. et al., "Activation of the Sphingomyelin Signaling Pathway in Intact EL4 Cells and in a Cell–Free System by IL–1β," *Science 259*:519–522 (1993).

Miura, M. et al., "Induction of Apoptosis in Fibroblasts by Il–1β–Converting Enzyme, a Mammalian Homology of the *C. elegans* Cell Death Gene ced–3," *Cell 75*:653–660 (1993).

Miura, M. et al., "Tumor necrosis factor–induced apoptosis is mediated by a Crm–A–sensitive cell death pathway," *Proc. Natl. Acad. Sci. USA 92*:8318–8322 (Aug. 1995).

Morrison, D.C. and J.L. Ryan, "Endotoxins and Disease Mechanisms," *Ann. Rev. Med. 38*:417–432 (1987).

Munday, N.A. et al., "Molecular Cloning and Pro–apoptotic Activity of $ICE_{rel}II$ and $ICE_{rel}III$, Members of the ICE/CED–3 Family of Cysteine Proteases," *J. Biol. Chem 270*:15870–15876 (Jun. 1995).

Nicholson, D.W. et al., "Identification and inhibition of the ICE/CED–3 protease necessary for mammalian apoptosis," *Nature 376*:37–43 (Jul. 1995).

Perregaux, D. and C.A. Gabel, "Interleukin–1β Maturation and Relase in Response to ATP and Nigericin," *J. Biol. Chem. 269*:15195–15203 (1994).

Raingeaud, J. et al., "Pro–inflammatory Cytokines and Environmental Stress Cause p38 Mitogen–activated Protein Kinase Activation by Dual Phosphorylation on Tyrosine and Threonine," *J. Biol. Chem. 270*:7420–7426 (Mar. 1995).

Ratts, V.S. et al., "Ablation of bcl–2 Gene Expression Decreases the Numbers of Oocytes and Primordial Follicles Established in the Post–Natal Female Mouse Gonad," *Endocrinol. 136*:3665–3668 (Aug. 1995).

Ray, C.A. et al., "Viral Inhibition of Inflammation: Cowpox Virus Encodes an Inhibitor of the Interleukin–1β Converting Enzyme," *Cell 69*:597–604 (1992).

Sarin, A. et al., "Protease Inhibitors Selectively Block T Cell Receptor–triggered Programmed Cell Death in a Murine T Cell Hybridoma and Activated Peripheral T Cells," *J. Exp. Med. 178*:1693–1700 (1993).

Shi, L. et al., "A Natural Killer Cell Granule Protein That Induces DNA Fragmentation and Apoptosis," *J. Exp. Med. 175*:553–566 (1992).

Shi, L. et al., "Purification of Three Cytotoxic Lymphocyte Granule Serine Proteases That Induce Apoptosis through Distinct Substrate and Target Cell Interactions," *J. Exp. Med. 176*:1521–1529 (1992).

Shi, L. et al., "Activation of an interleukin 1 converting enzyme–dependent apoptosis pathway by granzyme B," *Proc. Natl. Acad. Sci. USA 93*:11002–11007 (Oct. 1996).

Shimizu, S. et al., "Prevention of hypoxia–induced cell death by Bcl–2 and Bcl–xL," *Nature 374*:811–813 (Apr. 1995).

Stanisic, T. et al., "Partial Inhibition of Castration Induced Vental Prostate Regression with Actinomycin D and Cycloheximide," *Invest. Urology 16*:19–22 (1978).

Suda, T. et al., "Molecular Cloning and Expression of the Fas Ligand, a Novel Member of the Tumor Necrosis Factor Family," *Cell 75*:1169–1178 (1993).

Talley, A.K. et al., "Tumor Necrosis Factor Alpha–Induced Apoptosis in Human Neuronal Cells: Protection by the Antioxidant N–Acetylcysteine and the Genes bcl–2 and crmA," *Mol. Cell. Biol. 15*:2359–2366 (May 1995).

Tamura, T. et al., "An IRF–1–dependent pathway of DNA damage–induced apoptosis in mitogen–activated T lymphocytes," *Nature 376*:596–599 (Aug. 1995).

Tewari, M. et al., "Fas– and Tumor Necrosis Factor–induced Apoptosis Is Inhibited by the Poxvirus crmA Gene Product," *J. Biol. Chem. 270*:3255–3260 (Feb. 1995).

Tewari, M. et al., "Yama/CPP32β, a Mammalian Homolog of CED-3, Is a Crm-A-Inhibitable Protease That Cleaves the Death Substrate Poly(ADP-Ribose) Polymerase," *Cell* 81:801-809 (Junl 1995).

Tewari, M. et al., "CrmA, a Poxvirus-encoded Serpin, Inhibits Cytotoxic T-lymphocyte-mediated Apoptosis," *J. Biol. Chem.* 270:22705-22708 (Sep. 1995).

Thornberry, N.A. et al., "A novel heterodimeric cysteine protease is required for interleukin-1β processing in monocytes," *Nature* 356:768-774 (1992).

Tilly, J.L., "The Molecular Basis of Ovarian Cell Death During Germ Cell Attrition, Follicular Atresia, and Luteolysis," *Frontiers in Biosci.* 1:d1-d11 (Jan. 1996).

Vaux, D.L. et al., "An Evolutionary Perspective on Apoptosis," *Cell* 76:777-779 (1994).

Walker, N.P.C. et al., "Crystal Structure of the Cysteine Protease Interleukin-1β-Converting Enzyme: A $(p20/p10)_2$ Homodimer," *Cell* 78:343-352 (1994).

Wang, L. et al., "Ich-1, and ICE/ced-3-Related Gene, Encodes Both Positive and Negative Regulators of Programmed Cell Death," *Cell* 78:739-750 (1994).

Wang, S. et al., "Identification and Characterization of Ich-3, a Member of the Interleukin-1β Converting Enzyme (ICE)/Ced-3 Family and an Upstream Regulator of ICE," *J. Biol. Chem.* 271:20580-20587 (Aug. 1996).

Wilson, K.P. et al., "Structure and mechanism of interleukin-1β converting enzyme," *Nature* 370:270-275 (1994).

Wyllie, A.H. et al., "Cell Death: The Significance of Apoptosis," *Intl. Rev. Cytology* 68:251-306 (1980).

Wyllie, A.H., "Cell death: a new classification separating apoptosis from necrosis," In: *Cell death in biology and pathology,* Bowen, I.D., and Lockshin, R.A., eds., Chapman and Hall Ltd., New York, NY, pp. 9-34 (1981).

Xia, Z. et al., "Opposing Effects of ERK and JNK-p38 MAP Kinases on Apoptosis," *Science* 270:1326-1331 (Nov. 1995).

Yonehara, S. et al., "A Cell-Killing Monoclonal Antibody (Anti-Fas) to a Cell Surface Antigen Co-Downregulated with the Receptor of Tumor Necrosis Factor," *J. Exp. Med.* 169:1747-1756 (1989).

Yuan, J. and H.R. Horvitz, "The *Caenorhabditis elegans* Genes ced-3 and ced-4 Act Cell Autonomously to Cause Programmed Cell Death," *Develop. Biol.* 138:33-41 (1990).

Yuan, J. et al., "The *C. elegans* Cell Death Gene ced-3 Encodes a Protein Similar to Mammalian Interleukin-1β-Converting Enzyme," *Cell* 75:641-652 (1993).

Yuan, J., "Molecular control of life and death," *Curr. Opin. Cell Biol.* 7:211-214 (Apr. 1995).

Yuan, J., "Evolutionary Conservation of a Genetic Pathway of Programmed Cell Death," *J. Cell. Biochem.* 60:4-11 (Jan. 1996).

International Search Report for International Application No. PCT/US97/13898.

* cited by examiner

```
  1 TCTTCACAGTGCGAAAGAACTGAGGCTTTTTCTCATGGCTGAAAACAAACACCCTGACAA   60
  1                                        M  A  E  N  K  H  P  D  K    9

61 ACCACTTAAGGTGTTGGAACAGCTGGGCAAAGAAGTCCTTACGGAGTACCTAGAAAAATT  120
 10  P  L  K  V  L  E  Q  L  G  K  E  V  L  T  E  Y  L  E  K  L    29

121 AGTACAAAGCAATGTACTGAAATTAAAGGAGGAAGATAAACAAAAATTTAACAATGCTGA  180
 30  V  Q  S  N  V  L  K  L  K  E  E  D  K  Q  K  F  N  N  A  E    49

181 ACGCAGTGACAAGCGTTGGGTTTTTGTAGATGCCATGAAAAAGAAACACAGCAAAGTAGG  240
 50  R  S  D  K  R  W  V  F  V  D  A  M  K  K  K  H  S  K  V  G    69
                                 (↑ p20)

241 TGAAATGCTTCTCCAGACATTCTTCAGTGTGGACCCAGGCAGCCACCATGGTGAAGCTAA  300
 70  E  M  L  L  Q  T  F  F  S  V  D  P  G  S  H  H  G  E  A  N    89
                                  (↑ p20)

301 TCTGGAAATGGAGGAACCAGAAGAATCATTGAACACTCTCAAGCTTTGTTCCCCTGAAGA  360
 90  L  E  M  E  E  P  E  E  S  L  N  T  L  K  L  C  S  P  E  E   109

361 GTTCACAAGGCTTTGCAGAGAAAAGACACAAGAAATTTACCCAATAAAGGAGGCCAATGG  420
110  F  T  R  L  C  R  E  K  T  Q  E  I  Y  P  I  K  E  A  N  G   129

421 CCGTACACGAAAGGCTCTTATCATATGCAATACAGAGTTCAAACATCTCTCACTGAGGTA  480
130  R  T  R  K  A  L  I  I  C  N  T  E  F  K  H  L  S  L  R  Y   149

481 TGGGGCTAAATTTGACATCATTGGTATGAAAGGCCTTCTTGAAGACTTAGGCTACGATGT  540
150  G  A  K  F  D  I  I  G  M  K  G  L  L  E  D  L  G  Y  D  V   169

541 GGTGGTGAAAGAGGAGCTTACAGCAGAGGGCATGGAGTCAGAGATGAAAGACTTTGCTGC  600
170  V  V  K  E  E  L  T  A  E  G  M  E  S  E  M  K  D  F  A  A   289

601 ACTCTCAGAACACCAGACATCAGACAGCACATTCCTGGTGCTAATGTCTCATGGCACACT  660
190  L  S  E  H  Q  T  S  D  S  T  F  L  V  L  M  S  H  G  T  L   209
```

FIG.1A

| | | |
|---|---|---|
| 661 | GCATGGCATTTGTGGAACAATGCACAGTGAAAAAACTCCAGATGTGCTACAGTATGATAC | 720 |
| 210 | H  G  I  C  G  T  M  H  S  E  K  T  P  D  V  L  Q  Y  D  T | 229 |

| | | |
|---|---|---|
| 721 | CATCTATCAGATATTCAACAATTGCCACTGTCCAGGTCTACGAGACAAACCCAAAGTCAT | 780 |
| 230 | I  Y  Q  I  F  N  N  C  H  C  P  G  L  R  D  K  P  K  V  I | 249 |

| | | |
|---|---|---|
| 781 | CATTGTGCAGGCCTGCAGAGGTGGGAACTCTGGAGAAATGTGGATCAGAGAGTCTTCAAA | 840 |
| 250 | I  V  Q  A  C  R  G  G  N  S  G  E  M  W  I  R  E  S  S  K | 269 |

| | | |
|---|---|---|
| 841 | ACCCCAGTTGTGCAGAGGTGTAGATCTACCTAGGAATATGGAAGCTGATGCTGTCAAGCT | 900 |
| 270 | P  Q  L  C  R  G  V  D  L  P  R  N  M  E  A  D  A  V  K  L | 289 |
| | | ↑ p10 |

| | | |
|---|---|---|
| 901 | GAGCCACGTGGAGAAGGACTTCATTGCCTTCTACTCTACAACCCCACATCACTTGTCCTA | 960 |
| 390 | S  H  V  E  K  D  F  I  A  F  Y  S  T  T  P  H  H  L  S  Y | 309 |

| | | |
|---|---|---|
| 961 | CCGAGACAAAACAGGAGGCTCTTACTTCATCACTAGACTCATTTCCTGCTTCCGGAAACA | 1020 |
| 310 | R  D  K  T  G  G  S  Y  F  I  T  R  L  I  S  C  F  R  K  H | 329 |

| | | |
|---|---|---|
| 1021 | TGCTTGCTCTTGTCATCTCTTTGATATATTCCTGAAGGTGCAACAATCATTTGAAAAGGC | 1080 |
| 330 | A  C  S  H  L  F  D  I  F  L  K  V  Q  Q  S  F  E  K  A | 349 |

| | | |
|---|---|---|
| 1081 | AAGTATTCATTCCCAGATGCCCACCATTGATCGGGCAACCTTGACAAGATATTTCTACCT | 1140 |
| 350 | S  I  H  S  Q  M  P  T  I  D  R  A  T  L  T  R  Y  F  Y  L | 369 |

| | | |
|---|---|---|
| 1141 | CTTTCCTGGCAACTGAGAACAAAGCAACAAGCAACTGAATCTCATTTCTTCAGCTTGAAG | 1200 |
| 370 | F  P  G  N  * | 373 |

| | | |
|---|---|---|
| 1201 | AAGTGATCTTGGCCAAGGATCACATTCTATTCCTGAAATTCCAGAACTAGTGAAATTAAG | 1260 |

| | | |
|---|---|---|
| 1261 | GAAAGAATACTTATGAATTCAAGACCAGCCTAAGCAACACAGTGGGATTCTGTTCCATAG | 1320 |

| | | |
|---|---|---|
| 1321 | ACAAGCAAACAAGCAAAAATAAAAAAAAAA | 1350 |

FIG.1B

```
ICH-3      ..........  ..........  ..........  ..........  ..MAENKHPD    8
hICE       ..........  ..........  ..........  ..........  ..MADKVLKE    8
mICE       ..........  ..........  ..........  ..........  ..MADKILRA    8
TX         ..........  ..........  ..........  ..........  ..MAEGNHRK    8
ICErelIII  MFKGILQSGL  DNFVINHMLK  NNVAGQTSIQ  TLVPNTDQKS  TSVKKDNHKK   50

ICH-3      KPLKMLEQLG  KEVLTEYLEK  LVQSNVLKLK  EEDKQKFNNA  ERSDKRWVFV   58
hICE       KRKLFIRSMG  EGTINGLLDE  LLQTRVLNKE  EMEKVKRENA  TVMDKTRALI   58
mICE       KRKQFINSVS  IGTINGLLDE  LLEKRVLNQE  EMDKIKLANI  TAMDKARNLC   58
TX         KPLKMLESLG  KDFLTGVLDN  LVEQNVLNWK  EEEKKKYYDA  KTEDKVRAMA   58
ICErelIII  KTVKMLEYLG  KDVLHGVFNY  LAKHDVLTLK  EEEKKKYYDA  KIEDKALILV  100

ICH-3      DAMKKKHSKV  GEMLL.....  ..........  .......QTF  FSVDPG....   82
hICE       DSVIPKGAQA  CQICITYICE  EDSYLAGTLG  LSADQTSGNY  LNMQDSQGVL  108
mICE       DHVSKKGAPA  SQIFITYICN  EDCYLAGILE  LQSAPSAETF  VATEDSKGGH  108
TX         DSMQEKQRMA  GQMLL.....  ..........  .......QTF  FNIDQI....   82
ICErelIII  DSLR.KNRVA  HQMFT.....  ..........  .......QTL  LNMDQK....  123
                                                              (p24)

HindIV
ICH-3      .SHHGEANLE  ME....EPEE  SLNTLKLCSP  EEFTRLQREK  TQEIYPIKEA  127
hICE       SSFPAPQAVQ  DNPAMPTSSG  SEGNVKLCSL  EEAQRIWKQK  SAEIYPIMDK  158
mICE       PSSSETKE.E  QNKEDGTFPG  LTGTLKFCPL  EKAQKLWKEN  PSEIYPIMNT  157
TX         .SPNKKAHPN  MEAGPPESGE  STDALKLCPH  EEFLRLCKER  AEEIYPIKER  131
ICErelIII  .ITSVKPLLQ  IDAGPPESAE  STNILKLCPR  EEFLRLCKKN  HDEIYPIKKR  172
                 p20
                            ^
ICH-3      NGRTRKALTI  CNTEFKHLSL  RYGAKFDIIG  MKG..LLEDL  GYDVVKEEL  175
hICE       SSRTRLALII  CNEEFDSIPR  RTGAEVDITG  MT..MLLQNL  GYSVDVKKNL  206
mICE       TTRTRLALII  CNTEFQHLSP  RVGAQVDLRE  MK..LLLEDL  GYTMKVKENL  205
TX         NNRTRLALII  CNTEFDHLPP  RNGADFDITG  MKELLLLEGL  DYSVDVEENL  181
ICErelIII  EDRRRLALII  CNTKFDHLPA  RNGAHYDIVG  MKR..LLQGL  GYTMVDEKNL  220

**
ICH-3      TAEGMESEMK  DFAALSEHQT  SDSTFLVLMS  HGILHGICGT  MHSEKTPDVL  225
hICE       TASDMTTELE  AFAHRPEHKT  SDSTFLVFMS  HGIREGICGK  KHSEQVPDIL  256
mICE       TALEMVKEVK  EFAACPEHKT  SDSTFLVFMS  HGIQEGICGT  TYSNEVSDIL  255
TX         TARDMESALR  AFATRPEHKS  SDSTFLVLMS  HGILEGICGV  VHDEKKPDVL  231
ICErelIII  TARDMESVLR  AFAARPEHKS  SDSTFLVLMS  HGILEGICGT  AHKKKKPDVL  270
                                       ^  *
ICH-3      QYDTIYQIFN  NCHCPGLRDK  PKVITVQACR  GGNSGEMWIR  ESSKPQLCRG  275
hICE       QLNAIFNMLN  TKNCPSLKDK  PKVIIIQACR  GDSPGVVWFK  DSVGVSGNLS  306
mICE       KVDTIFQMMN  TLKCPSLKDK  PKVIIIQACR  GEKQGVVLLK  DSVRDSEE.D  304
TX         LYDTIFQIFN  NRNCLSLKDK  PKVIIVQACR  GANRGELWVR  DSPASLEVAS  281
ICErelIII  LYDTIFQIFN  NRNCLSLKDK  PKVIIVQACR  GEKHGELWVR  DSPASLAVIS  320
                                                p20
                          ^ ^                  ^
ICH-3      VDLPRNMEAD  AVKLSHMEKD  FIAFYSITPH  HLSYRDKTGG  SYFITRLTSC  325
hICE       LPTTEEFEDD  AIKKAHIEKD  FIAFCSSTPD  NVSWRHPTMG  SVFIGRLIEH  356
mICE       FLTDAIFEDD  GIKKAHIEKD  FIAFCSSTPD  NVSWRHPVRG  SLFIESLIKH  354
TX         SQSSENLEED  AVYKTHVEKD  FIAFCSSTPH  NVSWRDSTMG  SIFITQLITC  331
ICErelIII  SQSSENLEAD  SVCKIHFEKD  FIAFCSSSPH  NVSWRDRTRG  SIFITELITC  370
               p10                    ^^
ICH-3      FRKHACSCHL  FDIFLKVQQS  FEKASIHSQM  PTIDRATLTR  YFYLFPGN*   373
hICE       MQEYACSCDV  EEIFRKVRFS  FEQPDGRAQM  PTTERVTLTR  CFYLFPGH    404
mICE       MKEYAWSCDL  EDIFRKVRFS  FEQPEFRLQM  PTADRVTLTK  RFYLFPGH    402
TX         FQKYSWCCHL  EEMFRKVQQS  FETPRAKAQM  PTIERLSMTR  YFYLFPGN*   379
ICErelIII  FQKYSCCCHL  MEIFRKVQKS  FEVPQAKAQM  PTIERATLTR  DFYLFPGN*   377
```

FIG.2A

Granzyme B cleavage of ICH-3 proteins

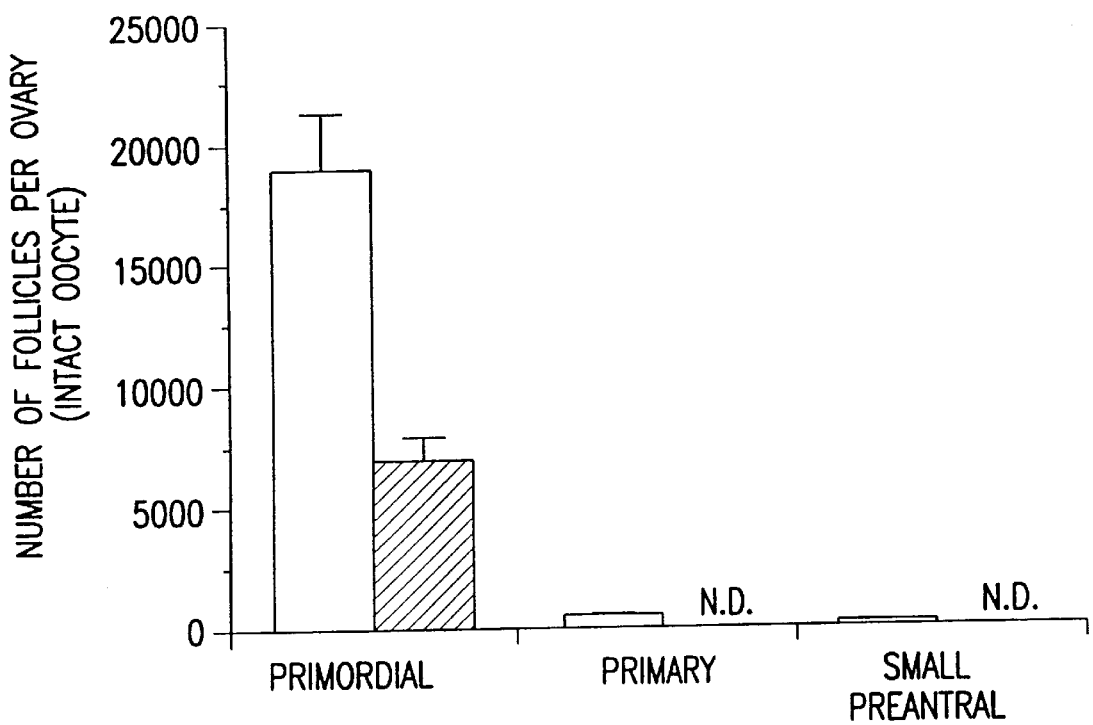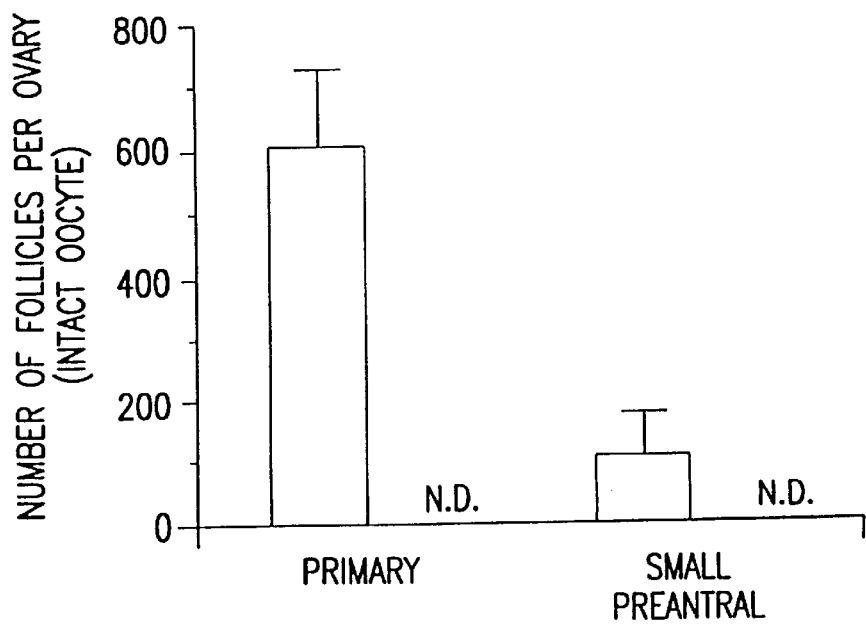
FIG.13A

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 35..1153

(xi) SEQUENCE DESCRIPTION: SEQ ID NO:1:

```
TCTTCACAGT GCGAAAGAAC TGAGGCTTTT TCTC ATG GCT GAA AAC AAA CAC          52
                                     Met Ala Glu Asn Lys His
                                      1               5

CCT GAC AAA CCA CTT AAG GTG TTG GAA CAG CTG GGC AAA GAA GTC CTT       100
Pro Asp Lys Pro Leu Lys Val Leu Glu Gln Leu Gly Lys Glu Val Leu
             10                  15                  20

ACG GAG TAC CTA GAA AAA TTA GTA CAA AGC AAT GTA CTG AAA TTA AAG       148
Thr Glu Tyr Leu Glu Lys Leu Val Gln Ser Asn Val Leu Lys Leu Lys
         25                  30                  35

GAG GAA GAT AAA CAA AAA TTT AAC AAT GCT GAA CGC AGT GAC AAG CGT       196
Glu Glu Asp Lys Gln Lys Phe Asn Asn Ala Glu Arg Ser Asp Lys Arg
     40                  45                  50

TGG GTT TTT GTA GAT GCC ATG AAA AAG AAA CAC AGC AAA GTA GGT GAA       244
Trp Val Phe Val Asp Ala Met Lys Lys Lys His Ser Lys Val Gly Glu
 55                  60                  65                  70

ATG CTT CTC CAG ACA TTC TTC AGT GTG GAC CCA GGC AGC CAC CAT GGT       292
Met Leu Leu Gln Thr Phe Phe Ser Val Asp Pro Gly Ser His His Gly
                 75                  80                  85

GAA GCT AAT CTG GAA ATG GAG GAA CCA GAA GAA TCA TTG AAC ACT CTC       340
Glu Ala Asn Leu Glu Met Glu Glu Pro Glu Glu Ser Leu Asn Thr Leu
             90                  95                 100

AAG CTT TGT TCC CCT GAA GAG TTC ACA AGG CTT TGC AGA GAA AAG ACA       388
Lys Leu Cys Ser Pro Glu Glu Phe Thr Arg Leu Cys Arg Glu Lys Thr
        105                 110                 115

CAA GAA ATT TAC CCA ATA AAG GAG GCC AAT GGC CGT ACA CGA AAG GCT       436
Gln Glu Ile Tyr Pro Ile Lys Glu Ala Asn Gly Arg Thr Arg Lys Ala
    120                 125                 130

CTT ATC ATA TGC AAT ACA GAG TTC AAA CAT CTC TCA CTG AGG TAT GGG       484
Leu Ile Ile Cys Asn Thr Glu Phe Lys His Leu Ser Leu Arg Tyr Gly
135                 140                 145                 150

GCT AAA TTT GAC ATC ATT GGT ATG AAA GGC CTT CTT GAA GAC TTA GGC       532
Ala Lys Phe Asp Ile Ile Gly Met Lys Gly Leu Leu Glu Asp Leu Gly
```

```
                155                 160                 165
TAC GAT GTG GTG GTG AAA GAG GAG CTT ACA GCA GAG GGC ATG GAG TCA           580
Tyr Asp Val Val Val Lys Glu Glu Leu Thr Ala Glu Gly Met Glu Ser
            170                 175                 180

GAG ATG AAA GAC TTT GCT GCA CTC TCA GAA CAC CAG ACA TCA GAC AGC           628
Glu Met Lys Asp Phe Ala Ala Leu Ser Glu His Gln Thr Ser Asp Ser
            185                 190                 195

ACA TTC CTG GTG CTA ATG TCT CAT GGC ACA CTG CAT GGC ATT TGT GGA           676
Thr Phe Leu Val Leu Met Ser His Gly Thr Leu His Gly Ile Cys Gly
    200                 205                 210

ACA ATG CAC AGT GAA AAA ACT CCA GAT GTG CTA CAG TAT GAT ACC ATC           724
Thr Met His Ser Glu Lys Thr Pro Asp Val Leu Gln Tyr Asp Thr Ile
215                 220                 225                 230

TAT CAG ATA TTC AAC AAT TGC CAC TGT CCA GGT CTA CGA GAC AAA CCC           772
Tyr Gln Ile Phe Asn Asn Cys His Cys Pro Gly Leu Arg Asp Lys Pro
                235                 240                 245

AAA GTC ATC ATT GTG CAG GCC TGC AGA GGT GGG AAC TCT GGA GAA ATG           820
Lys Val Ile Ile Val Gln Ala Cys Arg Gly Gly Asn Ser Gly Glu Met
            250                 255                 260

TGG ATC AGA GAG TCT TCA AAA CCC CAG TTG TGC AGA GGT GTA GAT CTA           868
Trp Ile Arg Glu Ser Ser Lys Pro Gln Leu Cys Arg Gly Val Asp Leu
            265                 270                 275

CCT AGG AAT ATG GAA GCT GAT GCT GTC AAG CTG AGC CAC GTG GAG AAG           916
Pro Arg Asn Met Glu Ala Asp Ala Val Lys Leu Ser His Val Glu Lys
    280                 285                 290

GAC TTC ATT GCC TTC TAC TCT ACA ACC CCA CAT CAC TTG TCC TAC CGA           964
Asp Phe Ile Ala Phe Tyr Ser Thr Thr Pro His His Leu Ser Tyr Arg
295                 300                 305                 310

GAC AAA ACA GGA GGC TCT TAC TTC ATC ACT AGA CTC ATT TCC TGC TTC          1012
Asp Lys Thr Gly Gly Ser Tyr Phe Ile Thr Arg Leu Ile Ser Cys Phe
                315                 320                 325

CGG AAA CAT GCT TGC TCT TGT CAT CTC TTT GAT ATA TTC CTG AAG GTG          1060
Arg Lys His Ala Cys Ser Cys His Leu Phe Asp Ile Phe Leu Lys Val
            330                 335                 340

CAA CAA TCA TTT GAA AAG GCA AGT ATT CAT TCC CAG ATG CCC ACC ATT          1108
Gln Gln Ser Phe Glu Lys Ala Ser Ile His Ser Gln Met Pro Thr Ile
            345                 350                 355

GAT CGG GCA ACC TTG ACA AGA TAT TTC TAC CTC TTT CCT GGC AAC              1153
Asp Arg Ala Thr Leu Thr Arg Tyr Phe Tyr Leu Phe Pro Gly Asn
    360                 365                 370

TGAGAACAAA GCAACAAGCA ACTGAATCTC ATTTCTTCAG CTTGAAGAAG TGATCTTGGC        1213

CAAGGATCAC ATTCTATTCC TGAAATTCCA GAACTAGTGA AATTAAGGAA AGAATACTTA        1273

TGAATTCAAG ACCAGCCTAA GCAACACAGT GGGATTCTGT TCCATAGACA AGCAAACAAG        1333

CAAAAATAAA AAAAAA                                                       1350

(2) INFORMATION FOR SEQ ID NO:2:

(i) SEQUENCE CHARACTERISTICS:
        (A) LENGTH: 373 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Glu Asn Lys His Pro Asp Lys Pro Leu Lys Val Leu Glu Gln
 1               5                  10                  15

Leu Gly Lys Glu Val Leu Thr Glu Tyr Leu Glu Lys Leu Val Gln Ser
            20                  25                  30
```

-continued

```
Asn Val Leu Lys Leu Lys Glu Glu Asp Lys Gln Lys Phe Asn Asn Ala
         35                  40                  45
Glu Arg Ser Asp Lys Arg Trp Val Phe Val Asp Ala Met Lys Lys Lys
 50                  55                  60
His Ser Lys Val Gly Glu Met Leu Leu Gln Thr Phe Phe Ser Val Asp
 65                  70                  75                  80
Pro Gly Ser His His Gly Glu Ala Asn Leu Glu Met Glu Glu Pro Glu
                 85                  90                  95
Glu Ser Leu Asn Thr Leu Lys Leu Cys Ser Pro Glu Glu Phe Thr Arg
                100                 105                 110
Leu Cys Arg Glu Lys Thr Gln Glu Ile Tyr Pro Ile Lys Glu Ala Asn
            115                 120                 125
Gly Arg Thr Arg Lys Ala Leu Ile Ile Cys Asn Thr Glu Phe Lys His
130                 135                 140
Leu Ser Leu Arg Tyr Gly Ala Lys Phe Asp Ile Ile Gly Met Lys Gly
145                 150                 155                 160
Leu Leu Glu Asp Leu Gly Tyr Asp Val Val Val Lys Glu Glu Leu Thr
                165                 170                 175
Ala Glu Gly Met Glu Ser Glu Met Lys Asp Phe Ala Ala Leu Ser Glu
            180                 185                 190
His Gln Thr Ser Asp Ser Thr Phe Leu Val Leu Met Ser His Gly Thr
        195                 200                 205
Leu His Gly Ile Cys Gly Thr Met His Ser Glu Lys Thr Pro Asp Val
210                 215                 220
Leu Gln Tyr Asp Thr Ile Tyr Gln Ile Phe Asn Asn Cys His Cys Pro
225                 230                 235                 240
Gly Leu Arg Asp Lys Pro Lys Val Ile Val Gln Ala Cys Arg Gly
                245                 250                 255
Gly Asn Ser Gly Glu Met Trp Ile Arg Glu Ser Ser Lys Pro Gln Leu
            260                 265                 270
Cys Arg Gly Val Asp Leu Pro Arg Asn Met Glu Ala Asp Ala Val Lys
        275                 280                 285
Leu Ser His Val Glu Lys Asp Phe Ile Ala Phe Tyr Ser Thr Thr Pro
290                 295                 300
His His Leu Ser Tyr Arg Asp Lys Thr Gly Gly Ser Tyr Phe Ile Thr
305                 310                 315                 320
Arg Leu Ile Ser Cys Phe Arg Lys His Ala Cys Ser Cys His Leu Phe
                325                 330                 335
Asp Ile Phe Leu Lys Val Gln Gln Ser Phe Glu Lys Ala Ser Ile His
            340                 345                 350
Ser Gln Met Pro Thr Ile Asp Arg Ala Thr Leu Thr Arg Tyr Phe Tyr
        355                 360                 365
Leu Phe Pro Gly Asn
370
```

(2) INFORMATION FOR SEQ ID NO:3:

(i) SEQUENCE CHARACTERISTICS:
        (A) LENGTH: 404 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:3:

-continued

```
Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
            35                  40                  45

Thr Val Met Asp Lys Thr Arg Ala Leu Ile Asp Ser Val Ile Pro Lys
            50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
                100                 105                 110

Ala Pro Gln Ala Val Gln Asp Asn Pro Ala Met Pro Thr Ser Ser Gly
                115                 120                 125

Ser Glu Gly Asn Val Lys Leu Cys Ser Leu Glu Glu Ala Gln Arg Ile
                130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
                180                 185                 190

Leu Gln Asn Leu Gly Tyr Ser Val Asp Val Lys Lys Asn Leu Thr Ala
                195                 200                 205

Ser Asp Met Thr Thr Glu Leu Glu Ala Phe Ala His Arg Pro Glu His
210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
                260                 265                 270

Leu Lys Asp Lys Pro Lys Val Ile Ile Gln Ala Cys Arg Gly Asp
                275                 280                 285

Ser Pro Gly Val Val Trp Phe Lys Asp Ser Val Gly Val Ser Gly Asn
                290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
                340                 345                 350

Leu Ile Glu His Met Gln Glu Tyr Ala Cys Ser Cys Asp Val Glu Glu
                355                 360                 365

Ile Phe Arg Lys Val Arg Phe Ser Phe Glu Gln Pro Asp Gly Arg Ala
                370                 375                 380

Gln Met Pro Thr Thr Glu Arg Val Thr Leu Thr Arg Cys Phe Tyr Leu
385                 390                 395                 400

Phe Pro Gly His
```

(2) INFORMATION FOR SEQ ID NO:4:

(i) SEQUENCE CHARACTERISTICS:
        (A) LENGTH: 402 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:4:

```
Met Ala Asp Lys Ile Leu Arg Ala Lys Arg Lys Gln Phe Ile Asn Ser
1               5                  10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asn Leu Cys Asp His Val Ser Lys Lys
    50                  55                  60

Gly Ala Pro Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
            85                  90                  95

Thr Phe Val Ala Thr Glu Asp Ser Lys Gly His Pro Ser Ser Ser
        100                 105                 110

Glu Thr Lys Glu Glu Gln Asn Lys Glu Asp Gly Thr Phe Pro Gly Leu
    115                 120                 125

Thr Gly Thr Leu Lys Phe Cys Pro Leu Glu Lys Ala Gln Lys Leu Trp
130                 135                 140

Lys Glu Asn Pro Ser Glu Ile Tyr Pro Ile Met Asn Thr Thr Thr Arg
145                 150                 155                 160

Thr Arg Leu Ala Leu Ile Ile Cys Asn Thr Glu Phe Gln His Leu Ser
            165                 170                 175

Pro Arg Val Gly Ala Gln Val Asp Leu Arg Glu Met Lys Leu Leu Leu
        180                 185                 190

Glu Asp Leu Gly Tyr Thr Val Lys Val Lys Glu Asn Leu Thr Ala Leu
    195                 200                 205

Glu Met Val Lys Glu Val Lys Glu Phe Ala Ala Cys Pro Glu His Lys
210                 215                 220

Thr Ser Asp Ser Thr Phe Leu Val Phe Met Ser His Gly Ile Gln Glu
225                 230                 235                 240

Gly Ile Cys Gly Thr Thr Tyr Ser Asn Glu Val Ser Asp Ile Leu Lys
            245                 250                 255

Val Asp Thr Ile Phe Gln Met Met Asn Thr Leu Lys Cys Pro Ser Leu
        260                 265                 270

Lys Asp Lys Pro Lys Val Ile Ile Gln Ala Cys Arg Gly Glu Lys
    275                 280                 285

Gln Gly Val Val Leu Lys Asp Ser Val Arg Asp Ser Glu Glu Asp
290                 295                 300

Phe Leu Thr Asp Ala Ile Phe Glu Asp Asp Gly Ile Lys Lys Ala His
305                 310                 315                 320

Ile Glu Lys Asp Phe Ile Ala Phe Cys Ser Ser Thr Pro Asp Asn Val
            325                 330                 335

Ser Trp Arg His Pro Val Arg Gly Ser Leu Phe Ile Glu Ser Leu Ile
        340                 345                 350

Lys His Met Lys Glu Tyr Ala Trp Ser Cys Asp Leu Glu Asp Ile Phe
```

```
                355                 360                 365
Arg Lys Val Arg Phe Ser Phe Glu Gln Pro Glu Phe Arg Leu Gln Met
            370                 375                 380
Pro Thr Ala Asp Arg Val Thr Leu Thr Lys Arg Phe Tyr Leu Phe Pro
385                 390                 395                 400
Gly His (2) INFORMATION FOR SEQ ID NO:5:

(i) SEQUENCE CHARACTERISTICS:
        (A) LENGTH: 379 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:5:

Met Ala Glu Gly Asn His Arg Lys Lys Pro Leu Lys Val Leu Glu Ser
1               5                   10                  15
Leu Gly Lys Asp Phe Leu Thr Gly Val Leu Asp Asn Leu Val Glu Gln
                20                  25                  30
Asn Val Leu Asn Trp Lys Glu Glu Lys Lys Tyr Tyr Asp Ala
            35                  40                  45
Lys Thr Glu Asp Lys Val Arg Ala Met Ala Asp Ser Met Gln Glu Lys
50                  55                  60
Gln Arg Met Ala Gly Gln Met Leu Leu Gln Thr Phe Phe Asn Ile Asp
65                      70                  75                  80
Gln Ile Ser Pro Asn Lys Ala His Pro Asn Met Glu Ala Gly Pro
                85                  90                  95
Pro Glu Ser Gly Glu Ser Thr Asp Ala Leu Lys Leu Cys Pro His Glu
                100                 105                 110
Glu Phe Leu Arg Leu Cys Lys Glu Arg Ala Glu Glu Ile Tyr Pro Ile
            115                 120                 125
Lys Glu Arg Asn Asn Arg Thr Arg Leu Ala Leu Ile Ile Cys Asn Thr
        130                 135                 140
Glu Phe Asp His Leu Pro Pro Arg Asn Gly Ala Asp Phe Asp Ile Thr
145                 150                 155                 160
Gly Met Lys Glu Leu Leu Leu Glu Gly Leu Asp Tyr Ser Val Asp
                165                 170                 175
Val Glu Glu Asn Leu Thr Ala Arg Asp Met Glu Ser Ala Leu Arg Ala
                180                 185                 190
Phe Ala Thr Arg Pro Glu His Lys Ser Ser Asp Ser Thr Phe Leu Val
            195                 200                 205
Leu Met Ser His Gly Ile Leu Glu Gly Ile Cys Gly Thr Val His Asp
210                 215                 220
Glu Lys Lys Pro Asp Val Leu Leu Tyr Asp Thr Ile Phe Gln Ile Phe
225                 230                 235                 240
Asn Asn Arg Asn Cys Leu Ser Leu Lys Asp Lys Pro Lys Val Ile Ile
                245                 250                 255
Val Gln Ala Cys Arg Gly Ala Asn Arg Gly Glu Leu Trp Val Arg Asp
                260                 265                 270
Ser Pro Ala Ser Leu Glu Val Ala Ser Ser Gln Ser Ser Glu Asn Leu
            275                 280                 285
Glu Glu Asp Ala Val Tyr Lys Thr His Val Glu Lys Asp Phe Ile Ala
290                 295                 300
```

```
Phe Cys Ser Ser Thr Pro His Asn Val Ser Trp Arg Asp Ser Thr Met
305                 310                 315                 320

Gly Ser Ile Phe Ile Thr Gln Leu Ile Thr Cys Phe Gln Lys Tyr Ser
            325                 330                 335

Trp Cys Cys His Leu Glu Glu Val Phe Arg Lys Val Gln Gln Ser Phe
            340                 345                 350

Glu Thr Pro Arg Ala Lys Ala Gln Met Pro Thr Ile Glu Arg Leu Ser
            355                 360                 365

Met Thr Arg Tyr Phe Tyr Leu Phe Pro Gly Asn
370                 375
```

(2) INFORMATION FOR SEQ ID NO:6:

(i) SEQUENCE CHARACTERISTICS:
        (A) LENGTH: 418 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:6:

```
Met Phe Lys Gly Ile Leu Gln Ser Gly Leu Asp Asn Phe Val Ile Asn
1               5                   10                  15

His Met Leu Lys Asn Asn Val Ala Gly Gln Thr Ser Ile Gln Thr Leu
            20                  25                  30

Val Pro Asn Thr Asp Gln Lys Ser Thr Ser Val Lys Lys Asp Asn His
            35                  40                  45

Lys Lys Lys Thr Val Lys Met Leu Glu Tyr Leu Gly Lys Asp Val Leu
50                  55                  60

His Gly Val Phe Asn Tyr Leu Ala Lys His Asp Val Leu Thr Leu Lys
65                  70                  75                  80

Glu Glu Glu Lys Lys Lys Tyr Tyr Asp Ala Lys Ile Glu Asp Lys Ala
                85                  90                  95

Leu Ile Leu Val Asp Ser Leu Arg Lys Asn Arg Val Ala His Gln Met
            100                 105                 110

Phe Thr Gln Thr Leu Leu Asn Met Asp Gln Lys Ile Thr Ser Val Lys
            115                 120                 125

Pro Leu Leu Gln Ile Asp Ala Gly Pro Pro Glu Ser Ala Glu Ser Thr
130                 135                 140

Asn Ile Leu Lys Leu Cys Pro Arg Glu Glu Phe Leu Arg Leu Cys Lys
145                 150                 155                 160

Lys Asn His Asp Glu Ile Tyr Pro Ile Lys Lys Arg Glu Asp Arg Arg
                165                 170                 175

Arg Leu Ala Leu Ile Ile Cys Asn Thr Lys Phe Asp His Leu Pro Ala
            180                 185                 190

Arg Asn Gly Ala His Tyr Asp Ile Val Gly Met Lys Arg Leu Leu Gln
            195                 200                 205

Gly Leu Gly Tyr Thr Val Val Asp Glu Lys Asn Leu Thr Ala Arg Asp
            210                 215                 220

Met Glu Ser Val Leu Arg Ala Phe Ala Ala Arg Pro Glu His Lys Ser
225                 230                 235                 240

Ser Asp Ser Thr Phe Leu Val Leu Met Ser His Gly Ile Leu Glu Gly
                245                 250                 255

Ile Cys Gly Thr Ala His Lys Lys Lys Pro Asp Val Leu Leu Tyr
            260                 265                 270
```

```
Asp Thr Ile Phe Gln Ile Phe Asn Asn Arg Asn Cys Leu Ser Leu Lys
        275                 280                 285

Asp Lys Pro Lys Val Ile Ile Val Gln Ala Cys Arg Gly Glu Lys His
        290                 295                 300

Gly Glu Leu Trp Val Arg Asp Ser Pro Ala Ser Leu Ala Val Ile Ser
305                 310                 315                 320

Ser Gln Ser Ser Glu Asn Leu Glu Ala Asp Ser Val Cys Lys Ile His
                325                 330                 335

Glu Glu Lys Asp Phe Ile Ala Phe Cys Ser Ser Pro His Asn Val
                340                 345                 350

Ser Trp Arg Asp Arg Thr Arg Gly Ser Ile Phe Ile Thr Glu Leu Ile
        355                 360                 365

Thr Cys Phe Gln Lys Tyr Ser Cys Cys Cys His Leu Met Glu Ile Phe
        370                 375                 380

Arg Lys Val Gln Lys Ser Phe Glu Val Pro Gln Ala Lys Ala Gln Met
385                 390                 395                 400

Pro Thr Ile Glu Arg Ala Thr Leu Thr Arg Asp Phe Tyr Leu Phe Pro
                405                 410                 415

Gly Asn (2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:7:

Thr Glu Phe Lys His Leu Ser Leu Arg Tyr Gly Ala Lys Phe Asp
1               5                   10                  15

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CTTCACAGTG CGAAAGAACT                                          20

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGTCCACACT GAAGAATGTC TGGAGAAGCA TTTCA                         35

(2) INFORMATION FOR SEQ ID NO:10:
```

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

CCCTCGAGCG GCCGCCATGG CTGAAAACAA ACACCC                                36

(2) INFORMATION FOR SEQ ID NO:11:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

AAGTCGACTT GCCAGGAAAG AGGTAGAAAT ATC                                   33

(2) INFORMATION FOR SEQ ID NO:12:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

GTGCAGGCCG GCAGAGGTGG G                                                21

(2) INFORMATION FOR SEQ ID NO:13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

CCCACCTCTG CCGGCCTGCA C                                                21

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

CCAGAAGAAT CATTGAACAC                                                  20

(2) INFORMATION FOR SEQ ID NO:15:

(i) SEQUENCE CHARACTERISTICS:
            (A) LENGTH: 15 base pairs
            (B) TYPE: nucleic acid
            (C) STRANDEDNESS: single

```
        (D) TOPOLOGY: linear (ii) MOLECULE TYPE: cDNA (xi) SEQUENCE DESCRIPTION: SEQ ID NO:15:

GAGAGTGTTC AATGA                                                    15

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCTGTAAGCT CCTCTTTCAC                                               20

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AAACATCTCT CACTGAGGTA TGGGGCTAAA TTT                                33

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

ACTCTCAGAA CACCAGACAT C                                             21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CCCACCTCTG CAGGCCTGCA C                                             21

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:20:

GCTGTCAAGC TGAGCC                                                    16

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TCAGCTTCCA TATTCCATGG                                                20

(2) INFORMATION FOR SEQ ID NO:22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

ATCACTTGTC CTACCGA                                                   17

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GGCAAGTATT CATTCCC                                                   17

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GATCAATGGT GGGCATCTGG GAA                                            23

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

TTGCCAGGAA AGAGGTAGAA AT                                             22

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GAGATGGTGA AAGAGGTG                                          18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TTGTTTCTCT CCACGGCA                                          18

PROGRAMMED CELL DEATH AND ICH-3

This application claims the benefit of the filing date of U.S. Provisional Application No. 60/023,937, filed Aug. 9, 1996 and is incorporated herein by reference.

STATE AS TO RIGHTS TO INVENTIONS MADE UNDER FEDERALLY-SPONSORED RESEARCH AND DEVELOPMENT

Part of the work performed during the development of this invention was supported by U.S. Government funds. The U.S. Government may have certain rights in this invention.

BACKGROUND OF THE INVENTION

1. Field of the Invention

The invention is generally in the field of molecular biology as related to the control of programmed cell death. The invention also relates to transgenic non-human animals comprising a disrupted Ich-3 (Caspase-11) gene. This invention further relates to methods of making and using the transgenic animals.

2. Related Art

Programmed Cell Death

Apoptosis, also referred to as programmed cell death or regulated cell death, is a process by which organisms eliminate unwanted cells. Such cell death occurs as a normal aspect of animal development as well as in tissue homeostasis and during aging (Glucksmann, A., Biol. Rev. Cambridge Philos. Soc. 26:59–86 (1950); Ellis et al., Dev. 112:591–603 (1991); Vaux et al., Cell 76:777–779 (1994)). Programmed cell death can also act to regulate cell number, to facilitate morphogenesis, to remove harmful or otherwise abnormal cells and to eliminate cells that have already performed their function. Additionally, programmed cell death is believed to occur in response to various physiological stresses such as hypoxia or ischemia. The morphological characteristics of apoptosis include plasma membrane blebbing, condensation of nucleoplasm and cytoplasm and degradation of chromosomal DNA at inter-nucleosomal intervals. (Wyllie, A. H., in Cell Death in Biology and Pathology, Bowen and Lockshin, eds., Chapman and Hall (1981), pp. 9–34).

Apoptosis is achieved through an endogenous mechanism of cellular suicide (Wyllie, A. H., in Cell Death in Biology and Pathology, Bowen and Lockshin, eds., Chapman and Hall (1981), pp. 9–34) and occurs when a cell activates its internally encoded suicide program as a result of either internal or external signals. The suicide program is executed through the activation of a carefully regulated genetic program (Wylie, A. H., et al., Int. Rev. Cyt. 68: 251 (1980); Ellis, R. E., et al., Ann. Rev. Cell Bio. 7: 663 (1991); Yuan, Y. Curr. Op. Cell. Biol. 7:211–214 (1995)).

In many cases, gene expression appears to be required, since cell death can be prevented by inhibitors of RNA or protein synthesis (Cohen et al., J. Immunol. 32:38–42 (1984); Stanisic et al., Invest. Urol. 16:19–22 (1978); Martin et al., J. Cell Biol. 106:829–844 (1988). A genetic pathway of programmed cell death was first identified in the nematode C. elegans (Ellis, R. E., et al., Annu. Rev. Cell Biol. 7:663–698 (1991)). In this pathway, the function of two genes, ced-3 and ced-4, are required for cells to undergo programmed cell death Genetic mosaic analysis indicated that both ced-3 and ced-4 most likely act in dying cells to induce cell death; thus, they are essential parts of intracellular machinery involved in execution of cell death (Yuan & Horvitz, Dev. Biol. 138:33–41 (1990)). Furthermore, in C. elegans, the products of ced-3 and ced-4 genes carry out the program of cellular suicide (Yuan & Horvitz, Dev. Bio. 138: 33 (1990)).

Amino acid sequence of CED-3 protein is homologous to mammalian interleukin-1β converting enzyme (ICE) with 28% amino acid identity (Yuan et al., Cell 75:641–652 (1993)). The C terminal half of the CED-3 is more homologous to ICE (43% identity), which includes the active pentapeptide QACRG present in all members of the ICE/CED-3 family.

Interleukin-1-β Converting Enzyme (ICE) Family

The interleukin-1β converting enzyme (ICE) family is a growing family of cysteine proteases involved in cytokine maturation and apoptosis (Yuan, J., Curr. Opin. in Cell Biology 7:211–214 (1995)). ICE is a cytoplasmic cysteine protease responsible for proteolytically processing pro-interleukin-1β (31 kDa) into active form (17 kDa) (Thornberry, N. A., Nature 356:768–774 (1992), Cerretti, D. P., et al., Science 256:97–100 (1992)). ICE is synthesized as a precursor of 45 kDa which is proteolytically cleaved during activation to generate two subunits of 22 kDa p20) and 10 kDa (p10) (Thornberry, N. A., et al., Nature 356:768–774 (1992)). X-ray crystallography analysis of three dimensional structure of ICE showed that ICE is a homodimer of activated ICE p20 and p10 subunits (Wilson, K. P., et al., Nature 370:270–275 (1994); Walker, N. P. C., et al., Cell 78:343–352 (1994)). Activated ICE can cleave the inactive ICE precursor; however, in vitro synthesized ICE precursor cannot cleave itself (Thornberry, N. A., et al., Nature 356:768–774 (1992)), suggesting that ICE may need to be activated by another protease in vivo.

The amino acid sequence of ICE shares 29% identity with C. elegans cell death gene product Ced-3 (Yuan et al., Cell 75:641–752 (1993)) which suggests that ICE may play a role in controlling mammalian apoptosis.. Expression of Ice in a number of mammalian cell lines induces apoptosis (Miura et al., Cell 75:653–660 (1993); Wang et al., Cell 87:739–750 (1994)). Microinjection of an expression vector of crmA, a cowpox virus gene encoding a serpin that is a specific inhibitor of ICE, prevents not only death of neurons from dorsal root ganglia induced by trophic factor deprivation but also the death of ciliary ganglia (Gagliardini et al., Science 263:826–828 (1994); Li et al., Cell 80:401–411 (1995); Allsopp et al., Cell 73:295–307, (1993)). Expression of crmA can also suppress apoptosis induced by TNF-α and Fas (Enari et al., Nature 375:78–81 (1995); Los et al., Nature 375:81–83 (1995); Kuide et al., Science 267:2000–2002 (1995); Miura et al., Proc. Natl. Acad. Sci. U.S.A. 92:8318–8322 (1995)). These experiments suggest that the members of the ICE family play important roles in controlling mammalian apoptosis. These results did not indicate, however, which member of the ICE family is critical for cell death since CrmA may cross-inhibit other members of the ICE family.

The mammalian ICE/CED-3 family now includes eight members: ICE, TX/$ICE_{rel}$II/ICH-2, $ICE_{rel}$III, ICH-1/NEDD2, CPP32/Yama/Apopain, MCH2, MCH-3/ICE-LAP3/MCH-2 and ICH-3 (Kumar et al., Genes Dev. 8:1613–1626 (1994); Fernandes-Alnemri, et al., J. Biol. Chem. 269:30761–30764 (1994); Fernandez-Alnemri et al, Cancer Res. 55:2737–2742 (1995); Fernandes-Alnemri et al., Cancer Res. 55:6045–6052 (1996); Wang et al., Cell 78:739–750 (1994); Faucheu, et al, EMBO J. 14:1914–1922 (1995); Tewari & Dixit, J. Biol. Chem. 270:3255–3260 (1995); Kamens et al., J. Biol Chem. 270:15250–15256

(1995); Munday, N. A., et al., *J. Biol. Chem.* 270:15870–15876 (1995); Duan, H. J., et al., *J. Biol. Chem.* 271:1621–1625 (1996); Lippke, J. A., et al., *J. Biol. Chem.* 271:1825–1828 (1996)). Since ICH-3 is most homologous to TX, it may be the mouse version of human TX. This cannot be concluded at the moment, however, because TX has been shown to cleave pro-ICE (Faucheu, et al., *EMBO J.* 14:1914–1922 (1995)) whereas ICH-3 has not been shown to cleave pro-ICE in a similar assay (data not shown). The current designation of ICH-3 is Caspase-11.

Overexpression of Nedd-2/Ich-$1_L$ induces cell death very effectively (Kumar et al., *Genes Dev.* 8:1613–1626 (1994); Wang et al., *Cell* 87:739–750 (1994)). Expression of CPP32/Yama in full length cDNA induces apoptosis of insect Sf9 cells but not that of mammalian cells (Fernandes-Alnemri et al., *J Biol. Chem.* 269:30761–30764 (1994); E. S. Alnemri, personal communication). Recombinant CPP32/Yama is inactive and cleavage of CPP32/Yama by ICE in vitro activates the precursor (Tewari et al., *Cell* 81:801–809 (1995b)), suggesting that in vivo CPP32(Yama may be activated by another protease to induce apoptosis. Expression of MCH2α also induces apoptosis of insect Sf9 cells but not that of mammalian cells (Fernandes-Alnemri et al., *Cancer Res.* 55:2737–2742 (1995)). Thus, the members of the ICE family can be classified into 2 classes: those that when overexpressed in mammalian cells can induces apoptosis (e.g. Ice and Ich-1) and those that when overexpressed in mammalian cells cannot induce apoptosis (e.g. CPP32 and Mch-2). These experimental evidence suggest that in vivo members of the ICE family may be arranged in proteases cascades and certain members of the ICE family may activate other members of the ICE family.

The control of apoptosis in mammals is much more complex than that in *C. elegans* where function of one ced-3 gene controls all programmed cell death (Ellis & Horvitz, *Cell* 44:817–829 (1986)). In contrast to *C. elegans,* multiple proteases may be involved in regulation of programmed cell death (apoptosis) in mammals. This hypothesis is supported by many in vitro studies. For instance, peptide inhibitors of ICE such as YVAD-cmk inhibit Fas induced apoptosis but requires much higher doses than that for inhibiting ICE (Enari et al., *Nature* 375:78–81 (1995)), suggesting that inhibition of additional ICE-like protease(s) is required for complete inhibition of Fas induced apoptosis. Similarly, Ac-DEVD-CHO, a peptide inhibitor of CPP32/Yama/Apopain, inhibits poly(ADP-ribose) polymerase (PARP) cleavage at a dose of 1 nM but requires 1 μM to cause 50% inhibition of apoptosis in an cell-free system (Nicholson, D. W., et al., *Nature* 376:37–43 (1995)), suggesting that inhibition of protease(s) other than CPP32/Yama/Apopain is required for complete inhibition of apoptosis in this system. Furthermore, inhibitors that are known not to have effects or have little effects on ICE like cysteine proteases such as cysteine protease inhibitors trans-epoxysucciniyl-L-leucylamido-(4-guanidino) butane (E64) and leupeptin, calpain inhibitors I and II, and serine protease inhibitors diisopropyl fluorophosphate and phenylmethylsulfonyl fluoride, were found to inhibit apoptosis induced by T cell receptor binding-triggered apoptosis (Sarin et al., *J. Exp. Med.* 178:1693–1700 (1993)), suggesting that not only cysteine proteases but also serine proteases may play important roles in mammalian cell apoptosis.

Cytotoxic T lymphocytes (CTL) are important players in host cell-mediated immunity (reviewed by Henkart & Sitkovsky, *Curr. Opin. in Immun.* 5:404–410 (1994)). Granzyme B(GraB) is a serine protease Granzyme B is a serine protease required for the cytotoxic activity of lymphocytes (Shi et al., *J. Exp. Med.* 176:1521–1529(1992)). It also plays a major role in apoptosis induced by CTLs since mice that are deficient for GraB generated by gene targeting technique are severely defective in CTL induced apoptosis (Heusel, J. W., et al., *Cell* 76:977–987 (1994)). GraB can induce apoptosis of many if not all cell types in the presence of pore forming protein perforin (Shi et al., *J. Exp. Med.* 175:553–566 (1992) & Shi et al., *J. Exp. Med.* 176:1521–1529 (1992)).

Recent work showed that apoptosis of embryonic fibroblasts induced by granzyme B is mediated through ICE (Shi et al., Proc. Natl. Acad. Sci. In Press (1996)) Apoptosis induced by granzyme B and perforin can be inhibited by inhibitors of the ICE family, including CrmA, ICH-$1_S$ and a mutant ICE (Shi et al., Submitted (1996)). Most significantly, embryonic fibroblasts from Ice deficient mice are resistant to granzyme B/perforin induced apoptosis, suggesting that ICE itself is required for cytoxicity of granzyme B/perforin in at least certain cell types (Shi et al, Submitted (1996)). Granzyme B does not, however, cleave and activate ICE precursor directly (Darmon, A. J., et al., *J. Biol. Chem.* 269:32043–32046 (1994)), suggesting that there are intermediate steps of regulation between granzyme B and ICE.

A recent report showed that CPP32, a member of the ICE family, is activated by cytotoxic T-cell-derived GraB, suggesting that CPP32 is important for CTL killing (Darmon, A. J., et al., *Nature* 377:446–448 (1995)). CPP32, however, cannot be the only ICE family activated by CTL since CrmA is a very poor inhibitor of CPP32 (Nicholson, D. W., et al, *Nature* 376:37–43 (1995)). Tewari et al., *Chem.* 270:22605–22708 (1995) showed that expression of crmA completely blocks the $Ca^{2+}$-independent component of CTL-killing (i.e. Fas-mediated); if CPP32 were the only ICE family member responsible for CTL cytotoxicity, expression of crmA should not suppress CTL killing. It is predicted that there are additional members of the ICE family which play an important role in CTL induced apoptosis. The amino acid sequence of GraB is not homologous with ICE; however, GraB and ICE share many enzymatic similarities. Like ICE, GraB requires Asp at P1 position for cleavage. Inhibitors of ICE or the ICE family, CrmA, ICH-$1_s$ and a mutant ICE are effective inhibitors of GraB/perforin induced apoptosis (Shi et al., Submitted (1996)). Embryonic fibroblasts that are deficient in ICE from Ice−/− mice are resistant to GraB/perforin induced apoptosis (Shi et al, Submitted (1996)), suggesting that ICE is critical for GraB/perforin induced apoptosis in at least certain cell types. ICE itself cannot be directly cleaved by GraB (Darmon, A. J., et al., *J. Biol. Chem.* 269:32043–32046 (1994)) and thus, although ICE is required for GraB/perforin induced apoptosis in certain cells, GraB does not activate ICE directly. One possibility is that GraB activates another ICE family member which may then directly or indirectly activate ICE and the activator of ICE can be inhibited by CrmA.

Transgenic Animals

With so many members in the ICE/CED-3 family, it is important to determine the ICE/CED-3 family member's functions individually. Transgenic mice are an ideal model for accomplishing this by generating mutations in the genes of interest, resulting in "knock-out" mice. Using such models, it has already been shown that mice deficient in Ice develop normally but are resistant to endotoxic shock induced by lipopolysaccharide (LPS). This can be attributed to their defect in production of mature IL-1β (Li et al., *Cell* 80:401–411 (1995); Kuida et al., *Science* 267:2000–2003 (1995)). Furthermore, Ice deficient thymocytes undergo apoptosis normally when stimulated with dexamethasone and γ-irradiation but are resistant to Fas induced apoptosis (Kuida et al., Science 267:2000–2003 (1995)), suggesting that ICE is required for Fas but not dexamethasone and γ-irradiation induced apoptosis in thymocytes. Ice may be involved, however, in γ-irradiation induced cell death in concanavalin A (conA)-stimulated splenocytes (Tamura et al., Nature 376:596–599 (1995)). Expression of Ice is induced in splenocytes stimulated by conA and induction of Ice expression enhances the susceptibility of mitogen activated T cells to cell death induced by γ-irradiation and DNA-damaging chemotherapeutic agents such as adriamycin or etoposide induced cell death.

Generation of mutant mice by gene targeting technique and ultimately, making crosses all of potential candidate genes, should provide vital information about the genetic and biochemical pathways of apoptosis. Over the last several years, transgenic animals containing specific genetic defects, e.g., resulting in the development of, or predisposition to, various disease states, have been made. These transgenic animals can be useful in characterizing the effect of such a defect on the organism as a whole, and developing pharmacological treatments for these defects.

The relevant techniques whereby foreign DNA sequences can be introduced into the mammalian germ line have been developed in nice. See Manipulating the Mouse Embryo (Hogan et al., eds., 2d ed., Cold Spring Harbor Press, 1994) (ISBN 0-87969-384-3). At present, one route of introducing foreign DNA into a germ line entails the direct microinjection of a few hundred linear DNA molecules into a pronucleus of a fertilized one-cell egg. Microinjected eggs may then subsequently be transferred into the oviducts of pseudopregnant foster mothers and allowed to develop. It has been reported by Brinster et al. (1985), that about 25% of the mice that develop inherit one or more copies of the microinjected DNA.

More specifically, "knock-out" mice, a specific type of transgenic animal, are obtained by first making mutant ES cells. Chimeric mice are then made by injecting ES cells into blastocytes and the chimera are bred to obtain the germline transmitted mutation.

In addition to transgenic mice, other transgenic animals have been made. For example, transgenic domestic livestock have also been made, such as pigs, sheep, and cattle. Once integrated into the germ line, the foreign DNA may be expressed in the tissue of choice at high levels to produce a functional protein. The resulting animal exhibits the desired phenotypic property resulting from the production of the functional protein.

In light of the various biological roles of apoptosis, there exists a need in the art to develop transgenic animals, e.g., transgenic mice, wherein genes involved in apoptosis have been modified. There also exists a need in the art to develop methods to test compounds directed to modifying the apoptotic condition using these transgenic animals. A further need in the art is to develop treatments for various pathological states in which apoptosis has been found to occur.

SUMMARY OF THE INVENTION

It has now been found that overexpression of Ich-3 in rat-1 and HeLa cells induces apoptosis which can be inhibited by CrmA and Bcl-2. These results indicate that ICH-3 acting as an upstream regulator of ICE may play an important role in apoptosis and inflammatory responses. It has further been found that inactivation of the Ich-3 gene by gene targeting produces a transgenic animal (mutant mouse) which is resistant to endotoxic shock (septic shock) induced by lipopolysaccharide (LPS).

This invention satisfies a need in the art for a means to study the modulation of apoptosis regulated by the Ich-3 gene by providing a method for modulating programmed cell death and by providing a transgenic non-human animal comprising a disrupted Ich-3 gene. Surprisingly, such an animal is resistant to septic shock.

The invention is first directed to a method for modulating programmed cell death comprising the use of ICH-3. The method is further directed to promoting proIL-β processing by using ICH-3. More preferably the processing occurs in the presence of interleukin converting enzyme (ICE).

The invention is also directed to an antibody (monoclomal or polyclonal) which specifically binds to ICH-3. Preferably the antibody binds to a 38 kDa or a 43 kDa portion of the ICH-3 protein or to the amino acid peptide TEFKHLSLRYGAKFD.

The invention is further directed to a transgenic non-human animal in which the Ich-3 gene is disrupted. Preferably the non-human animal is a mouse. Such ICH-3 deficient mice exhibit resistance to septic shock. Furthermore, neonatal ICH-3 deficient female mice show delayed follicle activation, a reduced endowment of primordial oocytes and abnormal follicles.

In a specific embodiment of the invention, the transgenic non-human animal is a mouse. Moreover, in an additional specific embodiment of this invention, the Ich-3 gene comprises an insertion/substitution resulting in deletion of 16 amino acids from the coding region of Ich-3 in exon 5 which includes the QACRG active site.

In an additional embodiment, this invention provides a method of making the transgenic non-human animal of the invention comprising providing a first DNA molecule with an intact Ich-3 gene; providing a targeting vector capable of disrupting said Ich-3 gene upon homologous recombination with said DNA molecule; placing said first DNA molecule and said targeting vector in contact under conditions where the DNA molecules undergo homologous recombination to produce a second DNA molecule comprising a disrupted Ich-3 gene; introducing said second DNA molecule into blastocytes; implanting the blastocytes into the uterus of a pseudopregnant female; and delivering transgenic animals of the invention from said pseudopregnant female.

In an additional embodiments, this invention provides a method of testing compounds affecting sepsis by providing a transgenic non-human animal having a disrupted Ich-3 gene, wherein the animal exhibits an increased resistance to sepsis. One administers a compound to be tested to the transgenic animal, and determines the effect of the compound on the resistance to sepsis.

In another embodiment, the invention provides for increasing the resistance to sepsis or septic shock by inhibiting ICH-3 in normal animals.

In additional embodiments, this invention provides a method of testing compounds affecting follicular development by providing a transgenic non-human animal having a disrupted Ich-3 gene, wherein the animal exhibits delayed follicle activation as characterized by a reduced endowment of primordial oocytes and abnormal follicles. One administers a compound to be tested to the transgenic animal, and determines the effect of the compound on the delayed follicular development of the animal.

BRIEF DESCRIPTION OF THE FIGURES

FIGS. 1A–1B. The nucleotide sequence of Ich-3 cDNA SEQ ID NO:1 and predicted amino acid sequence of ICH-3 protein SEQ ID NO:2. The initiation codon and stop codon are indicated in bold. The sequence coding for QACRG active site and polyadenylation signal are underlined. Potential cleavage sites are indicated by arrows below the residue.

FIG. 2A. Sequence and structural comparison of the mouse ICH-3 with other closely related members of cysteine protease family SEQ ID NOS:2–6. TX, $ICE_{rel}$-II and ICH-2 are the same protein. Dotted lines are spaces in the sequence to allow optimal alignment. The catalytic $Gly_{238}$, $Cys_{285}$ and $His_{237}$ residues are marked by an asterisk above the residues as indicated by x-ray crystallography analysis (Wilson et al., 1994; Walker et al., 1994). The residues whose amino acid side chains form the P1 pocket are indicated by a "^" above the residue. And those for binding P2–P4 residues are indicated by a "♦". Known and predicted Asp-X cleavage sites which result in the p20/p10 subunits are indicated by arrows below the residue. The potential processing residues are underlined. Residues conserved in more than three ICE members are in bold. The numbers at the end of each lane are the numbers of amino acid of the protein.

Figure 2B:
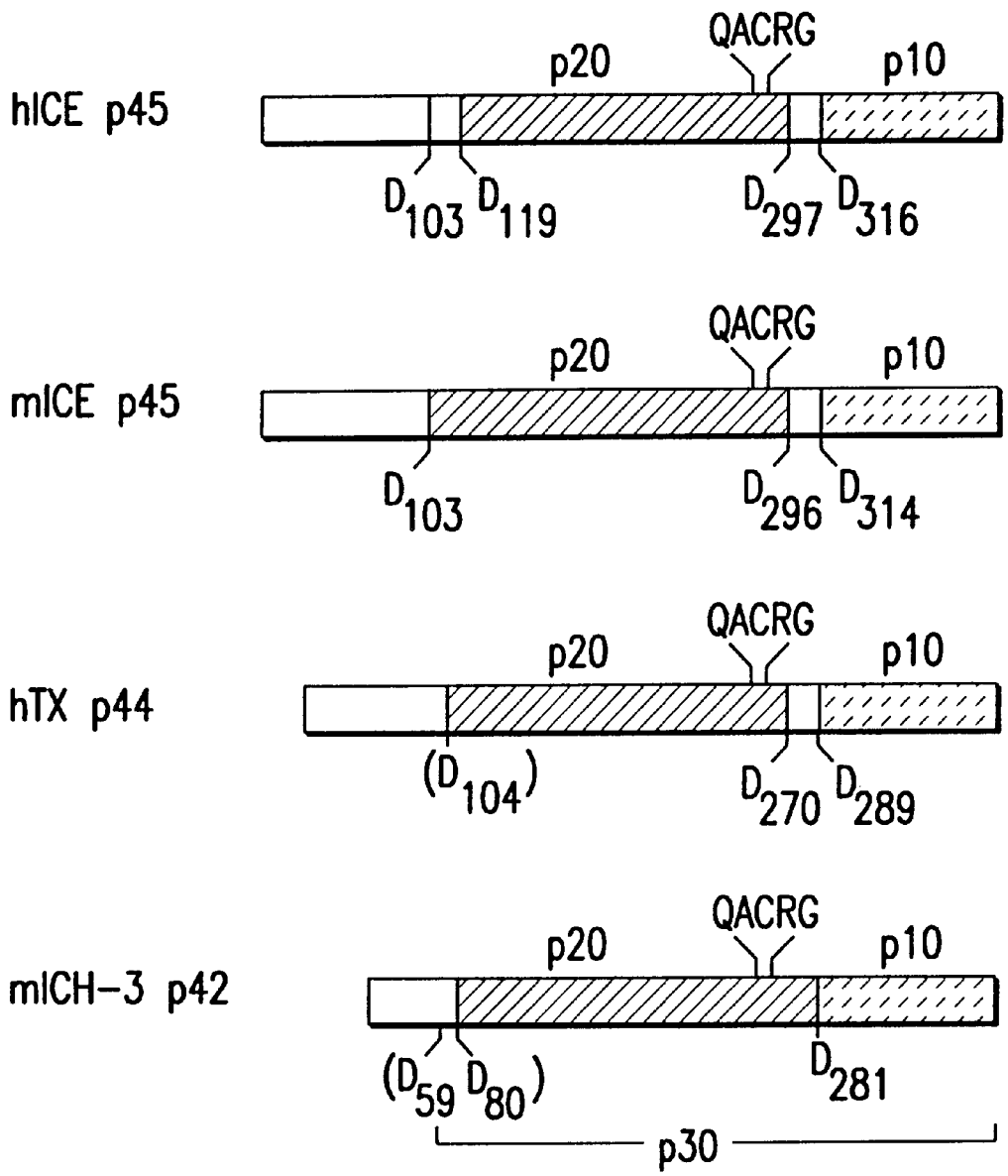

FIG. 2B. The structure motifs of hICE, mICE, ICH-3 and hICH-2. The predicted Asp residues of ICH-3 cleavage sites are indicated. The position of the absolutely conserved pentapeptide sequence QACRG, which includes the catalytic Cysteine residue, is indicated above the bars. The black bar and hatched bar represent p20 and p10 domains, respectively.

Figure 3A:
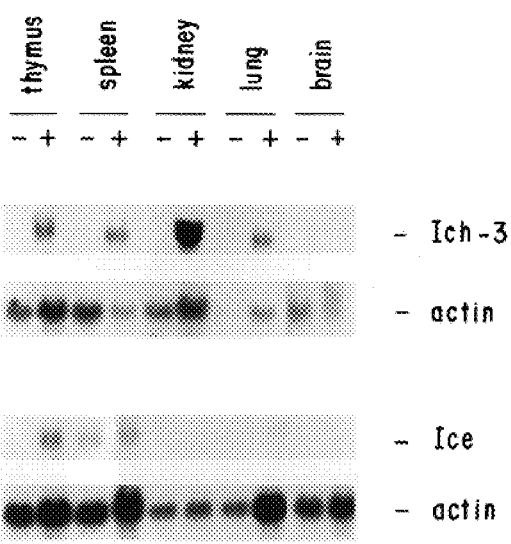

FIG. 3A Induction of Ich-3 mRNA expression by LPS. Total RNAs were isolated from tissues of 7–10 weeks old mice with or without LPS injection (40 mg/kg). The "+" and "−" sign represent with or without LPS injection. 5 µg total RNA from each tissue was loaded per lane. Lane 1, 2, 3, 4, and 5 are total RNAs isolated from thymus, spleen, kidney, lung and brain, respectively. The amount of RNA was adjusted by β-actin blotting.

Figure 3B:
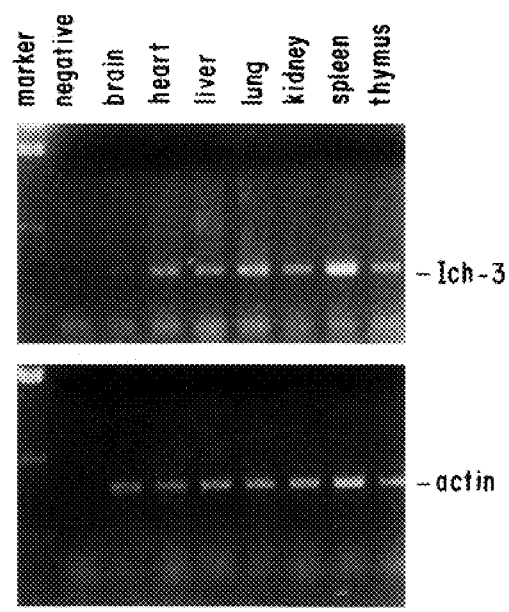

FIG. 3B. Expression pattern of Ich-3 in different tissues from wild type mice. 1 µg of total RNA was used for RT-PCR. The amount of PCR product was adjusted by β-actin.

Figure 3C:
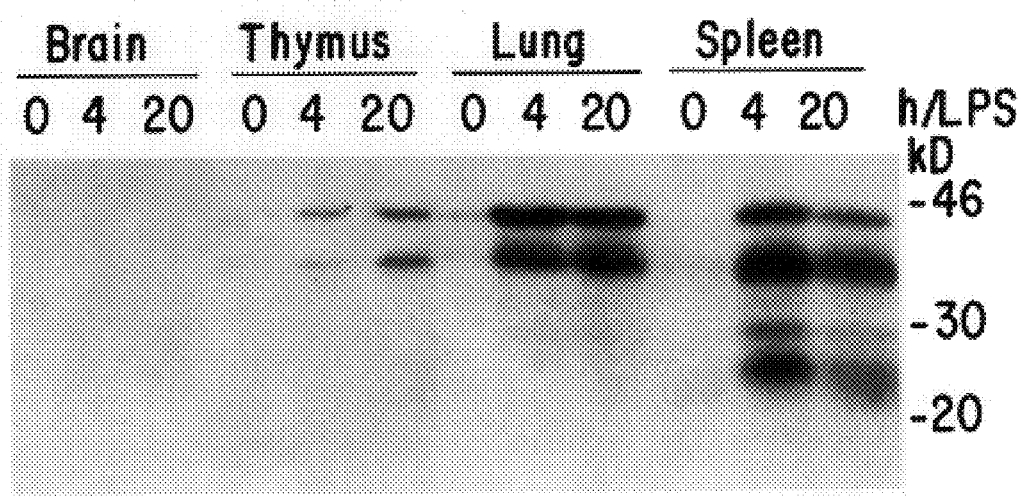
Figure 4A:
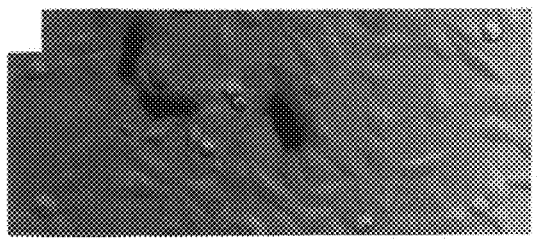
Figure 4B:
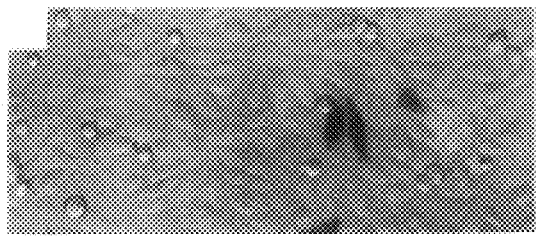
Figure 4C:
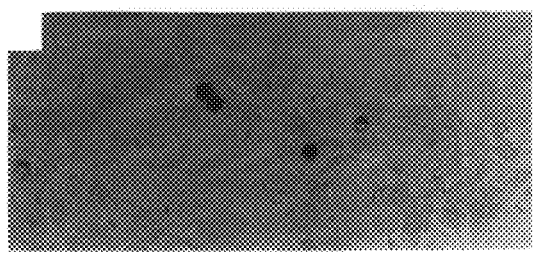
Figure 4D:
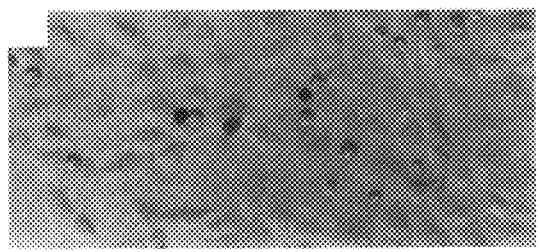

FIG. 3C. Induction of ICH-3 protein expression by LPS. Proteins were isolated from tissues of 7–10 weeks old mice before and after LPS injection. The numbers (0, 4, 20) represent the hours after LPS injection. The amount of protein loaded from each sample was 60 µg per lane except thymus, which was 20 µg. The western blot was probed with a rat anti-ICH-3 monoclonal antibody.

FIGS. 4A–4D. ICH-3 induces apoptosis in Rat-1 cells. Rat-1 cells were transiently transfected with βactGal control (pβactGal vector alone)—FIG. 4A, mutant Ich-3-lacZ fusion under the control of β-actin promoter (pβactS6Z)—FIG. 4B, mouse Ice-lacZ fusion under the control of β actin promoter (pβact10Z)—FIG. 4C and Ich3-lacZ fusion under the control of CMV promoter (pCMVM26Z)—FIG. 4D. 24 hours after transfection, the cells were fixed and stained with X-Gal solution for 3 hours.

Figure 5A:
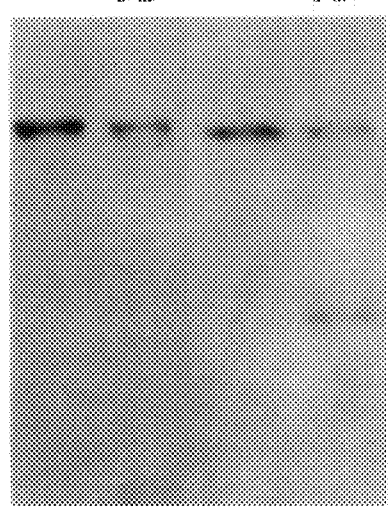
Figure 5B:
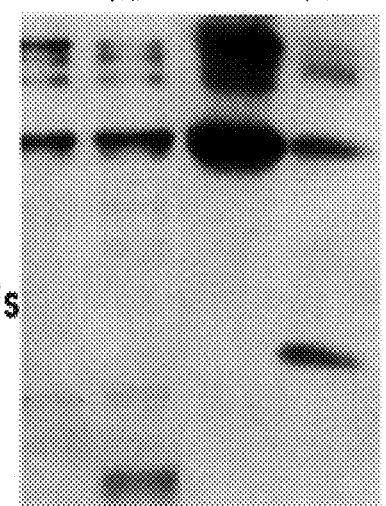

FIG. 5A–5B. Cleavage of ICH-3 protein by granzyme B. 10 µg His-tagged ICH-3 protein purified from E. coli was incubated with 20 ng of GraB in the presence of 10 mM DT at 30° C. for 1 hour. The result was detected by Western blotting with a peptide antibody against p20 portion of ICH-3.

Figure 6:
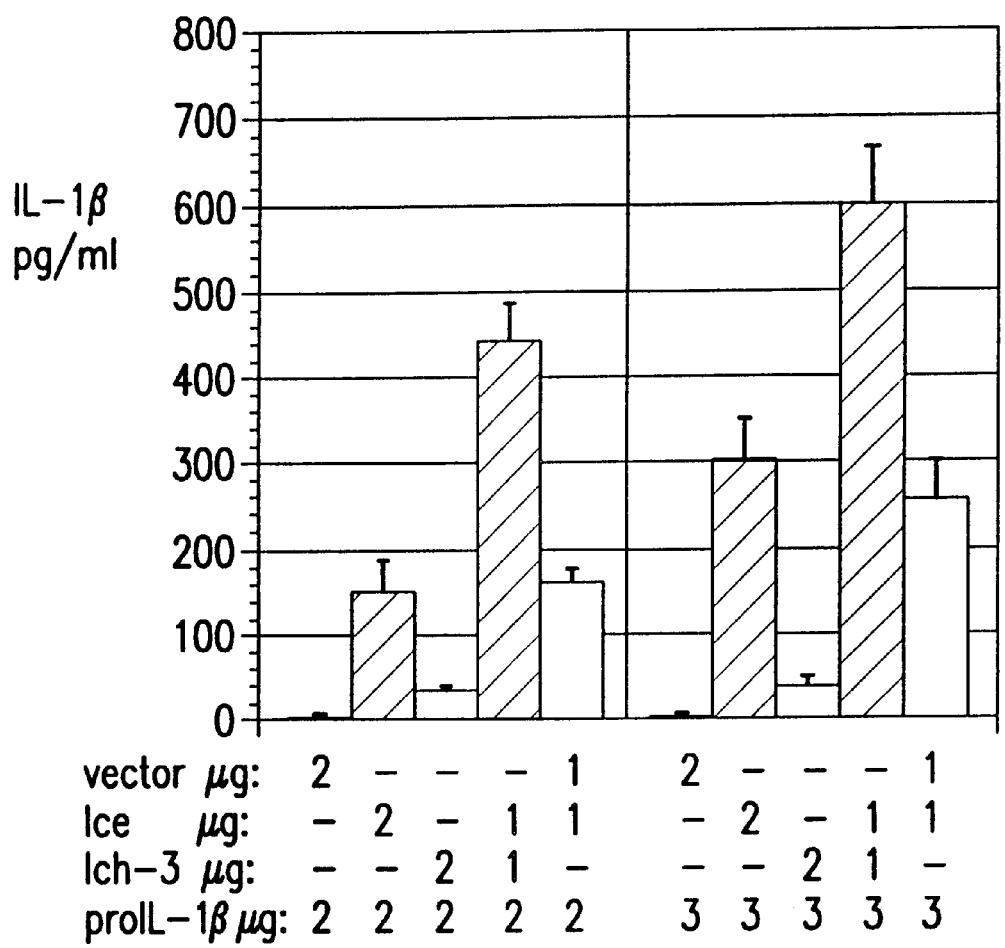

FIG. 6. ICH-3 does not process proIL-1β directly but promotes processing of proIL-1β by ICE. COS cells were cotransfected with mouse proIL-1β (PCMVS11) and with either Ice (pβactM10Z) or Ich-3 (pCMVM26Z) or both. Vector DNA was added to each transfection to equalize the total amount of transfected DNA so that total amount of DNA is the same in each group of transfection. Each set of data was from at least three independent transfection results. 24 hours after transfection, supernatant was collected and subjected for ELISA test. The height of the bars represent the concentration of detected mature IL-1β pg/ml.

Figure 7A:
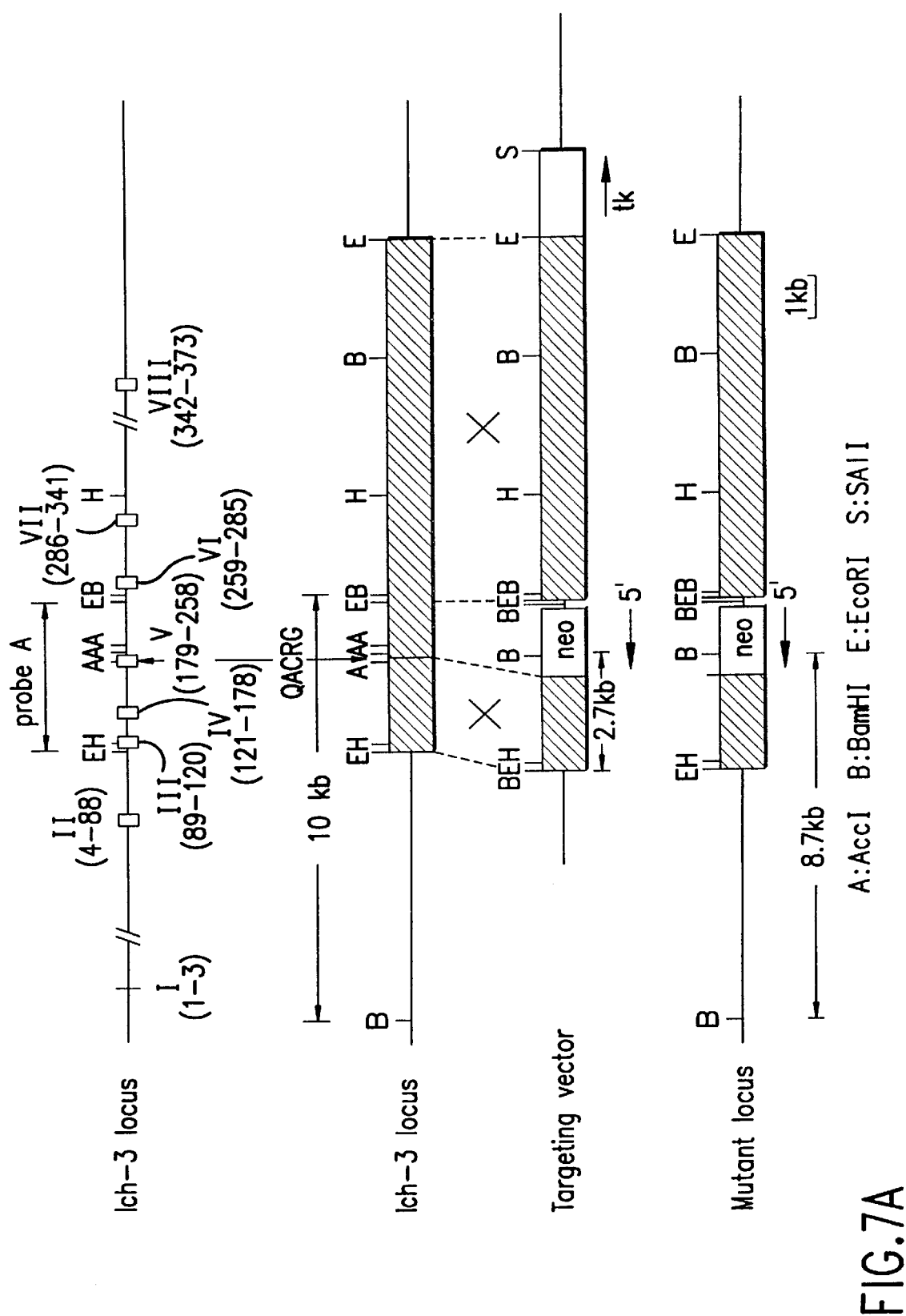
Figure 7B:
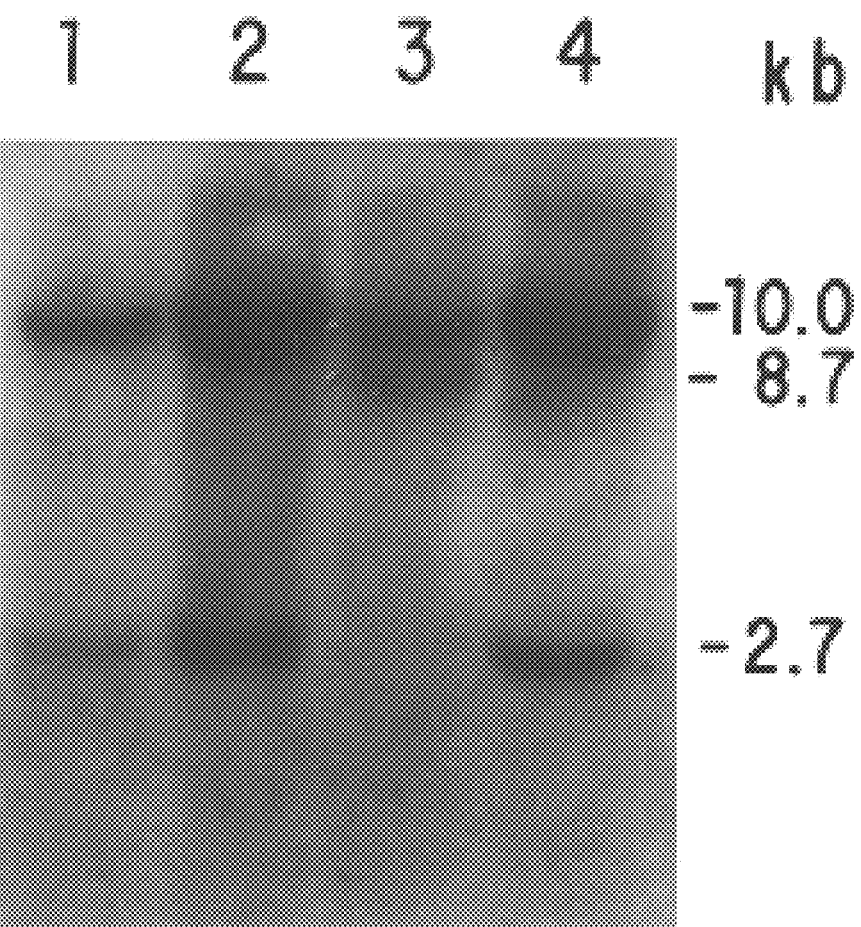
Figure 7C:
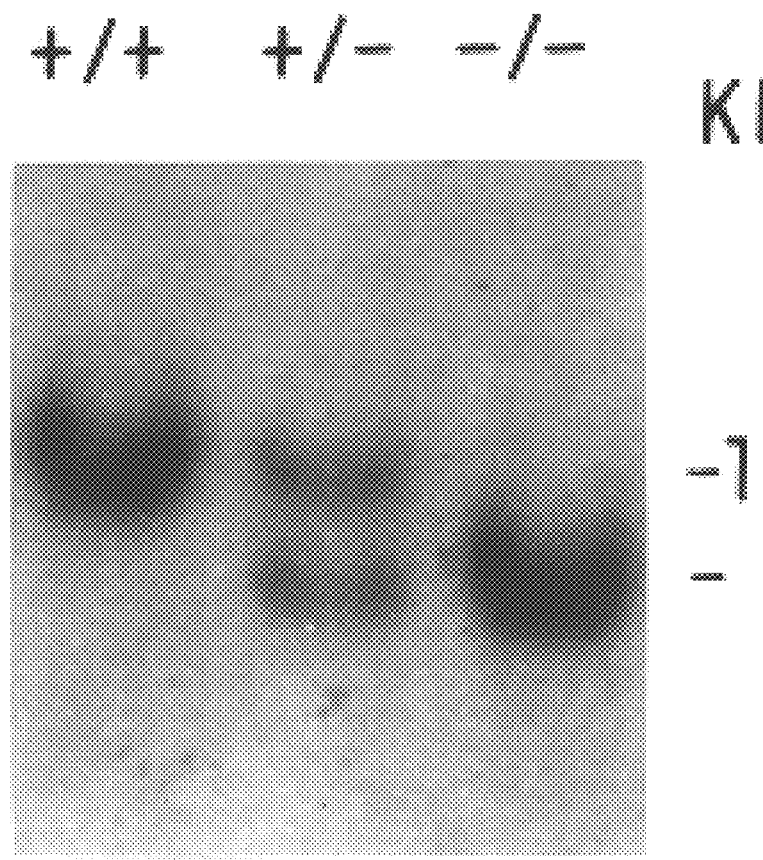

FIGS. 7A–7C. Targeted disruption of the Ich-3 Gene.

FIG. 7A. Structure of the mouse Ich-3 gene. Exons are depicted as open boxes and are numbered from the exon encoding ATG translation initiation codon. Amino acids residues of each exon are indicated in the parenthesis. The locations and transcription orientation of PGKneo and HSVtk selection cassettes are indicated. Restriction enzyme sites used for construction and Southern blotting are shown Diagnostic probes used for Southern blot analysis are shown on the top of the figure.

FIG. 7B. Southern blot analysis of ES cell DNA. DNA was digested with BamHI and blot was hybridized to probe A. The wild-type allele contains a 10 kb BamHI fragment and the mutant allele contains a 8.7 kb BamHI fragment because of an additional BamHI site in the neo cassette. Random integration of the targeting vector gives a 2.7 kb BamHI fragment because the vector has an additional BamHI site next to the insert. Homologous recombinant ES clones were successfully screened using an internal probe. Two criteria to recognize the homologous recombination event were used: the disappearance of 2.7 kb BamHI fragment and appearance of 8.7 kb BamHI fragment.

FIG. 7C Southern blot analysis of tail DNA from wild type, heterozygous and mutant. DNA was digested with BamHI and blot was hybridized to probe A. The wild-type allele is a 10 kb BamHI fragment and the mutant allele is a 8.7 kb BamHI fragment.

FIGS. 8A–8D. Expression of Ich-3 in Mutant Mice.

Figure 8A:
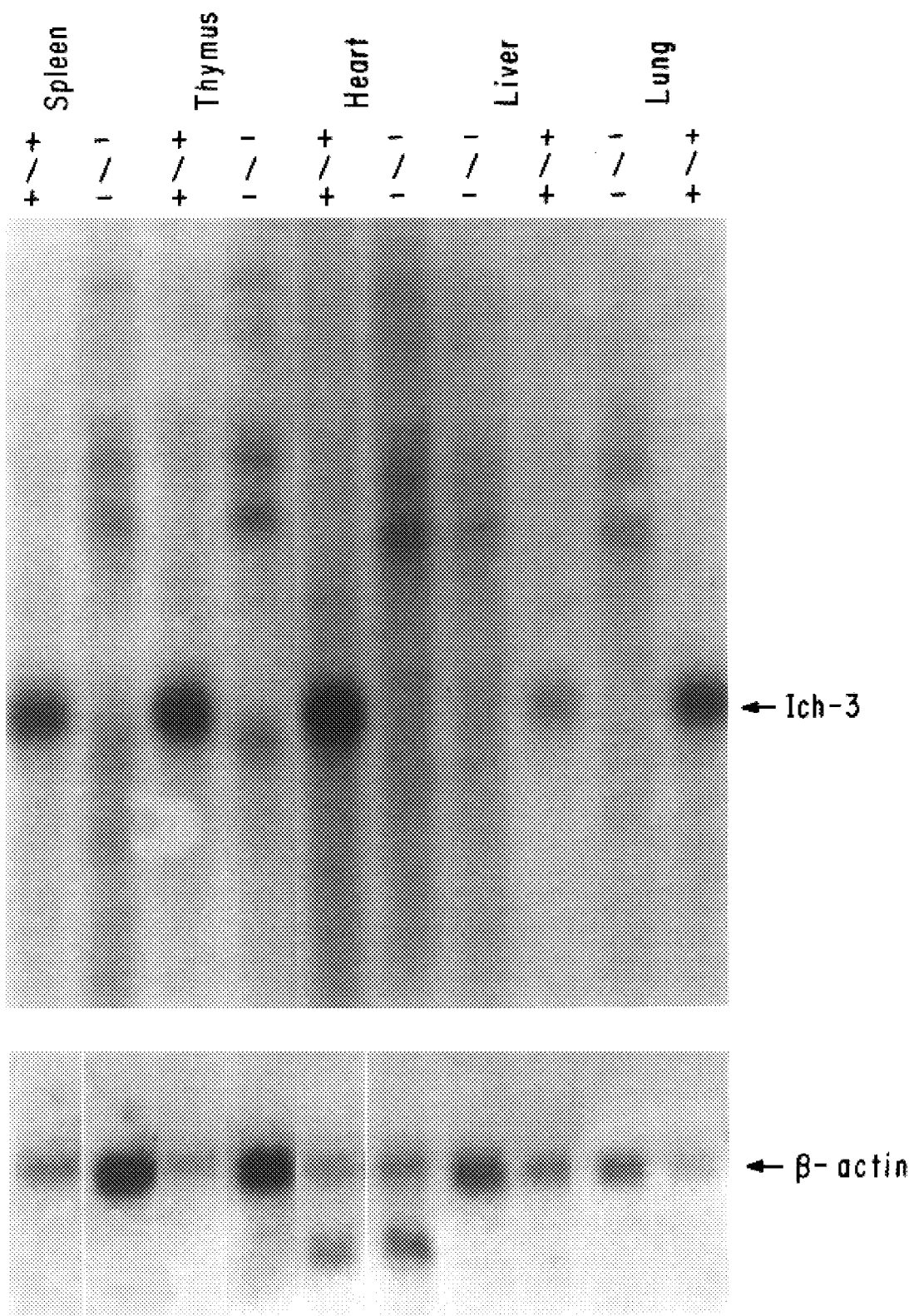

FIG. 8A. Expression of Ich-3 in Endotoxic Shock. Total RNA was isolated from the tissues 5 hr after administration of LPS. Expression was analyzed by Northern blotting with Ich-3 cDNA (0.8 kb PstI fragment of BSNO12) as a probe. Genotypes were indicated as +/+ (wild-type) and −/− (mutant).

Figure 8B:
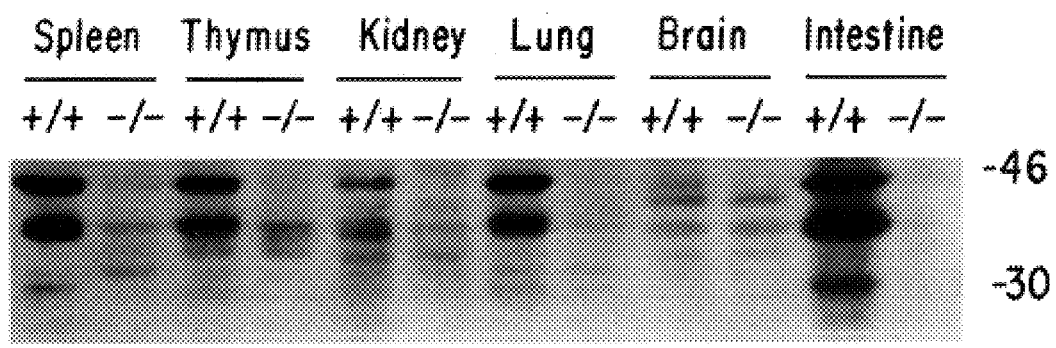

FIG. 8B. Absence of ICH-3 protein in Ice-3 mutant mice. Proteins were isolated from different tissues of both wild type (+/+) and homozygous mutant Ich-3 (−/−) mice 4 hours after LPS injection (40 mg/kg). 20 µg proteins were loaded in each lane for western blot analysis using a rat-anti-Ich-3 monoclonal antibody.

Figures 8C, 8D:
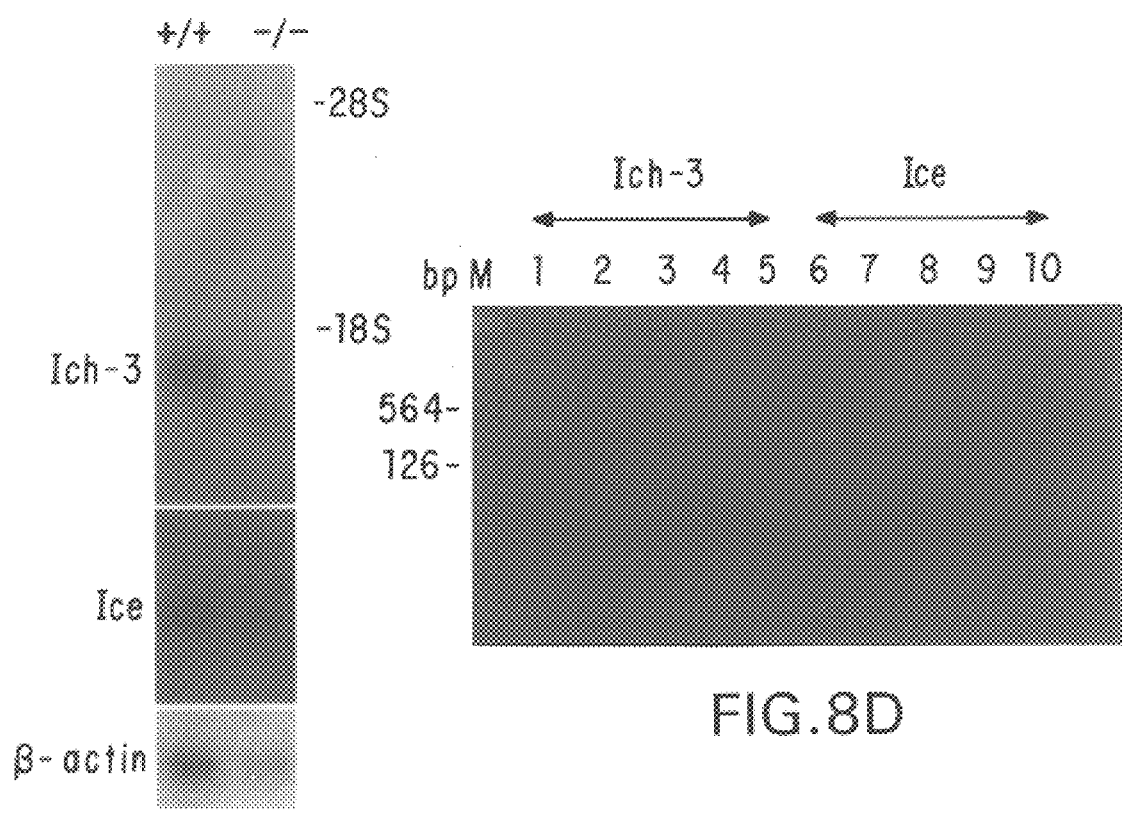

FIG. 8C Northern blot analysis of Ice and Ich-3 expression. Poly (A)⁺RNA was isolated from thymus of wild-type and Ich-3 mutant. 2 (g of poly(A)⁺RNA was loaded in each lane, and the blot was hybridized with Ich-3 cDNA (0.8 kb PstI fragment of BSNO12), Ice cDNA (PCR fragment of primer set MICE3 and MICE4) or chicken β-actin A 1.4 kb Ich-3 transcript was detected in wild type but not in Ich-3 mutant. A 1.4 kb Ice transcript was detected in both wild type and Ich-3 mutant in comparable amount.

FIG. 8D. Reverse-transcription PCR analysis of Ice and Ich-3 expression. The cDNA templates were reverse transcribed from mRNA isolated from thymus (Lanes 1, 3, 6, and 8) and kidney (lanes 2, 4, 7, and 9). Lanes 5 and 10 are negative control (no cDNA template). Lanes 1, 2, 6, and 7 are results by using cDNA templates from wild-type mice. Lanes 3, 4, 8, and 9 are results by using cDNA templates from mutant mice. Lanes 1–5 are using primer set for Ich-3 exon 4 and 6 (NOV2 and mNOp20R primer set), lanes 6–10 are using primer set for Ice exon 6 (MICE3 and MICE4 primer set).

Figure 9A:
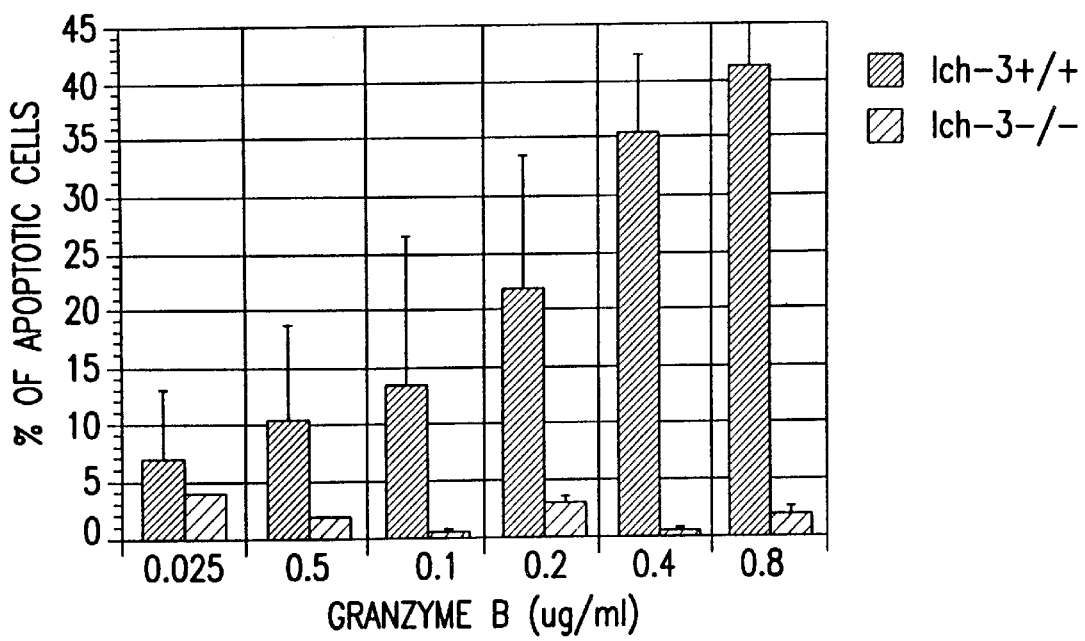
Figure 9B:
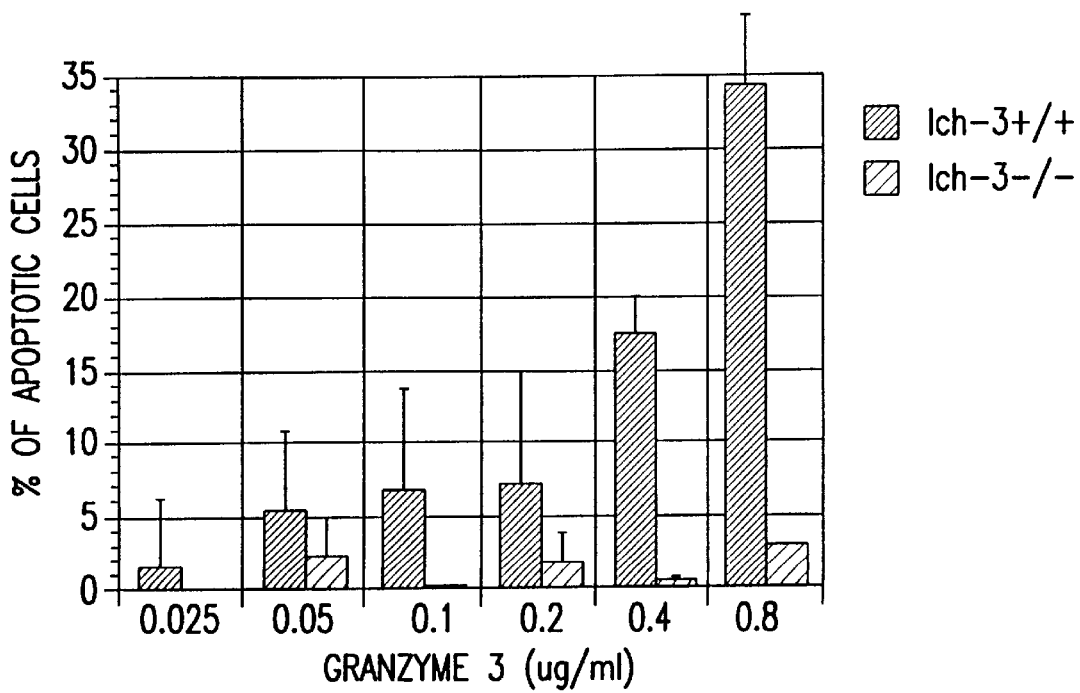

FIGS. 9A–9B. Ich-3 deficient EF cells are resistant to Granzyme B and Granzyme 3 induced apoptosis. Embryonic fibroblasts from Ich-3-/- and wild type controls were treated with varying concentrations of granzyme B (FIG. 9A) or granzyme 3 (FIG. 9B) in the presence of a constant amount of perforin (50 ng/ml) for a period of 2 and 8 hrs, respectively. The percentage of apoptosis cells was determined from cell counts after staining with Hoechst dye (Chen et al., 1995). Control wells contained cells alone incubated with or without perforin. Data points represent the percentage of apoptotic cells for a particular dilution of granzyme minus the percentage of apoptotic cells observed in medium alone.

Figure 10:
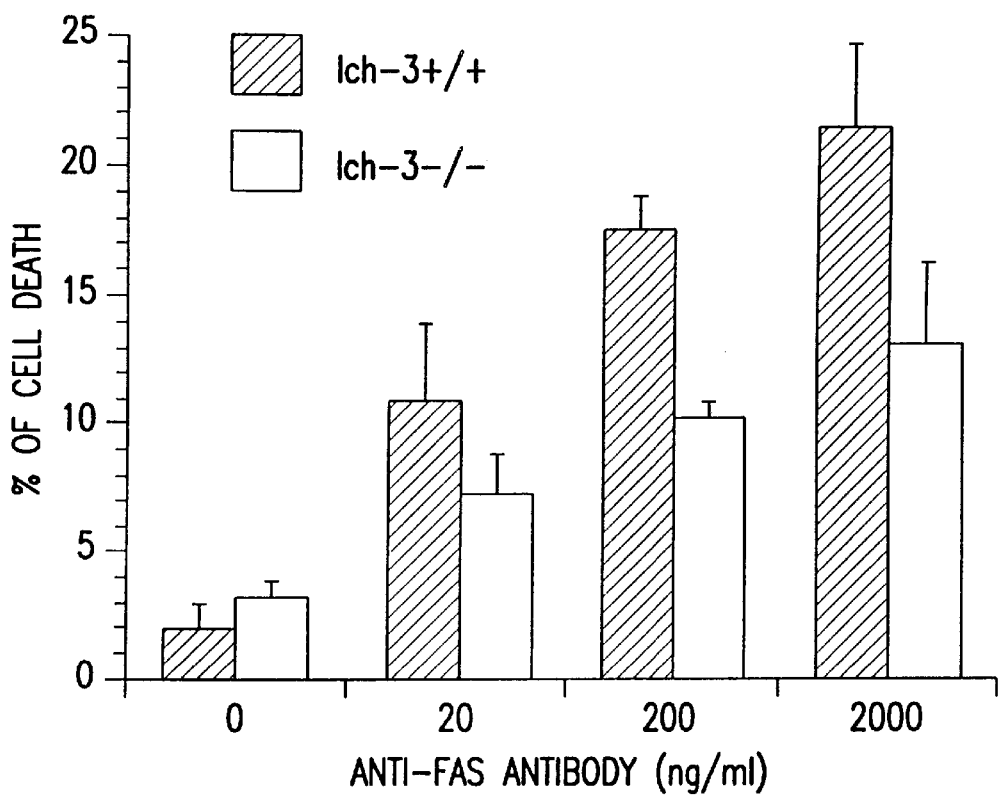

FIG. 10. Partial Resistance to Fas-Induced Thymocytes Cell Death in Ich-3-deficient mice. Freshly isolated thymocytes were incubated for 20 hr with antibody at the concentrations indicated. Cell viability was determined by trypan blue dye exclusion. Values represent the percentage dead cell from three independent wells (±S.D). Two independent experiments were performed and showed similar results.

Figure 11:
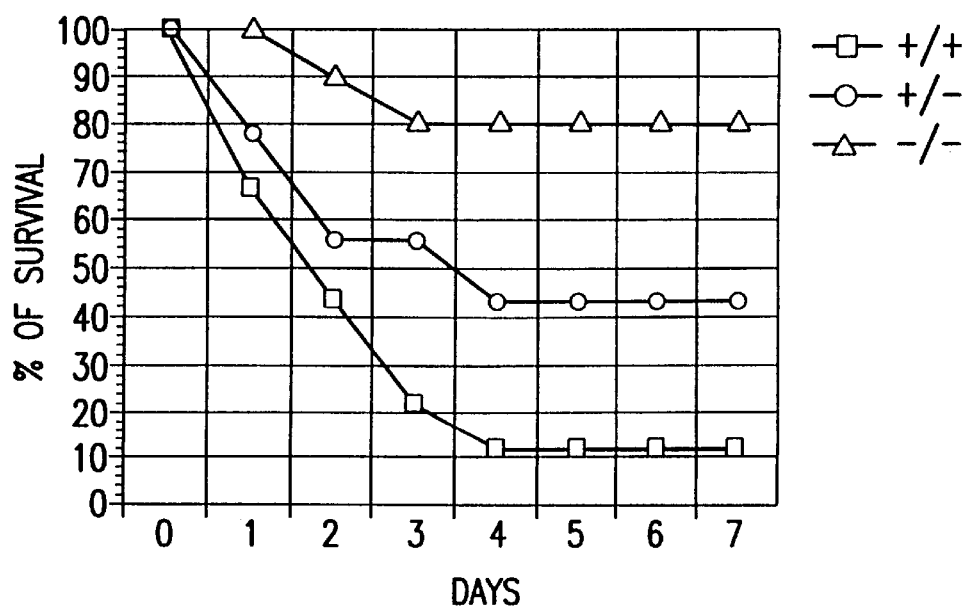

FIG. 11. Survival of Ich-3-Deficient Mice After Administration with Lethal Dose of LPS. Survival of Ich-3-deficient (-/-), heterozygous (+/-) and wild-type (+/+) mice after injection of lethal dose of LPS (40 mg LPS/kg body weight) were tested. A total of 10 Ich-3 mutant (5 males, 5 females), 9 heterozygous (8 males, 1 females), and 9 wild-type (3 males and 6 females) were tested in at least three independent experiments.

Figure 12A:
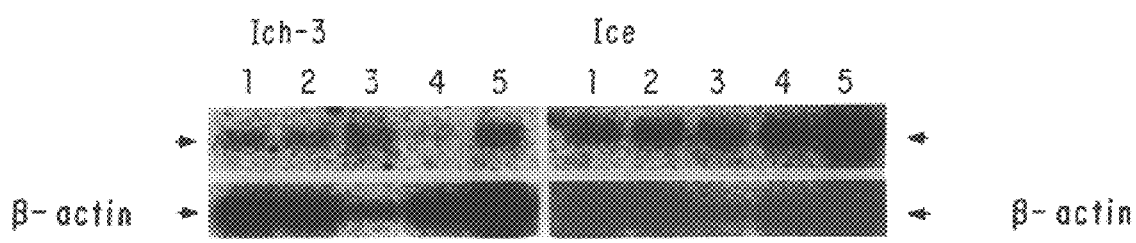
Figure 12B:
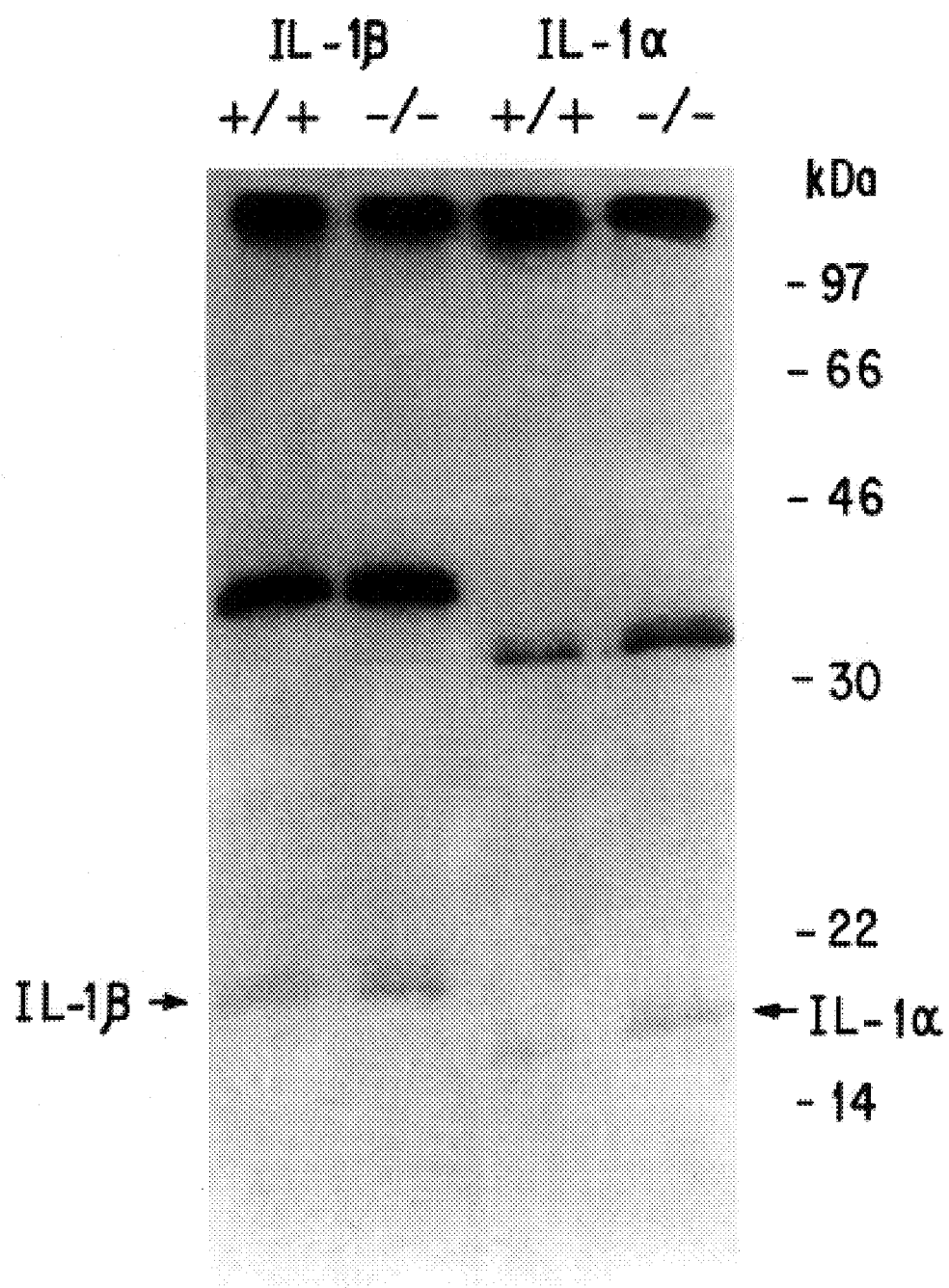

FIGS. 12A–12B. Normal Secretion of IL1 by Macrophages from Ich-3-Deficient Mice.

FIG. 12A. Northern blot analysis of Ice and Ich-3 expression in PECs and splenocytes. Northern blots were probed with Ice or Ich-3 cDNA probes as indicated. Lane 1: 2.5 (g of total RNA from splenocytes stimulated with conA (5 (g/ml) and murine IL-2 (100 u/ml) for 3 days. Lane 2: 2.5 (g of total RNA from splenocytes stimulated with conA (5 (g/ml) for 3 days. Lane 3: 2.5 (g of total RNA from freshly isolated splenocytes. Lane 4 and 5: total RNA from PECs (lane 4,2.5 (g RNA., lane 5, 10 (g total RNA).

FIG. 12B. IL-1 production by macrophages from Ich-3-deficient and wild-type mice. Peritoneal macrophages (PECs) were isolated and stimulated with LPS, and then ATP was added to induce apoptosis. [$^{35}$S]-methionine labeled cytokines in the supernatants were collected and then processed for immunoprecipitation. Antibodies used for immunoprecipitations were indicated in the figure. Genotypes were indicated as in +/+ (wild-type) and -/- (mutant).

Figure 13B:
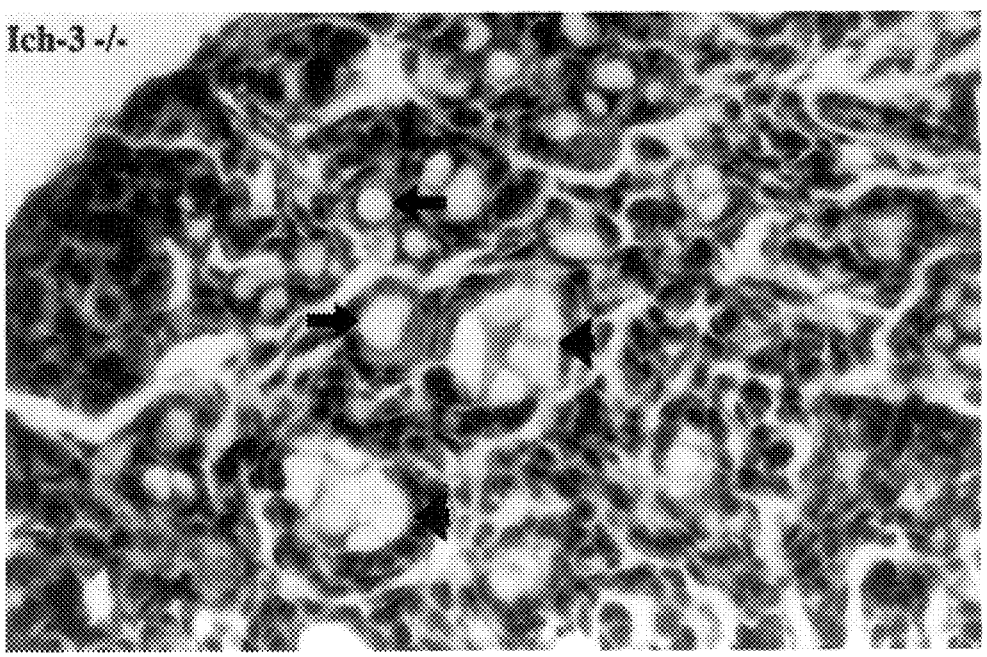
Figure 13C:
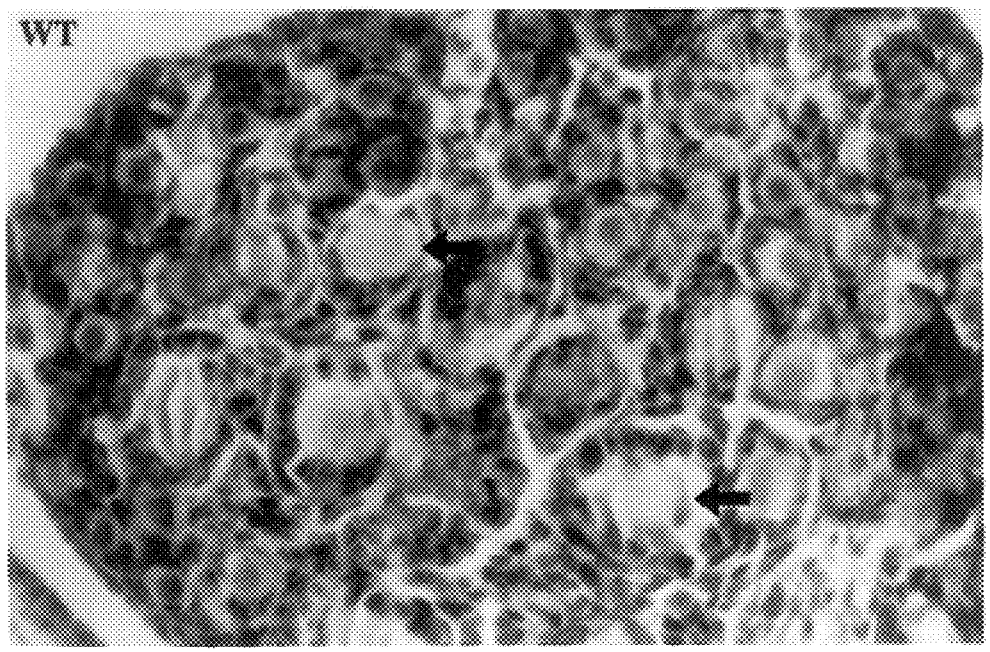

FIGS. 13A–13C. The function of Ich-3 in ovary.

FIG. 13A. Morphometric analysis of the numbers of follicles at the primordial, primary or small preantral stages of development in ovaries of wild-type (open bars) and Ich-3 deficient (batched bars) female mice at 4 days of age postpartum (N. D.=none detected). Due to the large scale differences in the numbers of follicles at different stages of development, the insert depicts an enlarged frame specifically corresponding to the primary and small preantral follicle numbers.

FIG. 13B. Representative photomicrograph granulosa cells (GC) without an oocyte (arrows), and granulosa cells with multiple oocyte-like cells (arrow heads), found only in ovaries of Ich-3 mutant mice.

FIG. 13C. Comparative photograph of ovary from a wild type mouse at day 4 post-partum. Arrows point to normal granulosa cells with an oocyte.

DETAILED DESCRIPTION OF PREFERRED EMBODIMENTS

In the description that follows, a variety of technical terms are used. Unless the context indicates otherwise, these terms shall have their ordinary well-recognized meaning in the art. In order to provide a clearer and more consistent understanding of the specification and claims, the following definitions are provided.

Italicized words such as Ice or Ich refer to the gene or the corresponding RNA, while non-italicized words such as "ICE or ICH" refers to the protein product encoded by the corresponding gene.

Apoptosis. As used herein, "apoptosis" refers to the process by which organisms eliminate unwanted cells. The process is regulated by a cellular program. Apoptosis may eliminate cells during normal development, aging, tissue homeostasis or following imposition of an external stress such as hypoxia or trophic factor deprivation.

Disrupted gene. As used herein, "disrupted gene" refers to a gene containing an insertion, substitution, or deletion resulting in the loss of substantially all of the biological activity associated with the gene. For example, a disrupted Ich-3 gene would be unable to express a protein a substantial amount of ICH-3 protein.

Endotoxic or septic shock As used herein, "endotoxic or septic shock" means shock produced by bacterial endotoxins, particularly *E. coli;* particularly with septicemia or infection with gram negative bacilli. (*Stedman's Medical Dictionary*, 22nd ed., Williams & Wilkins Co., Baltimore, 1972). Septic shock may be produced by administration of lipopolysaccharide (LPS).

Septic shock is a systemic response to infection with high mortality in human (Morrison & Ryan, *Annu. Rev. Med.* 38:417–432 (1987)). LPS and other endotoxin products of gram-positive or gram-negative bacteria induce massive systemic release of TNF-α and IL-1, which are the major mediators of pathology in sepsis. The release of these endogenous mediators leads to several characteristic pathophysiological reactions, such as fever, leukopenia, thrombocytopenia, disseminated intravascular coagulation, leukocyte infiltration in various organs, hemodynamic changes and eventual death. Some of these responses may be due to the effects of TNF-α or IL-β on vascular endothelial cells which result in cell adhesion, vascular leakage and shock. Neutralization of either TNF-α or IL-β has been shown to prevent lethality in animal models of sepsis (Dinarello, et al., *J. Am. Med. Assoc.* 269:106–113 (1993)).

Expression vector. As used herein, an "expression vector" is a vector comprising a structural gene operably linked to an expression control sequence so that the structural gene can be expressed when the expression vector is transformed into an appropriate host cell. Two DNA sequences are said to be "operably linked" if the nature of the linkage between the two DNA sequences does not (1) result in the introduction of a frame-shift mutation, (2) interfere with the ability of the promoter region sequence to direct the transcription of the desired sequence, or (3) interfere with the ability of the desired sequence to be transcribed by the promoter region sequence. Thus, a promoter region would be operably linked to a desired DNA sequence if the promoter were capable of effecting transcription of that DNA sequence.

ICE pathway. As used herein, "ICE pathway" refers to the pathway by which interleukin converting enzyme converts the pro-ILβ to IL-β eventually resulting in programmed cell death.

Modulating programmed cell death As used herein, "modulating programmed cell death" should be understood to mean that one either increases or decreases cell death depending upon the desired end result.

Resistant to. As used herein "resistant to" means that an animal exposed to a certain treatment shows a greater degree of survivability than the corresponding control (i.e. the treatment is less lethal than to the corresponding control). This does not necessarily mean that all animals will survive the treatment.

Sepsis. As used herein, "sepsis" means the presence of various pus-forming and other pathogenic organisms, or their toxins, in the blood or tissues; septicemia is a common form of sepsis. Septicemia is a systemic disease caused by the presence of microorganisms or their toxins in the circulating blood. (*Stedman's Medical Dictionary*, 22nd ed., Williams & Wilkins Co., Baltimore, 1972).

Targeting vector. As used herein "a targeting vector" is a vector comprising sequences that can be inserted into a gene to be disrupted, e.g., by homologous recombination. Therefore, a targeting vector may contain sequences homologous to the gene to be disrupted. This invention relates to non-human transgenic animals comprising a disrupted Ich-3 gene.

Transgenic. As used herein, a "transgenic organism" is an organism containing a defined change to its germ line, wherein the change is not ordinarily found in wild-type organisms. This change can be passed on to the organism's progeny. The change to the organism's germ line can be an insertion, a substitution, or a deletion. Thus, the term "transgenic" encompasses organisms where a gene has been eliminated or disrupted so as to result in the elimination of a phenotype associated with the disrupted gene ("knockout animals"). The term "transgenic" also encompasses organisms containing modifications to their existing genes and organisms modified to contain exogenous genes introduced into their germ line.

Vector. As used herein, a "vector" is a plasmid, phage, or other DNA sequence, which provides an appropriate nucleic acid environment for a transfer of a gene of interest into a host cell. The cloning vectors of this invention will ordinarily replicate autonomously in eukaryotic hosts. The cloning vector may be further characterized in terms of endonuclease restriction sites where the vector may be cut in a determinable fashion. The vector may also comprise a marker suitable for use in identifying cells transformed with the cloning vector. For example, markers can be antibiotic resistance genes.

Naturally occurring cell death acts to regulate cell number, to facilitate morphogenesis, to remove harmful or otherwise abnormal cells and to eliminate cells that have already performed their function. Additionally, programmed cell death is believed to occur in response to physiological stresses such as hypoxia or ischemia.

Acute and chronic disregulation of cell death is believed to lead to a number of major human diseases (Barr et al. *Biotech.* 12:487–493, 1995). These diseases include but are not limited to malignant and pre-malignant conditions, neurological disorder, heart disease, immune system disorders, intestinal disorders, kidney disease and aging Malignant and pre-malignant conditions may include solid tumors, B cell lymphomas, chronic lymphocytic leukemia, prostate hypertrophy, preneoplastic liver foci and resistance to chemotherapy. Neurological disorders may include stroke, Alzheimer's disease, prion-associated disorder and ataxia telangiectasia Heart disease may include ischemic cardiac damage and chemotherapy-induced myocardial suppression. Immune system disorder may include AIDS, type I diabetes, lupus erythematosus, Sjogren's syndrome and glomerulonephritis. Intestinal disorder may include dysentery, inflammatory bowel disease and radiation- and HIV-induced diarrhea. Kidney disease may include polycystic kidney disease and anemia/erythropoiesis. Specific references to these pathophysiological conditions as involving disregulated apoptosis can be found in Barr et al. Id.—Table I.

Knowing the genes and substrates involved in the ICE pathway and effects of altering or eliminating expression of apoptotic proteins such as ICE or ICH-3 leads to means for modulating (i.e. increasing or decreasing) cell death thereby altering apoptosis. A better understanding of the apoptosis pathways and specific gene products such as ICE or ICH-3 can also lead to development of assays for agents which may affect the apoptotic process. Interventions may include, inter alia, agents which affect the activities of the gene products (e.g. agents which block receptors, inhibit or stimulate enzymatic activity), modulation of the gene product using gene-directed approaches such as anti-sense oligodeoxynucleotide strategies, transcriptional regulation and gene therapy (Karp et al., *Cancer Res.* 54:653–665 (1994)). Therefore, apoptosis should be amenable to therapeutic intervention. In this regard, one may either stimulate or inhibit the process depending upon whether wants to increase or decrease the rate of programmed cell death.

Proteolytic cleavage by the ICE family may lead to apoptosis in several ways. One possibility is that cleavage of a large number of proteins destroys the entire cellular machinery. This, however, is unlikely because most proteins appear to remain intact when cells undergo apoptosis (Lazebnik et al., *Nature* 371:346–347 (1994)). The second possibility is that proteolytic cleavage of one critically important substrate leads to cell death This also is unlikely because a number of proteins, including pro-IL-1$\beta$ ribose polymerase (PARP), U1-70 kD ribonuclear protein, and nuclear lamin are cleaved during apoptosis (Miura, et al, *Proc. Natl. Acad. Sci.* 92:8318–8322 (1995); Lazebnik et al., *Nature* 371:346–347 (1994); Casciola-Rosen et al., *J. Biol. Chem.* 269:30757–30760 (1994); Lazebnik, Y. A., et al., *Proc. Natl. Acad. Sci.* 92:9042–9046 (1995)). It is not clear (with perhaps the exception of pro-IL-1$\beta$), whether products of proteins cleaved by the ICE-family mediate downstream events of cell death pathways or whether they are merely the end result of apoptosis. In contrast to pro-IL-1$\beta$, however, are the examples in the specification using ICH-3 which suggest that the Ich-3 gene encodes an upstream-regulator of ICE in vivo.

The third possibility for how proteolytic cleavage may lead to apoptosis is that activation of the ICE pathway and therefore the ICE family may result in cleavage of several substrates, some being activated (mediating cell death) and others being destroyed (required for cell survival). Activation of the pathway may occur due to events such as trophic factor deprivation, hypoxia, $G_1$/S arrest or TNF-$\alpha$ treatment. Results previously obtained lead to favoring this last hypothesis, at least as related to the Ice gene because the data indicate that endogenously-produced mature IL-1$\beta$ is directly involved in cell death and is the first identified substrate of an apoptosis-inducing gene whose product plays a direct role in mediating the apoptotic cascade. While these are proposed mechanisms for how the ICE-family may modulate apoptosis, they should in no way be construed as limiting the claims of the invention to operation by such a mechanism.

Additionally, a number of signal transduction mechanisms mediate the biological effect of IL-1$\beta$. Several of these second messengers have been implicated in apoptosis and, following ICE activation, likely mediate cell death following endogenous mature IL-1$\beta$ receptor binding. Therefore, blocking receptor binding will module apoptosis.

IL-1β induces ceramide production in EL4 thymoma cells (Mathias, S., et al., *Science* 259:519–522 (1993)). IL-1β also induces apoptosis in pancreatic Rlm5F cells via a pathway which is dependent on its ability to induce nitric oxide production (Ankarcrona et al., *Cell Res.* 213:172–177 (1994)). Both ceramide and nitric oxide are strong candidates for direct mediators of apoptosis (Ankarcrona et al., *Cell Res.* 213:172–177 (1994); Haimovitz-Friedman, A., et al., *J. Exp. Med.* 180:525–535 (1994)). A recent report showed that NGF deprivation of PC12 cells, which induces apoptosis, led to a substantial activation of the JNK and p38 MAP kinases (Xia et al., *Science* 270:1326–1331 (1995)). IL-1β has been shown to activate the JNK-p38 signaling pathway and NGF withdrawal may induce secretion of IL-1β which then activates the JNK-p38 pathway and cell death (Raingeaud, J., et al., *J. Biol. Chem.* 270:7420–7426 (1995)).

By obtaining transgenic animals in which specific genes and proteins of the apoptotic pathway are altered or eliminated (i.e. knock-out mice) a better understanding of the regulation of programmed cell death will be gained. In order to obtain a transgenic animal comprising a disrupted Ich-3 gene, a targeting vector is used. The targeting vector will generally have a 5' flanking region and a 3' flanking region homologous to segments of the gene surrounding an unrelated DNA sequence to be inserted into the Ich-3 gene. For example, the unrelated DNA sequence can encode a selectable marker, such as an antibiotic resistance gene. Specific examples of a suitable selectable marker include the neomycin resistance gene (NEO) and the hygromycin β-phosphotransferase. The 5' flanking region and the 3' flanking region are homologous to regions within the Ich-3 gene surrounding the portion of the gene to be replaced with the unrelated DNA sequence. DNA comprising the targeting vector and the native Ich-3 gene are brought together under conditions where homologous recombination is favored. For example, the targeting vector and native Ich-3 gene sequence can be used to transform embryonic stem (ES) cells, where they can subsequently undergo homologous recombination. The targeting vector pJ476, has been deposited with the A.T.C.C. (Rockville, Md.) under the terms of the Budapest Treaty under A.T.C.C. accession number 98118 on Aug. 1, 1996.

Proper homologous recombination can be tested by Southern blot analysis of restriction endonuclease digested DNA using a probe to a non-disrupted region of the Ich-3 gene. For example, Probe A, identified in FIG. 7A, can be used. Since the native Ich-3 gene will exhibit a different restriction pattern from the disrupted Ich-3gene, the presence of a disrupted Ich-3 gene can be determined from the size of the restriction fragments that hybridize to the probe.

In one method of producing the transgenic animals, transformed ES cells containing a disrupted Ich-3 gene having undergone homologous recombination, are introduced into a normal blastocyst. The blastocyst is then transferred into the uterus of a pseudo-pregnant foster mother. Pseudo-pregnant foster mothers have been mated with vasectomized males, so that they are in the proper stage of their estrus cycle and their uterus is hormonally primed to accept an embryo.

The extent of the contribution of the ES cells, containing the disrupted Ich-3 gene, to the somatic tissues of the transgenic mouse can be determined visually by choosing strains of mice for the source of the ES cells and blastocyst that have different coat colors.

The resulting homozygous Ich-3 mutant animals generated by homologous recombination are viable, fertile, and indistinguishable from wild-type and heterozygous littermates in overall appearance. These mutant animals contains essentially no full length Ich-3 transcripts and no immunoreactive ICH-3 protein as measured by western blot analysis.

The Ich-3 mutant animals of the invention can be any non-human mammal. In embodiments of this invention, the animals are mice, rats, guinea pigs, rabbits, and dogs. In an especially preferred embodiment of the invention, the Ich-3 mutant animal is a mouse.

The mutant mouse of the invention provides, inter alia, a model and/or test system for investigators to manipulate and better understand the mechanisms of apoptosis, sepsis and folliculogenesis. In particular, a better understanding is gained concerning the role of the Ich-3 gene, its protein product and possibly the ICE pathway. Such a model, allows the investigator to test various drugs where physiological responses are altered in the mouse, e.g. resistance to sepsis (increased) and thereby determine more effective therapy to address the underlying mechanism of the problem.

Therefore, invention also provides, a method of screening compounds, comprising: providing the compound to a transgenic non-human animal having a disrupted Ich-3 gene; determining the effect of the compound on apoptosis of said animal; and correlating the effect of the compound with increases or decreases in apoptosis.

The compounds to be tested can be administered to the transgenic non-human animal having a disrupted Ich-3gene in a variety of ways well known to one of ordinary skill in the art. For example, the compound can be administered by parenteral injection, such as subcutaneous, intramuscular, or intra-abdominal injection, infusion, ingestion, suppository administration, and skin-patch application. Moreover, the compound can be provided in a pharmaceutically acceptable carrier. See "Remington's Pharmaceutical Sciences" (1990). The effect of the compound on apoptosis, septic shock or folliculogenesis can be determined using methods well known to one of ordinary skill in the art.

In addition, the Ich-3 mutant animals of this invention unexpectedly exhibit an increased resistance to septic shock resulting from LPS administration The Ich-3mutant animals of this invention, therefore, are useful as an animal model to study septic shock. For example, various compounds could be tested to determine whether they further increase or decrease the resistance of Ich-3 mutant mice to septic shock.

This invention relates to Ich-3 mutant animals with defects in early folliculogenesis and germ cell endowment. Therefore, the invention provides methods for screening compounds using the Ich-3mutant animals as an animal model to identify compounds useful in treating problems related to folliculogenesis or germ cell endowment.

These aspects of the invention (i.e. those relating to the testing of compounds affecting apoptosis, septic shock, folliculogenesis and germ cell endowment) are useful to screen compounds from a variety of sources. Examples of compounds that can be screened using the method of the invention include but are not limited to rationally designed and synthetic molecules, plant extracts, animal extracts, inorganic compounds, mixtures, and solutions, as well as homogeneous molecular or elemental samples. Establishing that a compound has an effect in the Ich-3 mutant animals has predictive value relating to that compound's effect in other animals, including humans. Such predictive values provides for initial screening of therapeutically valuable drugs.

The invention, therefore, provides a method of screening compounds, comprising: providing a transgenic non-human animal having a disrupted Ich-3 gene and exhibiting the properties described in this specification, administering a compound to be tested to the transgenic animal; determining the effect of the compound on the properties of interest in said animal; and correlating the effect of the compound on the Ich-3 mutant mouse with the effect of said compound in a control animal.

Thus, the mutant animals of this invention are also useful as animal models to study apoptosis, septic shock and folliculogensis.

Having now generally described the inventions the same will be more readily understood through reference to the following examples which are provided by way of illustration, and are not intended to be limiting of the present invention.

EXAMPLES

Example 1

ICH-3 is a Member of the ICE Family

To identify additional members of the ICE family, a mouse thymus cDNA library (Strategene) was screened under low stringency conditions using human Ice cDNA as a probe. Two positive clones were identified. One of them was murine Ice cDNA and the other, named Ich-3 subsequently, encodes a protein similar but not identical to murine ICE.

Cloning and construction of plasmids

A mouse thymus cDNA library containing $10_6$ plaque-forming units was screened by human Ice cDNA as a probe. Hybridization was performed under low stringency at 40° C. overnight in 5×SSPE, 20% formamide, 10×Denhardt's solution, 1% SDS. Filters were washed in 1×SSPE, 0.5% SDS twice at room temperature, and then twice at 42° C. Two Ich-3 cDNA clones were originally obtained and subcloned into pBluescript II (named m29 and mNO). Additional Ich-3 clones were also obtained from the same cDNA library by direct screening with a Ich-3 probe and were subcloned in pBluescript II (named BSNO1, BSNO3, BSNO9 and BSNO12). These clones contain inserts with overlapping segments of the Ich-3 gene. mNO contained the longest insert (2 kb) including ATG initiation codon, however, this insert was longer than the size of Ich-3 mRNA determined by Northern blot. mNO contained an unexpected duplication of Ich-3 3' cDNA sequence at its 5' end. To confirm that the 35 bp upstream sequence from the ATG codon was derived from Ich-3 mRNA, reverse transcriptase PCR analysis was performed by using the primer set mNOF (5'-TCACAGTGCGAAAGAAC) SEQ ID NO:5 and m29P2 (5'-GGTCCACACTGAAGAAT GTCTGGAGAAGCATTTCA). SEQ ID NO:9 An amplified fragment of expected size was obtained, indicating that the entire coding region of Ich-3 had been cloned (data not shown).

To construct the Ich-3-lacZ fusion gene, full-length Ich-3 cDNA was made by PCR using M34 (CCCTCGAGCGGCCGCCATGGCTGAA AACAAACACCC) SEQ ID NO:10 and mNOR (AAGTCGACTTGCCAGGAAAGAGG TAGAAATATC). SEQ ID NO:11 LacZ SalI/BamHI fragment was isolated from pβactGal' and cloned into pBluescript (BSZ). BSZ was digested with XhoI and SalI and then ligated with Ich-3 PCR fragment which was digested with XbaI and SalI (pM23Z). NotI fragment (Ich-3-lacZ) of pM23Z was cloned into pβactSTneoB (pβactM24Z) or pcDNA3 (pCMVM26Z).

To construct mutant Ich-3 gene in which the coding region for the active cysteine residue is changed into a glycine residue, two primers containing the mutation were synthesized: NO2GA (GTGCAGGCCGGCAGAGGTGGG) SEQ ID NO:12 and NO2GB (CCCACCTCTGCCGGCCTGCAC) SEQ ID NO:13. The mutant construct pβactS6Z was made from two rounds of PCR using two pairs of primers. The first round of PCR was to generate the mutant cDNA as two half cDNA fragments. The 5' fragment from N-terminus to the mutation site was made using Ich-3 cDNA as a template and M34 (CCCTCGAGCGGCCGCCATGGCTG AAAACAAACACCC) SEQ ID NO:10 and NO2GB as primers. The 3' fragment from mutated site to C-terminus was generated using Ich-3 cDNA as template and NO2GA and mNOR (AAGTCGACTTGCCAGGAAAGAGGTAGAAATATC) SEQ ID NO:11 as primers. The PCR was performed under the following conditions: 1×Vent DNA polymerase buffer (Biolabs), 0.3 mM dNTPs, 0.5 μM each primers and 1 unit of Vent DNA polymerase (BioLabs) in a total volume of 25 μl. DNA was denatured at 94° C. for 1 min, annealed at 60° C. for 1 min and elongated at 72° C. for 1 min with 28 cycles. In the second round PCR, the mixture of 5'-fragment and 3'-fragment was used as template and M34 and mNR Fusion as primers. The product of second PCR was a complete Ich-3 cDNA with a mutation which changed the active cysteine to a glycine. The conditions of the PCR were the same as in the first round. The PCR product was inserted into EcoRV site of pBluescript II and sequenced to insure that no additional mutation was introduced during the PCR reactions. The expression construct of the mutant Ich-3 (pβactS6Z) was constructed similar to the original wild type construct.

The cDNA sequence of Ich-3 (FIG. 1) contains an open reading frame of 373 amino acids. The first ATG translational start codon is at the nucleotide 35–37. An opal stop codon is at the nucleotides 1154–1156. There is a canonical poly(A) signal (AATAAA) at its 3' non-coding region. The predicted molecular weight of ICH-3 is 42 kDa. The amino acid sequence of ICH-3 is most homologous to human TX (60% identity), which is also named as ICErelII and ICH2 (Munday, N. A., et al., *J. Biol. Chem.* 270:15870–15876 (1995); Kamens et al., *J. Biol. Chem.* 270:15250–15256 (1995)). ICH-3 shares 46%, 45% and 54% of identities with murine ICE, human ICE and human ICErelIII, respectively (Table 1). ICH-3 is less homologous to *C. elegans* Ced-3, human ICH-1$_L$, human CPP32 and human MCH2 with 26%, 30%, 32% and 24% identities, respectively. Like all the other members of the ICE family, ICH-3 also lacks an extended serine rich region that is present in Ced-3 (Yuan et al., *Cell* 75:641–752 (1993)). The majority of sequence heterogeneity occurs in the prepeptide region, whereas those areas within and around the conserved pentapeptide QACRG, the active site for the ICE family, is highly homologous. These results indicate that ICH-3 protein is a member of the ICE family.

TABLE 1

Summary of amino acid sequence identities among all the ICE/Ced-3 family members reported to date. The numbers in the table represent % of identity of the sequences compared. The human protein TX, ICE$_{rel}$II and ICH-2 are the same protein.

Percentage of amino acid sequence identity:

| | TX | mICE | hICE | relIII | CED3 | hICH1 | CPP32 | MCH2 |
|---|---|---|---|---|---|---|---|---|
| ICH-3 | 60 | 46 | 45 | 54 | 26 | 30 | 32 | 24 |
| TX/ICErelII/ICH2 | | 49 | 53 | 73 | 27 | 28 | 32 | 23 |
| mICE | | | 62 | 49 | 28 | 26 | 32 | 28 |
| hICE | | | | 50 | 29 | 27 | 30 | 27 |
| ICErel-III | | | | | 25 | 25 | 30 | 23 |
| CED-3 | | | | | | 28 | 34 | 33 |
| hICH-1 | | | | | | | 28 | 28 |
| CPP32/YAMA | | | | | | | | 46 |

ICE is synthesized as a p45 precursor form which is cleaved during activation into the p20 and p10 subunits (Thornberry, N. A., Nature 356:768–774 (1992)). The cleavage is dependent on aspartic acid residue in the P1 position. Examining the residues involved in the maturation of the ICE precursor (Thornberry, N. A., Nature 356:768–774 (1992); Walker, N. P. C., et al., Cell 78:3434–352 (1994); Wilson, K. P., et al., Nature 370:270–275 (1994)), the residue of ICH-3 corresponding to the ICE residue involved in processing p10 N-terminal is conserved, whereas the residues corresponding to the processing site for the N-terminus and C-terminus of p20 are not conserved in ICH-3 (FIG. 2). Two nearby Asp residues ($Asp_{59}$ and $Asp_{80}$) in the ICH-3 sequence may serve as potential processing sites for the N-terminus of p20, which would produce a subunit of 20 kDa.

According to the X-ray crystal structural analysis of ICE (Wilson, K. P., et al., Nature 370:270–275 (1994); Walker, N. P. C., et al., Cell 78:3434–352 (1994)), $His_{237}$, $Gly_{238}$ and $Cys_{285}$ of ICE are involved in catalysis and all three are conserved in ICH-3 ($His_{206}$, $Gly_{207}$ and $Cys_{254}$) (FIG. 2A). The residues that are part of the P1 Asp binding pocket in ICE ($Arg_{179}$, $Gln_{283}$, $Arg_{341}$ and $Ser_{347}$) are also conserved in ICH-3 ( $Arg_{148}$, $Gln_{252}$, $Arg_{310}$ and $Ser_{316}$) (FIG. 2A). However, the residues in ICE that make up the groove for binding P2–P4 residues of the substrate (ICE $Val_{338}$, $Trp_{340}$, $His_{342}$, $Pro_{343}$, $Arg_{383}$, and $Gln_{385}$) are quite different in ICH-3 and the corresponding amino acids are $Leu_{307}$, $Tyr_{309}$, $Asp_{311}$, $Lys_{312}$ and $His_{352}$ with only one $Gin_{352}$ conserved. These comparisons predict that ICH-3 is also a cysteine protease with preference for Asp at P1 position but it may recognize a slightly different set of substrates than those cleaved by ICE.

The molecular cloning and characterization of murine Ich-3, a new member of the Ice/ced-3 family is described. The predicted ICH-3 protein is 373 amino acids long and contains the 100% conserved ICE family signature peptide QACRG. Five additional members of the ICE family have been identified (Wang et al., Cell 87:739–750 (1994); Munday, N. A., et al., J. Biol. Chem. 270:1587–15876 (1995); Kamens et al., J. Biol. Chem. 270:15250–15256 (1995)). These ICE homologs can be classified into two different groups by their sequence homology: one group (ICE) is more homologous to ICE than to Ced-3 (TX/ICErelII/ICH2 and ICErelIII) and the other (Ced-3) is more homologous to Ced-3 than to ICE or equally homologous to ICE and Ced-3 (ICH-1, CPP32/Yama and MCH-2). Murine ICH-3 is more homologous to ICE than to Ced-3 and therefore belongs to the ICE group. The amino acid sequence of ICH-3 is 60% identical to TX, which is close to the identity shared by murine and human ICE (62% identity). The expression pattern of Ich-3 is also similar to TX: both are expressed in many tissues, but are expressed at very low levels in the brain. It is possible that ICH-3 is the murine equivalent of human TX. It cannot be concluded at the moment, however, that Ich-3 is in fact murine version of human TX because TX has been shown to be able to cleave pro-ICE (Faucheu et al., EMBO J. 14:1914–1922 (1995)) whereas the same thing has not been observed for ICH-3 in a similar assay.

Example 2

Ich-3 is Expressed in Many Tissues and is Induced by LPS

To study the expression pattern of Ich-3, total RNA was isolated from different tissues of mice.

Northern blot analysis and RT-PCR

Total RNA from different tissues of mouse was isolated by TRIzol total RNA Isolation (GIBCO BRL). For isolation of total RNA from mice stimulated by LPS, 7–10 weeks old mice were injected with LPS at dose of 40 mg/kg body weight and 5 hrs after LPS injection, tissues were isolated for RNA preparation. The $^{32}$P-labeled probe was the 3'-fragment of Ich-3 generated by PCR using two primers NO2GA and mNoR. Hybridization was performed overnight at 62° C. in 1% BSA, 1 mM EDTA, 0.5 M Sodium phosphate pH 7.2, and 17.5% SDS. The blots were washed in 40 mM Sodium phosphate (pH 7.2), 1 mM EDTA, 1% SDS and 70 mM NaCl at 65° C. and autoradiographed. For RT-PCR, first strand cDNA was synthesized by use of total RNA and random priming with Moloney murine leukemia virus reverse transcriptase (Gibco BRL) as described previously (Wang et al., 1994). The primers used for PCR to amplify Ich-3 were mNOF (5'-CTTCACAGTGCGAAAGAACT-3') SEQ ID NO:8 and m29P2 (5'-GGTCCACACTGAAGAATGTCTG GAGAAGCATTTCA-3'). SEQ ID NO:9 The PCR was performed under the following conditions: 1×Taq polymerase buffer (Promega), 0.3 mM dNTPs, 2.5 mM $MgCl_2$, 0.5 μM each primer, 1 unit of Taq DNA polymerase (Promega) in a total volume of 25 μl. DNA was denatured at 94° C. for 1 min, annealed at 5° C. for 1 min and elongated at 72° C. for 1 min with 30 cycles. The PCR of β actin was performed under the same conditions.

Expression and purification of ICH-3 from E. coli.

An EcoRI fragment from the cDNA clone BSNO12 encoding the full length Ich-3 was subcloned into EcoRI site of pTrcHis (Invitrogen). The construct was named as pTrcHisS9. In this construct, the N-terminal of Ich-3 was fused to a polyhistidine (six histidines) coding region and the fusion gene was placed under the control of the inducible trpB and lacUV5 hybrid promoter. The production of the fusion protein was induced by 0.3 mM IPTG and the protein was purified by His.Bind™ Buffer Kit from Novagen according to the protocol. The protein was stored at −20° C. in 10% glycerol.

Generation of ICH-3 p20 peptide antibody and Western blotting analysis

A 15 amino acid peptide (H-TEFKHLSLRYGAKFD)8-MAP-linked SEQ ID NO:7 within the p20 region of ICH-3 was used for the generation of polyclonal antibodies. Standard protocols in the art were used (Liddell, et al., *Antibody Technology*, 1995; Drenckhahn et al, *Methods in Cell Biology*, Vol. 37, 1993; Catty, D., *Practical Approach Series*, Vol. 1A, 1988; E. Herlow et al. The specificity of these antibodies was verified by Western blot analysis. In addition, an anti-ICH-3 monoclonal antibody was isolated from rats immunized with bacterially expressed ICH-3 protein using conventional protocols (Harlow et al.,).

The peptide and rabbit polycolonal antibodies against p20 region of ICH-3 were made by Research Genetics (Huntsville, Ala.) and purified using 4% N-hydroxysuccinimidyl chloro-formate-activated cross-linked beaded agarose from Sigma (H8635) according to manufacture's protocol. For Western blotting, 10 μg of purified bacterial ICH-3 fusion protein was subjected to SDS-PAGE on a 15% polyacrylamide gel. Proteins were then transferred onto Immobilon-P membrane (Millipore, Bedford, Mass.) and incubated with 1 μg/ml rabbit anti-ICH-3 p20 polycolonal antibody for 2 hours at room temperature. After three washes with TBST (10 mM Tris pH 8.0, 0.15 M NaCl, 0.05% Tween 20), the membrane was incubated with horseradish peroxidase linked anti-rabbit Ig antibody for 45 min at room temperature (Amersham, Buckinghamshire, England). After washing three times, antibodies bound to the membrane were revealed with the ECL Western blotting reagent (Amersham, Buckinghamshire, England).

To determine induction of ICH-3 by LPS, proteins were isolated from tissues of 7–10 week old mice before injection or 4 and 20 hours after LPS injection (40 mg/kg). 60 μg of proteins were loaded in each lane on a 12% polyacrylamide gel for SDS-PAGE. After transferring the proteins onto Immobilon-P membrane, Western blotting was carried out as described above by using rat-anti mouse ICH-3 monoclonal antibodies.

Northern blots were probed with an Ich-3 cDNA probe (from the active site to 3'-end) in high stringency conditions where the hybridization mixture contained 17.5% SDS. Under the conditions only sequences with more than 95% identity would hybridize. (see above—"Northern blot analysis"). The Ich-3 probe hybridizes to a single band of 1.4 kb mRNA which is very similar to the sizes of Ice mRNA and the reported size of TX/ICErelII/ICH2 (FIG. 3A–3B). The expression pattern of Ich-3 is very similar to that of Ice, except that brain where Ice expression can be detected but Ich-3 is not. Ich-3 expression can be detected in adult heart, lung, thymus, spleen, kidney. Higher levels of Ich-3 is found in adult thymus and spleen, which is similar to the distribution of TX/ICH-2/ICE$_{rel}$II mRNA (Faucheu et al., *EMBO J*. 14:1914–1922 (1995); Kamens et al., *J. Biol. Chem*. 270:15250–15256 (1995); Munday, N. A., et al., *J. Biol. Chem* 270:15870–15876 (1995)). Only RT-PCR can detect low levels of expression in brain (FIG. 3B).

The expression levels of Ich-3 in wild type mice in control conditions are very low. Endotoxins (lipopolysaccharide, LPS) are strong inducers of proIL-1β synthesis and mature IL-1β secretion. To examine if the expression of Ich-3 can be induced by LPS, RNA was prepared from mice either before injection or 5 hrs after injection of lethal dose LPS (40 mg/kg of body weight). Northern blot analysis showed that Ich-3 RNA expression was dramatically induced at least 30 fold after LPS stimulation in thymus, lung, spleen and kidney but not brain where Ich-3 expression is low in control mice (FIG. 3A). Ice transcription was not induced in spleen, kidney, lung, heart and brain after LPS stimulation. Ice mRNA was only induced significantly in thymus FIG. 3A).

The levels of ICH-3 protein before and after LPS stimulation were also investigated. Proteins were isolated from tissues of 7–10 weeks old mice before injection and 4 hrs or 20 hrs after LPS stimulation (40 mg/kg) and then analyzed on western blot using a monoclonal antibody which recognizes ICH-3 specifically. ICH-3 protein was undetectable in western blot of tissues isolated from control mice. In LPS stimulated mice, ICH-3 was detected as two proteins of 43 kDa and 38 kDa 43 kDa is very close to the predicted protein size from the full length Ich-3 cDNA. It is known that these proteins are from the Ich-3 locus because the Ich-3−/− knockout mice that have been generated using gene targeting techniques are specifically missing these two proteins. LPS stimulation resulted in at least 20–30 fold increase in levels of ICH-3 proteins. In the spleen, two additional bands of 30 kDa and 26 kDa were detected which may be cleavage products of 43 kDa or 38 kDa Elevated levels of ICH-3 proteins were found at both 4 hrs and 20 hrs after LPS stimulation, suggesting that LPS induced an immediate and sustained increase in levels of ICH-3 proteins. In contrast, western blot analysis of the same tissue samples using a polyclonal anti-ICE antibody detected no difference in expression before and after LPS stimulation (data not shown). These results suggest that Ich-3 may be an important regulator of endotoxic shock in mice.

Example 3

Overexpression of Ich-3 Induces Apoptosis

To examine whether expression of Ich-3 may be able to induce apoptosis, the same transient expression system used for Ice and Ich-1 (Miura et al., *Cell* 75:653–660 (1993); Wang et al., *Cell* 87:739–750 (1994)) was used. The mouse Ich-3 cDNA was fused with the *E. coli* lacZ gene and the fused gene was placed under the control of either a chicken β-actin promoter (pβactM24Z) or CMV promoter (pCMVM26Z). A mutant Ich-3 was generated by site-directed mutagenesis in which the Cys residue in the conserved pentapeptide QACRG domain was converted to a Gly residue. This mutant was also fused to the lacZ gene and placed under the control of chicken β-actin promoter and named pβactS6Z. These expression constructs were transfected into different culture cells and their ability to induce apoptosis was tested by determining the ratio of round dead blue cells to flat live blue cells.

Cell culture and transfection studies

Rat-1 cells, HeLa cells and COS cells were maintained in Dulbecco's Modified Eagle's Medium (DMEM) supplemented with 10% fetal calf serum (FCS). For transfection, cells were seeded at a density of about $2.5 \times 10^5$ in each of the 6-well dishes. 1 μg of expression construct and 3 μl of lipofectamine reagent were used according to the protocol from GIBCO BRL. The expression of lacZ fusion genes in cell cultures was detected by X-gal staining as previously described (Miura et al., 1993). For cotransfections using more than one construct, a CaCl$_2$ transfection method was used.

Briefly, for each 6 well dish, 1–5 μg of DNA was mixed with 108 μL of water and 15.5 μl of 2M CaCl$_2$. Then the DNA-CaCl$_2$ mixture was added slowly into 125 μl of 2×HBS(280 mM Nalco, 10 mM KCl, 1.5 mM Na$_2$HPO$_4$.2H$_2$O, 12 mM dextrose and 50 mM HEPES, pH7.2). After incubation at room temperature for 20–30 min, the DNA-CaCl$_2$ mixture was added into the dish and incubated at 37° C. for 3–5 hours. The cells were shocked by 15% Glycerol in 1×HBS for 1 min and then grown in complete medium until harvesting.

As shown in FIGS. 4A–4D and Table 2, induction of Rat-1 cell apoptosis by Ich-3 is as efficient as Ice (both at about 97%). Thus, Ich-3 clearly modulates programmed cell death. The percentage of cell death induced by Ich-3-lacZ under control of the chicken β actin promoter (pβactM24Z) is similar to that of the CMV promoter (pCMV26Z). Ich-3 is less effective in inducing HeLa cell apoptosis (43%) than that of Ice (94%). Since Rat-1 cells are not transformed whereas HeLa cells are of tumor origin, this result suggests that Ich-3 induced apoptosis may be more sensitive to apoptosis suppressors than that of Ice. Consistent with this hypothesis, bcl-2 is somewhat more effective in suppressing Ich-3 induced cell death than that of Ice (Table 2).

blue cells were counted. As shown in Table 2, Ich-3 induced only 55% cell death in rat-1/crmA cells compared with 97% cell death in Rat-1 cells. Similar inhibition of cell death was observed in Ice induced cell death which is reduced from 97% to 57%. These experiments showed that CrmA is as effective in suppressing Ich-3 induced cell death as that of Ice.

Example 4

ICH-3 Can be Cleaved by Granzyme B In Vitro

Recent studies suggest that Ice may be involved in GraB/perforin mediated Cytotoxic T lymphocytes (CTL) induced apoptosis. CTLs induce apoptosis via granzymes in the presence of the pore forming protein perforin (Shi et al., *J. Exp. Med.* 175:553–566 (1992a); Shi et al., *J. Exp. Med.* 176:1521–1529 (1992b)). It has been shown that ICE cannot be cleaved directly by GraB; nevertheless, ICE is important for GraB induced apoptosis in at least certain cell types (Shi et al., *Proc. Natl. Acad Sci.* (In press, 1996) Other ICE family members may be processed by GraB, which in turn may directly or indirectly activate ICE. ICH-3 cleavage by GraB was examined.

In vitro cleavage assay

For in vitro cleavage of ICH-3 by GraB, 10 mg purified His-tagged ICH-3 protein was incubated with 20 ng of GraB

TABLE 2

Overexpression of Ich-3 in tissue culture cells induces apoptosis. The constructs β-gal control (=pβactGal vector), Ice-lacZ(Ice-lacZ fusion under β-actin promoter control = pβactM10Z), Ich-3-lacZ (Ich-3-lacZ fusion under CMV promoter control = pCMVM26Z), and mutant Ich-3 (=pβactS6Z, mutant Ich-3 under β-actin promoter control) were transiently transfected in to different cell lines. 24 hours (40 hours in COS cells) after transfection, the cells were fixed and stained for X-Gal. The data (mean ± SEM) are the precentage of round blue cells among total number of blue cells counted. The numbers in the parentheses are the number of blue cells counted. The data were from at least three independent experiments. ND, not determined.

| | % of Cell Death | | | | |
|---|---|---|---|---|---|
| Constructs | Rat-1 | Hela | COS | Rat-1/bcl-2 | Rat-1/crmA |
| Vector alone | 3.6 ± 0.5 (946) | 9.0 ± 2.6 (768) | 4.3 ± 1.9 (428) | 3.0 ± 0.6 (987) | 7.33 ± 2.3 (870) |
| Ice-lacZ | 97.7 ± 3.4 (746) | 93.9 ± 0.3 (982) | 11 ± 0.2 (1084) | 69 ± 19 (81) | 56.5 ± 3.4 (272) |
| Ich-3-lacZ | 97.2 ± 4.2 (751) | 43.5 ± 5.5 (220) | 12.1 ± 2.1 (548) | 53.7 ± 11 (446) | 55 ± 14 (618) |
| mut. Ich-3-lacZ | 10.2 ± 2.8 (654) | ND | 5.2 ± 2.8 (492) | ND | ND |

The cowpox virus gene crmA encodes a serpin that is a specific inhibitor of ICE (Ray, C. A., et al., *Cell* 69:597–604 (1992)). CrmA is much more effective in inhibiting ICE induced apoptosis than ICH-1$_L$ induced apoptosis (Wang et al., *Cell* 87:739–750 (1994)). CrmA is 10$^4$ fold more potent in inhibiting ICE than CPP32 (Nicholson, D. W., et al., *Nature* 376:37–43 (1995)). These results suggest that CrmA can discriminate among different members of the ICE family. Since expression of crmA can suppress trophic factor deprivation induced neuronal cell death (Gagliardini et al., *Science* 263:826–828 (1994)), CTL, Fas and TNFα induced apoptosis (Tewari et al., *Chem.* 270:22605–22708 (1995a); Talley, A. K., et al., *Mol. Cell. Biol.* 15:2359–2366 (1995); Enari et al., *Nature* 375:78–81 (1995); Los et al., *Nature* 375:81–83 (1995); Miura et al., *Proc. Natl. Acad Sci. U.S.A.* 92:8318–8322(1995)), it became important to examine whether cell death induced by a particular ICE family member can be suppressed by CrmA. Expression constructs of Ice and Ich-3 were transiently transfected into Rat-1 cells stably expressing crmA (Miura et al., *Cell* 75:653–660 (1993)) and percentage of round dead blue cells among total in the presence of 50 mM Tris-HCl, pH 7.5, 0.5 mM EDTA, 0.5 mM Sucrose and 10 mM DTT in a total volume of 10 μl. The mixture was incubated at 30° C. for 1 hour and the cleavage was detected by Western blotting with a peptide antibody against the p20 portion of ICH-3.

To examine whether GraB can cleave ICH-3, a His-tagged ICH-3 protein was expressed in *E. coli*. His-tagged ICH-3 protein purified from bacteria was mixed with or without active GraB and incubated at 30° C. for 1 hour. The cleavage products were identified by Western blot with a peptide antibodies against the p20 or a monoclonal antibody against p10 portion of ICH-3. As show in FIG. 5A–5B, the full length ICH-3 band disappeared after incubation with GraB: a new 20 kDa band appeared which is detected by an anti-ICH-3 p20 antibody and a new 10 kDa band which is recognized by a monoclonal antibody against p10 of ICH-3. The ICH-3 protein purified from bacteria is processed into p30 (perhaps by autocleavage) but not p20 and p10, whereas GraB can cleave ICH-3 into p20 and p10. Fragments around 30 kDa are the predicted sizes of the cleavages at Asp 59 and Asp 80. An additional cleavage at Asp281 will generate a 20 kDa and a 10 kDa subunit. To confirm that p10 and p20 are generated from predicted p30 region, a T7-tagged p30 Ich-3 was expressed in E. coli. Cleavage of this T7-tagged p30 generated predicted p20 and p10 subunits recognized by p20 and p10 specific antibody. The cleavage of ICH-3 by GraB suggests a possible role for ICH-3 in granzyme B/perforin induced apoptosis.

Example 5

ICH-3 Does Not Process proIL-1β Directly But Can Potentiate ICE For Cleavage of proIL-1β

Mice with a homozygously disrupted Ice genes are severely defective in generating mature IL-1β (Li et al., Cell 80:401–411 (1995)); hence, ICE plays a critical role in processing pro-IL-1β to mature IL-1β. Since both mature IL-1β and Ich-3 mRNA can be dramatically induced by LPS in vivo, it is hypothesized that ICH-3 may directly or indirectly contribute to proIL-1β processing. A transient transfection assay combined with enzyme-linked immuno-absorbent assay (ELISA) was used to test the ability of ICH-3 in cleaving proIL-1β.

Assay of proIL-1β secretion

An EcoRI fragment of mouse proIL-1β cDNA was cloned into pcDNA3 and placed under control of CMV promoter. The construct was named pCMVS11. To test whether ICH-3 can process proIL-1β, pCMVS11 was cotransfected with Ich-3-LacZ fusion construct pCMVM26Z into COS cells. proIL-1β(pCMVS11) was also cotransfected with Ice-lacZ fusion construct and with vector (pβactGal). Vector DNA was added to each transfection to equalize the total amount of transfected DNA. 24 hours after transfection, supernatant was collected and stored at −80° C. or used immediately for ELISA according to the manufacture's protocol (Genzyme, Cambridge, Mass.). In some experiments the cells were stained by X-Gal as previously described (Miura et al., 1993) to test the efficiency of the transfection.

A mouse proIL-1β expression construct pCMVS11 was cotransfected into COS cells together with either Ice (pβactM10Z) or Ich-3 (pCMVM26Z) expression constructs. 24 hours after transfection, secretion of mature IL-1β into the culture medium was quantified by an ELISA assay (Genzyme, Cambridge, Mass.). As shown in FIG. 6, cotransfection of Ice with proIL-1β resulted in a significant amount of secretion of mature IL-1β. The amount of mature IL-1β generated by ICE which ranges from 70 pg/ml to 600 pg/ml is proportional to the amount of proIL-1β and Ice used in the transfection. In contrast, when Ich-3 was cotransfected with proIL-1β, no significant secretion of mature IL-1β was observed, indicating that ICH-3 could not process pro-IL-1β by itself. Cotransfection of expression vectors of both Ice and Ich-3 with that of mouse proIL-1β into COS cells resulted in a 50% increase in the amount of mature IL-1β secretion compared to Ice alone. Thus, ICH-3 can promote processing of proIL-1β by ICE. There was no increase of mature IL-1β production when Ice was cotransfected with vector (pβactGal) or mutant Ich-3 (pβactS6Z)(FIG. 6), suggesting that ICH-3 enzyme activity is required for promoting ICE function in generating mature IL-1β in vivo.

Expression of Ich-3 mRNA is low in normal healthy tissues. The levels of ICH-3 proteins are generally undetectable on western blots of tissues from healthy mice. LPS stimulation dramatically induces Ich-3 mRNA and proteins, which persists at least 20 hrs post LPS stimulation. In contrast, expression of Ice is not elevated in most tissues after LPS stimulation with the exception of thymus where its level is moderately elevated. ICH-3 protein is undetectable in normal condition in mice. Upon stimulation by LPS, two proteins of 43 kDa and 38 kDa are detected. Both proteins are products of Ich-3 gene because a null mutation in Ich-3 locus eliminates both proteins (Miura et al., Submitted (1996)). 43 kDa is very close to the predicted protein size (42 kDa) which would be generated from full length Ich-3 cDNA. The 38 kDa protein may be an alternatively spliced product of Ich-3. These results suggest that ICH-3 may play a very important role in inflammatory responses.

Consistent with its role in inflammatory responses, mice with a homozygous null mutation in Ich-3 gene are resistant to LPS induced septic shock (See Example 10 and FIG. 11). ICH-3 proteins, however, are not likely to be directly involved in processing of pro-IL-1β for the following two reasons. First, there is no in vivo evidence of existence of another protease playing a significant role in pro-IL1β processing since ICE knock-out mice are at least 90% defective in processing pro-IL-1β (Li et al., Cell 80:401–411 (1995); Kuide et al., Science 267:2000–2002 (1995)). Second, expression of Ich-3 in COS cells does not lead to pro-IL-1β processing directly; rather it promotes processing of pro-IL-1β by ICE. This result suggests that ICH-3 is an upstream regulator of ICE.

It is not clear, however, how ICH-3 activates ICE. The simplest possibility that ICH-3 directly cleaves ICE to activate it may not be true since the cleavage of pro-ICE by ICH-3 either in enzymatic assay using GraB activated ICH-3 or in cells by double transfection has consistently failed to be observed. It is hypothesized that there may be one or more intermediate steps between ICH-3 and ICE. Expression of Ich-3 in COS cells may activate this intermediate step(s) which in turn activates ICE. This may also explain only a 50% increase in mature IL-1β production is observed when both Ice and Ich-3 was coexpressed—because there is an intermediate step(s) involving a protein which is present in limited quantities in COS cells. This intermediate step may be controlled by another member of the ICE family. Alternatively, ICH-3 may activate ICE indirectly by inactivating an ICE inhibitor.

A question was also raised whether the role of ICE is primarily in inflammation or apoptosis (Li et al., Cell 80:401–411 (1995)). It is clear now that ICE has functions in both processes since Ice−/− cells are defective in both production of mature IL-1β, and Fas and GraB induced apoptosis (Li et al., Cell 80:401–411 (1995); Kuida et al., Science 267:2000–2002 (1995); Shi et al., Submitted (1996)). The same question can be asked for Ich-3: expressing Ich-3 can induce apoptosis which indicates that Ich-3 has the ability to induce apoptosis which does not prove that it has a role in inducing cell death in vivo. Ich-3−/− thymocytes are partially resistant to Fas induced apoptosis and Ich-3−/− EF cells are resistant to GraB induced apoptosis. These in vivo data are consistent with the in vitro data present here, that all suggest ICH-3 is an upstream regulator of ICE.

Like Ice−/− mice, a lethal dose of LPS fails to induce production of IL1 in the sera of Ich-3−/− mice. The critical difference, however, is that Ich-3 deficient macrophages and monocytes in vitro can produce mature IL-1β as well as wild type cells when stimulated with LPS and ATP (for macrophages) or LPS alone (for monocytes); thus, Ich-3 mutant cells still have the normal ICE function, whereas Ice deficient macrophages and monocytes do not produce mature IL-1 when stimulated in vitro (Li et al., Cell 80:401–411 (1995)). These results suggest that ICH-3 may also be an upstream regulator of ICE in vivo. When mice are stimulated with LPS, ICH-3 may be induced first and activated which in turn indirectly activates ICE. This hypothesis is entirely consistent with the data presented here: ICH-3 does not process proIL-1β directly but does promote proIL-1β processing when ICE is present. The requirement for ICH-3 is bypassed in vitro, however, when cells are stimulated with a strong signal.

Summary of examples 1–5.

The predicted amino acid sequence of ICH-3 exhibits 46% identity with murine ICE, 45% identity with human ICE, 60% and 54% identities with human ICE-like proteases TX (TX, ICE$_{rel}$-II and ICH-2 are the same protein) and ICE$_{rel}$-III, respectively. It shares 26–32% sequence identity with CED-3, human ICH-1$_L$ and CPP32/YAMA. Overexpression of Ich-3 in Rat-1 and HeLa cells induces apoptosis which can be inhibited by CrmA and Bcl-2. Expression of Ich-3 is dramatically elevated in vivo after stimulation of lipopolysaccharide (LPS), an endotoxin secreted by gram-negative bacteria which induces sepsis. In addition, ICH-3 can be cleaved by granule serine protease granzyme B in vitro. ICH-3 does not process proIL-1β directly but promotes processing of proIL-1β by ICE. These results suggest that Ich-3 may play an important role in apoptosis and inflammatory responses and may be an upstream regulator of ICE.

Example 6

Generation of a Null Mutation in the Ich-3 Gene in Mice

To obtain the genomic clone of the Ich-3 locus, a mouse 129/Sv genomic library using Ich-3 cDNA as a probe (See Example 1 and FIG. 1) was screened as follows.

Construction of the Ich-3 targeting vector

A full length Ich-3 cDNA was used to screen a lambda dash mouse genomic library of 129/Sv stain (Stratagene). To confirm the identities of genomic clones, phage DNA was digested with SalI and the genomic fragment was subcloned into pBluescript and analyzed by Southern blots and DNA sequencing. One of the subclones named BSMNO which contains all the coding exons of Ich-3 was used to construct the targeting vector.

A genomic 3.5 kb EcoRI fragment which contains the exon encoding the QACRG active site, was subcloned into pBluescript (pJ453). A 8 kb EcoRI fragment near 3' of Ich-3 gene was subcloned into pBluescript (pJ451). A poly-adenylated neomycin resistance gene under the control of phosphoglycerokinase gene promoter (pGKneo) was inserted between a 2.2 kb EoRI/AccI fragment of pJ453 and a 8 kb EcoRI fragment of pJ451, and thymidine kinase (tk) gene was ligated with 3' end of the 8 kb EcoRI fragment. The resulting targeting vector contained 2 kb of genomic DNA from the Ich-3 gene before the PGKneo insertion and 8 kb of genomic DNA downstream from PGKneo and was named pJ476.

A 1.5 kb piece of Ich-3 genomic sequence including the region coding for the active site QACRG was replaced with PGKneo in this targeting vector. To clone the 5' portion of the Ich-3 genome, the λFIX 129/Sv strain genomic library (Stratagene) was screened using an EcoRI/HindIII 0.3 kb fragment of Ich-3 cDNA (BSNO12) which contains exon 2 and 3 of Ich-3 as a probe. Four different genomic phage DNAs were subcloned into pBluescript (named BSNO3G, BSNO6G, BSNO11G, BSNO22G). From BSNO3G, a 3 kb EcoRI fragment which contains exon 2 and introns surrounding exon 2 was subcloned. A 1.9 kb fragment of exon 2 and the 5' intron was obtained by PCR using the primer set of T3 and m29P2 (5'-TCCACACTGAA GAATGTCTGG AGAAGCATTTCA) SEQ ID NO:9 and was used as a probe for genomic Southern blot. This probe detects a 10 kb and 8.7 kb BamHI fragment in wild type and mutant mice, respectively. The same BamHI fragment could be detected by using an internal probe (3.5 kb EcoRI fragment of pJ451, described as probe A in FIG. 7A).

Determination of intron/exon boundary

Various primers were used for sequencing the genomic clone (BSMNO) to determine the position of intron/exon boundary. PCR was performed to determine the length of intron. Primers used for this study were as follows: for exon 2: m29P2 (5'-GGTCCACACTGAAGAATGTCTGGAGAAGCATTTCA) SEQ ID NO:9; for exon 3: NO3 (5'-CCAGAAGAATCATTGAACAC), SEQ ID NO:14 mNO15 (5'-GAGAGTGTTCAATGA); SEQ ID NO:15 for exon 4: NOV1 (5'-GCTGTAAGCTCCTCTTTCAC), SEQ ID NO:16 NOV2 (5'-AAACATCTCTC ACTGAGGTATGGGGCTAAATTT) SEQ ID NO:17; for exon 5: NO1 (5'-ACTCTCAGAA CACCAGACATC) SEQ ID NO:18, NO2 (5'-CCCACCTCTGCAGGCCTGCAC); SEQ ID NO:19 for exon 6: NOp10 (5'-GCTGTCAAGCTGAGCC), SEQ ID NO:20 mNOp20R (5'-TCAGCTTCCATATTCCATGG); SEQ ID NO:21 for exon 7: M38 (5'-ATCACTTGTCCTACCGA); SEQ ID NO:22 for exon 8: M50 (5'-GGCAAGTAT TCATTCCC), SEQ ID NO:23 NO4 (5'-GATCAATGGTGGGCATCTGGGAA) SEQ ID NO:24 and mNORFusion (5'-TTGCCAGGAAAGAGGTAGAAAT) SEQ ID NO:25.

Screening of ES cells

J1-ES cells were maintained on feeder layers of mouse embryonic fibroblasts in the presence of 500 U/ml of leukemia inhibitory factor (GibcoBRL, Grand Island, N.Y.). ES cells were transfected with 15 µg linearized pJ476 by electroporation (400V, 25 µF, Gene Pulser, Bio-Rad, Hercules, Calif.). Thirty-six hrs after transfection, G418 (200 µg/ml of active form) was added to the medium and then 1 day later, 0.2 µM of FIAU (1-[2-deoxy, 2-fluoro-β-D-arabinofuranosyl]-5-iodouracil. Bristol-Myers Squibb Pharmaceutical Res., Seattle, Wash.) was added to the medium. Resistant colonies were picked from day 10–12 after transfection, and expanded. DNA from each resistant colony was isolated and subjected to Southern blot analysis to identify clones that underwent homologous recombination. DNA was extracted according the method by Laird (1991), and digested with BamHI, and analyzed by Southern blot analysis probed with 3.5 kb EcoRI fragment of pJ453 (probe A in FIG. 7A).

Production of chimeric and mutant mice

C57BL/6J blastocytes were microinjected with 10–12 J1 cells from a single targeted clone and implanted into pseudopregnant foster females. Techniques for microinjection are readily known to those of skill in the art and descriptions of the same can be readily found in Hogan et al., (*Manipulating the Mouse Embryo*, 2d ed., cold Spring Harbor Press, 1994). Chimeric male progeny with >60% agouti coat color were mated with C57BL/6J×DBA2 F1 female, and their progeny were screened by Southern blot analysis with the probe described above for transmission of the targeted allele.

Ich-3 is a single-copy gene with at least 8 exons (FIG. 7A). Exon 1 only encodes 3 amino acids including the initiation codon ATG for Met. The active site pentapeptide QACRG is encoded in the exon 5. A replacement-type targeting vector was constructed for selecting homologous recombination events in Ich-3 locus (FIG. 7A). In this construct, a 1.5 kb Ich-3 genomic DNA fragment containing the coding region for the active site QACRG pentapeptide was replaced with the neomycin phosphotransferase (neo) gene. This insertion/substitution resulted in deletion of 16 amino acids from the coding region of Ich-3 in exon 5 including the QACRG active site.

The Ich-3 targeting vector was transfected into J1 ES cells by electroporation and ES cells were enriched for homologous recombinants by selecting in G418 and FIAU. Correctly targeted Ich-3 mutant alleles were screened among G418/FIAU resistant ES cell clones by Southern blot analysis using an internal probe (probe A) (FIG. 7B). Probe A detected a 10 kb endogenous BamHI fragment in wild type cells whereas in cells with a homologous recombination event in one Ich-3 locus it detects a 8.7 kb and a 10 kb BamHI fragments. If the targeting vector is randomly inserted in the ES cell genome, a 2.7 kb band is detected, in addition to the endogenous 10 kb BamHI band. An external probe which encompassed a 2 kb genomic DNA fragment including exon 2 was also used to confirm the homologous recombinants on additional Southern blots (data not shown). All confirmed clones were also probed with neo gene to ensure that there is only a single integration event (data not shown). The frequency of correctly targeted clones was 16 out of 719 G418/FIAU doubly-resistant colonies. Three clones (clones 282, 444, 531) were expanded for injection of C57BL/6J blastocysts.

All three clones gave rise to highly chimeric males that were then mated with C57BL/6J×DBA2 F1 females to obtain germline transmission of the mutant alleles. Chimera of clone 444 produced germline transmitted mutant mice and the offsprings from clone 444 chimera were used for further studies. About 50% of the offspring with agouti coat color derived from mating chimeras with C57BL/6J mice were heterozygous as determined by Southern blot analysis. Heteroygous mice were crossed and genotypes were determined by Southern blot (FIG. 7C). Of the progeny from such crosses, 30% of the mice were homozygous for the mutant allele, 23% were wild-type, and 47% were heterozygous as determined by Southern blot analysis of tail DNA (total number of mice tested: 661). Thus, segregation of the mutant Ich-3 allele was close to Mendelian ratio.

The litter size from homozygous Ich-3 deficient male and female mice mating was the same as heterozygous crosses with a 1:1 male and female ratio (Data not shown). These results suggested that mutation of the Ich-3 locus did not cause any gross abnormalities of general health and reproduction of mice.

Example 7

Ich-3 Mutant Mice do not Express Wild Type Ich-3 mRNA or Protein but Express Normal Amount of Ice Transcripts To examine whether the Ich-3 mutant mice express Ich-3, total RNA was isolated from wild type and mutant mice. Northern blotting and RT-PCR Total RNA was extracted from various organs of the mice by using TRIZOL reagent (GibcoBRL, Gaithersburg, Md.) according to the manufacture's protocol. The Northern blots were probed using murine Ice or Ich-3 using conditions of 1% BSA, 1 mM EDTA, 0.5 M sodium phosphate pH 7.2 and 7% SDS at 62° C. overnight. The blots were washed twice in 40 mM sodium phosphate pH 7.2, 1 mM EDTA, 1% SDS and 70 mM NaCl at 62° C. for 20 min each. Poly(A)$^+$RNA was isolated from total RNA using standard oligo(dT) column chromatography (Sambrook et al. *Molecular Cloning: A Laboratory Manual*, Second Edition Cold Spring Harbor, N.Y.: Cold Spring Harbor Laboratory Press, (1989)). For reverse transcription PCR, first strand cDNA was synthesized through the use of random priming with Moloney murine leukemia virus reverse transcriptase (GibcoBRL, Gaithersburg, Md.). The primers used for PCR to amplify Ich-3 were NOV2, mNOp20R, mNOF (5'-CTTCACAGTGCGAAAGAACT), and m29P2. The primers used to amplify Ice were MICE3 (5'-GAGATGGT GAAAGAGGTG) and MICE4 (5'-TTGTTTCTCTCCACGGCA). The PCR was performed with the following conditions: 1×Taq polymerase buffer (Promega), 0.3 mM dNTPs, 2.5 mM MgCl$_2$, 0.5$\mu$M each primer and 1U of Taq DNA polymerase (Promega) in a total volume of 25 $\mu$l. DNA was denatured at 94° C. for 2 min prior to 30 cycles of 94° C. for 1 min, 55° C. for 2 min, 72° C. for 2 min.

Northern blots were probed with Ich-3 cDNA (from the Pst I site within the active site to the 5'-end of the cDNA). Since Ich-3 transcription is dramatically induced after LPS stimulation, the transcription of the mutant Ich-3 can be induced by LPS (FIG. 2A) was tested. Tissue samples were isolated from both wild type and mutant mice before and 5 hrs after LPS injection at 40 mg/kg of body weight intraperitoneally. As shown in FIG. 8A, even when the Ich-3 transcript level is dramatically induced in wild type mice, intact Ich-3 transcript in mutant mice could not be detected. Wild type mice express a 1.4 kb Ich-3 mRNA which is highly induced upon LPS stimulation whereas no wild type Ich-3 mRNA can be detected in the mutant mice even after LPS stimulation (FIG. 8A). A faint band of approximately 1.3 kb only in mutant mice in some of the tissues tested could be seen. This may be the result of aberrant transcription or splicing of the mutant allele.

A monoclonal antibody was generated against ICH-3 (See Example 2). This ICH-3 antibody recognized two proteins of 43 kDa and 38 kDa in LPS stimulated tissue. To determine if these two proteins are encoded by the Ich-3 locus, proteins were isolated from various tissues of wild type and Ich-3 mutant mice. Western blots probed with this antibody showed that these two proteins are specifically missing in Ich-3 mutant mice (FIG. 8B). Thus, the Ich-3 locus encoded two proteins of 43 kDa and 38 kDa and the targeted mutation in Ich-3 has eliminated expression of both proteins.

To determine if a deficiency in Ich-3 affects the expression of Ice, the expression of Ice by Northern blotting and RT-PCR using mRNA isolated from wild type and Ich-3 mutant thymus and kidney was also analyzed. A comparable amount of Ice transcript in both wild-type and mutant mice (FIGS. 8C–8D) could be seen. Thus, the absence of the Ich-3 gene product did not have any obvious adverse effect on the level of Ice mRNA.

Example 8

Ich-3 Mice Develop Normally

The Ich-3 deficient mice developed normally and their growth rate was the same as the wild type in postnatal development (not shown). Histological analysis of kidney, thymus, heart, and lung, in which Ich-3 expression was higher than other tissues, from 7–10 weeks old mice showed no gross abnormalities (data not shown). The percentages of different subsets of T cells from freshly isolated thymocytes was examined by flow cytometry. There was no significant differences in the distribution of CD4$^+$CD8$^+$, CD4$^+$CD8$^-$, CD4$^-$CD8$^+$, or CD4$^-$CD8$^-$ populations as compared with those of wild-type mice (data not shown).

Example 9

Apoptosis in Ich-3 Deficient Mice

Granule serine protease (GraB) derived from cytotoxic T lymphocytes (CTL) can induce apoptosis in the presence of the pore forming protein perforin (Shi et al., *J. Exp. Med.* 176:1521–1529 (1992)). To determine the role of ICH-3 in apoptosis induced by GraB, the ability of Ich-3−/− embryonic fibroblasts (EF) to undergo apoptosis following treatment with GraB or Granzyme 3 (Gra3) and perforin was examined. Embryonic fibroblasts from Ich-3−/− mice and wild type littermate controls were treated with varying concentrations of GraB or Gra3 in the presence of a constant amount of perforin (50 ng/ml) for a period of 2 and 8 hrs, respectively. More than 40% of wild type EF cells died in 0.8 μg/ml of GraB or Gra3 in the presence of 50 ng/ml of perforin, whereas only baseline levels of apoptosis were detected in Ich-3−/− EF cells (FIG. 9).

Thus, Ich-3−/− EF cells were completely resistant to the dose of GraB and Gra3 tested (up to 0.8 μg/ml). This result suggested that ICH-3 plays an important role in GraB mediated apoptosis in EF cells.

Thymocytes are sensitive to several apoptotic stimuli such as irradiation and dexamethasone (Cohen, J. J., et al., *Ann. Rev. Immunol.* 10:267–293 (1992)). To determine if apoptosis of thymocytes is affected by a mutation in the Ich-3 locus, Ich-3−/− thymocytes were examined for defects in apoptosis using a variety of apoptotic induction signals. Thymocytes isolated from 6–7 week old, wild-type and Ich-3 mutant mice were treated with 500 rads of γ-irradiation, or dexamethasone (1 (M), or 10 nM phorbol myristate acetate (PMA) and 500 nM $Ca^{2+}$ ionophore, and cell viability was examined 10 hr or 24 hr after treatment by using FCAS analysis after staining with propidine iodine. (Schwartz, et al., "Cell Death—Methods in Cell Biology." vol. 46, Academic Press).

No significant difference in apoptosis between mutant and wild type thymocytes was found under these stimuli, suggesting that the mutant Ich-3 thymocytes die as readily as wild type thymocytes (data not shown).

Fas antigen belongs to the TNF-α receptor superfamily. This family is characterized by its cytoplasmic death domain which is homologous to the Drosophila Reaper protein (Goldstein et al., 1995). Activation of Fas by either Fas ligand or agonistic anti-Fas antibody binding induces apoptosis (Yonehara et al, *J. Exp. Med.* 169:1747–1756 (1989); Suda et al., *Cell* 75:1169–1178 (1993)). Fas-mediated apoptosis can be prevented by crmA, suggesting that crmA inhibitable ICE/CED-3 proteases are crucial for Fas-mediated apoptosis (Tewari & Dixit, *J. Biol. Chem.* 270:3255–3260 (1995); Enari et al., *Nature* 375:78–81 (1995); Los et al., *Nature* 375:81–83 (1995)). Ich-3 induced cell death can be inhibited by crmA and Ich-3 expression can be detected in thymus and spleen (See Example 3). Thus, it is possible that Ich-3 may play a role in Fas-mediated apoptosis and Ich-3 mutant mice may have different sensitivity to Fas mediated cell death. Therefore, sensitivity for anti-Fas induced apoptosis in Ich-3 mutant thymocytes was also examined.

Anti-Fas induced thymocytes apoptosis

Thymocytes were dissociated from thymus of 5–7 week old male mice and incubated in RPMI media with 10% fetal bovine serum at a concentration of $2\times10^6$ cells/ml in 24 well tissue culture plates. They were incubated with anti-Fas antibody (JO-2, Pharmingen) for 20 hr with various concentrations of the antibody. Cell viability was determined by trypan-blue dye exclusion.

Thymocytes were isolated from Ich-3 mutant as well as wild-type mice of 5–7 weeks of age and incubated with different concentration of anti-Fas antibody. As shown in FIG. 10, thymocytes from Ich-3 deficient mice were partially resistant to anti-Fas induced apoptosis. Thus, the product of Ich-3 gene may be a downstream component of the Fas pathway.

The phenotypes of Ich-3 deficient mice are similar to that of the Ice deficient mice in many ways. The Ich-3 mutant thymocytes are partially resistant to Fas induced apoptosis, but they die normally when stimulated with dexamethasone, γ-irradiation, or PMA and calcium ionophore. Ich-3−/− embryonic fibroblasts are resistant to granzyme B induced apoptosis. Mutations in the *C. elegans* cell death gene ced-3 eliminates essentially all the programmed cell death during *C. elegans* development (Ellis & Horvitz, *Cell* 44:817–829 (1986)). In contrast, both Ice and Ich-3 deficient mice are only partially defective in apoptosis induced by Fas.

Example 10

Ich-3-Deficient Mice are Resistant to Septic Shock

Administration of LPS to mice induces production and secretion, largely by macrophages and monocytes, of proinflammatory cytokines which are subsequently released into the circulation (Dinarello, C. A., et al., *J. Am. Assoc.* 269:1829–1835 (1993)). Lethal endotoxic shock can be induced by intraperitoneal injection of a high dose of LPS in mice. Wild-type mice show a series of responses such as shivering, fever, lethargy, watery eyes and ultimately death. Ice-deficient mice are resistant to a lethal dose of endotoxin because of a dramatic reduction in release of proinflammatory cytokines such as IL-1α and IL-1β (Li et al., *Cell Death & Diff.* 3:105–112 (1995); Kuida et al., *Science* 267:2000–2003 (1995)).

Induction of septic shock

To examine if Ich-3 deficient mice are also resistant to LPS, 8 week old wild-type and Ich-3-deficient mice were injected with LPS. The mice were injected intraperitoneally with LPS from *Escherichia coli* 0127:B7 (Sigma, St Louis, Mo.) at a dose of 40 mg/kg body weight. The injected mice were monitored for signs of endotoxemia and lethality at least twice daily. The systemic release of cytokines after toxin challenge was determined by ELISA kits for murine IL-α and β (Genzyme, Cambridge, Mass.). Blood was taken 5 hr after LPS injection.

Only 11% of the wild type mice survived 4 days after receiving LPS (FIG. 11). Symptoms of endotoxic shock similar to those observed in wild-type mice were also observed in Ich-3 deficient mice except that the Ich-3 deficient mice were less lethargic and most of them recovered within 48 hours. Most of the Ich-3-deficient mice (80 %) survived 4 days after LPS treatment. Survival rate of heterozygous mice was about the half of the Ich-3-deficient mice (44%).

To investigate whether Ich-3 mutant mice have a defect in production of proinflammatory cytokines in vivo which may explain why they are resistant to LPS, the plasma levels of IL-1α and IL-1β which are dramatically reduced in Ice deficient mice (Li et al., *Cell* 80:401–411 (1995); Kuida et al., *Science* 267:2000–2003 (1995)) were tested. LPS at a dose of 40 mg/kg body weight was administrated to Ich-3 mutant and wild-type control mice, and plasma levels of IL-1α and IL-1β were measured by ELISA before and 5 hrs after LPS injection.

IL-1α and IL-1β were undetectable in both mutant and wild-type mice under control conditions. Plasma IL-1β levels were significantly increased in wild type mice 5 hrs after LPS injection. Surprisingly, plasma IL-1β levels in Ich-3 mutant were undetectable 5 hrs after LPS injection (Table 3), suggesting that Ich-3 has a regulatory role in mature IL-1β production in vivo. Plasma levels of IL-1α were also significantly lower in Ice-deficient mice than wild type mice after LPS stimulation (Li et al, *Cell* 80:401–411 (1995); Kuida et al., *Science* 267:2000–2003 (1995)), suggesting that IL-1β may have a role in regulating IL-1α production and secretion.

Thus, Ich-3 mutant mice were further examined to determine if they had a defect in IL-1α production. Plasma of Ich-3 mutant and wild-type control mice were assayed for IL-1α levels 5 hrs after LPS injection by ELISA. These experiments showed that, like Ice-deficient mice, Ich-3-deficient mice also have severely reduced plasma level of IL-1α after LPS stimulation Table 3), which is consistent with the hypothesis that IL-1β may have a role in regulating IL-1α levels in vivo.

TABLE 3

Plasma Cytokine Levels in Endotoxic Shock.

| Cytokine | Stimulus | Cytokine Concentration pg/ml) | |
| --- | --- | --- | --- |
| | | Ich-3 +/+ | Ich-3 −/− |
| IL-1α | LPS | 850 ± 150 | 40 ± 24 |
| IL-1β | None | 0* | 0* |
| | LPS | 195 ± 60 | 0* |

Ich-3 mutant (−/−) and wild type (+/+) mice were bled from the retro-orbital plexus 4 hr after LPS stimulation. The plasma was used for ELISA. The data are mean ± SEM. of at least three individual mice.
*lower than detection level.

An ICE pathway

The critical role of IL-1 in sepsis has been highlighted by the Ice-deficient mice which are defective in secretion of both IL-1α and IL-1β and are resistant to LPS challenge (Li et al., *Cell* 80:401–411 (1995); Kuida et al., *Science* 267:2000–2003 (1995)). IL-1β is an important mediator of chronic and acute inflammatory diseases (Dinarello, C. A., *Blood* 77:1627–1652 (1991)). Although IL-1β is a part of primary host defense to infections, over-stimulation of the system results in excessive or continued production of IL-1 which leads to debilitation of normal host functions with disastrous consequences. Reduction of IL-1 production and secretion is a target of therapy for many diseases. Pro-IL-1β does not contain a signal peptide and mature IL-1β is not usually detected inside the cell, suggesting that processing occurs concurrent with release (Hazuda, D. J., et al., *J. Biol. Chem.* 266:7081–7086 (1991)). Thus, understanding the regulation of pro-IL-1β processing may be critical for design of drugs which may inhibit the release of mature IL-1β. Since the results from the Ice-deficient mice indicated that ICE is responsible for processing at least 90% of mature IL-1β (Li et al., *Cell Death & Diff.* 3:105–112 (1995); Kuida et al., *Science* 267:2000–2003 (1995)), it is a surprising that Ich-3-deficient mice are also resistant to LPS and also have defects in processing pro-IL-1β.

There are three possible hypotheses which may explain why Ich-3-deficient mice are also defective in processing pro-IL-1 in vivo. The first hypothesis is that Ich-3 controls or processes IL-1β in cells other than marophages and monocytes. This would explain why Ich-3-deficient macrophages and monocytes process pro-IL-1β at the same level as that observed in the corresponding wild type cells in vitro; however, this hypothesis cannot explain why Ich-3 deficient mice are defective in processing IL-1β in vivo when stimulated with LPS since monocytes and macrophages are the major producers of IL-1β in vivo (Dinarello, C. A., et al., *J. Am. Assoc.* 269:1829–1835 (1993)).

The second hypothesis is that ICH-3 protein may form a complex with ICE which is essential for ICE to process IL-1β. This would explain why Ich-3-deficient mice are defective in processing IL-1β in vivo when stimulated with LPS. This hypothesis, however, is inconsistent with several in vitro studies. First, it does not explain why Ich-3-deficient macrophages and monocytes can process and secrete IL-1β in vitro when stimulated with LPS and ATP or LPS alone. Second, ICE alone is sufficient for the processing IL-1β in vitro (Thornberry, N. A., et al., *Nature* 356:768–774 (1992)). Thus, the preferable hypothesis is that ICH-3 is an upstream regulator of ICE activity in vivo. It can therefore be hypothesized that in wild-type mice, LPS challenge leads to the activation of ICH-3 expression and proteolytic activity which in turn may indirectly activate ICE either by activating another member of the ICE family or by inactivating an inhibitor of ICE. This hypothesis, however, is consistent with in vitro studies which found that expression of Ich-3 does not result in processing of pro-IL1β in COS cells but potentiates processing of pro-IL1β when cotransfected with an Ice expression construct.

This sequential pathway can be bypassed in vitro, where much stronger signals can be delivered than what would be possible in vivo under physiological conditions. It is predicted that in vivo, this sequential pathway is arranged in such a way so that the ICE/CED-3 members in the beginning of this pathway are more easily activated. When a physiological stimulus is delivered, the ICE/CED-3 family member in the beginning of the pathway is activated, which in turn activates the next ICE/CED-3 family member in line and so on. An in vivo signal would activate ICH-3 first which then indirectly activates ICE. In vitro, however, more than one member of the ICE/CED-3 family can be activated simultaneously by a strong signal and activation of any of these proteases may be sufficient by itself to cause cell death. Consistent with this hypothesis, although Ich-3-deficient mice have defects in production of mature IL-1 in vivo after LPS stimulation, Ich-3-deficient macrophages can process and secrete IL-1β normally when stimulated with LPS and ATP. These results suggest that although ICE is under the control of ICH-3 in vivo, the requirement can be bypassed in vitro when stimulated with a stronger signal. This hypothesis may also explain why macrophages that are defective for either Ice or Ich-3 can still undergo apoptosis when stimulated with ATP because multiple proteases may be activated directly by ATP bypassing the requirement for ICE or ICH-3. This hypothesis is also consistent with the fact that in vitro, high doses of ICE inhibitors are required to inhibit apoptosis because multiple proteases with different specificities may be activated by a single strong inducer of apoptosis.

In general, the control of apoptosis in m s appears to be very complex and delicate. First, different apoptotic signals may activate different effectors. While Ich-3 and Ice mutant thymocytes are partially resistant to Fas induced apoptosis, they are not resistant to 500 Rads of γ-irradiation, dexamethasone (1 μM), or 10 nM PMA and 500 nM $Ca^{2+}$ ionophore. Thus, Fas may activate the ICE pathway more specifically than some of the other signals. Secondly, even the same signal at different doses may activate different components of the ICE pathway. For example, LPS is incapable of inducing IL-1β secretion in Ich-3 mutant mice and thus, cannot activate ICE in vivo; however, LPS in high dose can induce IL-1β secretion in vitro and thus, can activate ICE directly in vitro even in the absence of ICH-3. Therefore, such complexity requires caution when interpreting in vitro data on apoptosis in mice relative to mutations in the ICE family.

Inflammation and apoptosis

Consistent with its proinflammatory role, Ich-3 transcription is highly inducible after LPS stimulation. When wild type mice are challenged with a high dose of LPS, the Ich-3 transcript levels increase dramatically in spleen, thymus, heart, liver and lung where Ich-3 expression is very low in all of these tissues under normal condition (See Example 2). In contrast, Ice transcript levels are increased only in thymus after LPS stimulation. These characteristics of Ich-3 action are consistent with its regulatory role in other ICE/CED-3 family members. Homozygous Ich-3 mutant mice are highly resistant to the lethality of LPS whereas an approximately 50% survival rate is observed in heterozygous mice, suggesting that Ich-3 confers a gene dose-sensitive resistance to LPS.

Ich-3 mutant mice are resistant to septic shock induced by LPS, suggesting that Ich-3 plays an important role in inflammation. Ich-3 mutant mice are normal, however, in clearing pseudomonas bacterial infection (unpublished results), suggesting that Ich-3 and, hence IL-1 as well are not essential for inflammatory response in this case. IL-1β is undetectable in normal healthy individuals or animals.

There is a dramatic induction of IL1 production by a variety of cells in response to infection, microbial toxins, inflammatory agents, and complement and clotting components (Dinarello, C. A., Blood 77:1627–1652 (1991)). IL1 has been postulated to be part of the body's primary defense responses to invasions (Dinarello, C. A., Blood 77:1627–1652 (1991)). Both Ice (Li et al., Cell 80:401–411 (1995)) and Ich-3 mutant mice, however, are apparently not any more prone to infections than wild type mice, at least in controlled animal facilities.

Ich-3 mutant mice also clear pseudomonas infection normally, although both mutants are highly resistant to LPS induced lethality. In addition, the initial symptoms of sepsis, such as fever, lethargy and watery eyes, which may be induced by other cytokines such as TNF-α, are present in Ich-3 mutant mice after LPS injection, suggesting that these mice are indeed in septic shock. Absence of Ich-3 selectively reduces the mortality of sepsis. These results suggest that a super-induction of IL-1β together with IL-1α may be necessary and sufficient for mortality of sepsis. Since without Ich-3 and with significantly reduced levels of IL-1, these mice can clear a septic dose of pseudomonas (unpublished observation), Ich-3 and thus, IL-1β, appear to be dispensable for fighting bacterial infection.

Although without a systematic study of cell numbers in these organs in the mutants, it cannot be ruled out that Ich-3-deficient nice have defects in developmental and homeostatic cell death and therefore, have excess cells in these organs, it is suggested that a major function of Ich-3 is not in development or homeostasis but rather in host defense responses under severe stress or viral infection conditions. These findings suggest that inhibitors to ICH-3 may be able to significantly reduce mortality of sepsis without compromise to host defense mechanisms. Furthermore, such inhibitors may also be useful in treating other inflammatory diseases in which IL-1β plays a significant role such as rheumatoid arthritis (Li et al., Cell 80:404–411, 1995).

Since ICE shares sequence homology with the C elegans programmed cell death gene ced-3 product, it is interesting to speculate that perhaps inflammatory responses are evolved from primitive mechanism of programmed cell death. Although the most recognized role of IL-1β has been in inflammation, there is indication that IL-1β may play an active role in promoting apoptosis as well. Inhibition of IL-1β by a naturally existing antagonist, IL-1Ra, or by a neutralizing antibody to IL-1β or IL-1β receptor, can reduce cell death in a number of systems and conditions (Friedlander, R. M., et al., J. Exp. Med. 184:August 1996, In Press). It is speculated that perhaps the lethality of sepsis may be partly due to the ability of IL-1β to induce apoptosis which may contribute to organ failure, a major cause of death in sepsis. Results presented here suggest that there may be not only evolutionary links but also mechanistic connections between apoptosis and inflammation.

Example 11

IL-1 Production in Cultured Ich-3 Mutant Macrophages and Monocytes

The phenotypes of Ich-3-deficient mice as described to this point are very similar to that of Ice-deficient mice except that unlike Ice-3-deficient mice, the transcription of Ice is at wild-type levels in the Ich-3 mutant. Thus, it was determined whether Ich-3−/− mice have normal ICE function. Since mice with a mutation in the Ice locus are severely defective in processing pro-IL-1β ((Li et al., Cell 80:401–411 (1995); Kuida et al., Science 267:2000–2003 (1995)), the ability to process pro-IL-1β is a specific indication of ICE function.

Thioglycollate-elicited peritoneal macrophages (PECs) can be stimulated with LPS to induce the expression of pro-IL1β and with ATP to induce apoptosis which causes the release of mature IL-1β (Hogquist et al., 1991). Monocytes can be stimulated by LPS to induce the expression and secretion of IL-1β (Perregaux & Gabel, J. Biol. Chem. 269:15195–15203 (1994)). Both Ice−/− macrophages and Ice−/− monocytes are defective in processing pro-IL-1β in vitro (Li et al., Cell 80:401–411 (1995); Kuida et al., Science 267:2000–2003 (1995)). Macrophages and monocytes are major producers of IL-1 in vivo (Dinarello, C. A., Blood 77:1627–1652 (1991)). These results suggest that ICE is responsible for processing 90% or more of mature IL-1β in vivo. Thus, if Ich-3 mutant cells can produce normal levels of IL-1β in vitro, it will be strong evidence that normal ICE function is present in Ich-3 mutant mice.

To examine if Ich-3 is expressed in macrophage and monocytes, the expression of Ice and Ich-3 in wild type PECs and splenocytes by Northern blot (FIG. 12A) was investigated.

In vitro assays of IL-1 release from monocytes and macrophages

Peritoneal macrophages were prelabeled by incubating in [$^{35}$S]-methionine (120 μCi/ml) for 20 hr, and thereafter incubated in LPS (1 μg/ml) for an additional 4 hrs. The cells were then treated with ATP (5 mM) for 30 min, then washed and chased in fresh media for 20 hr. The media samples (500 μl) were collected, and two volumes of RIPA buffer (150 mM NaCl, 1.0% NP40, 0.5% DOC, 0.1% SDS, 50 mM Tris-HCl pH8.0) containing protein A (50 μl) and 5 μg of anti-murine IL-1α and IL-1β (kind gift of Dr. D. Chaplin) were added. Samples were incubated overnight at 4° C. with gentle rotation and then washed four times with RIPA and two times with TBS (150 mM MaCl, 25 mM Tris-HCl pH7.5). Samples were then analyzed on 15% SDS-polyacrylamide gels.

Spleen cells were dissociated and the cells attached to tissue culture dishes within two hours were used as monocytes. Monocytes were treated with LPS (1 μg/ml) with or without nigericin (10 μM) for 20 hr. For ELISA, supernatant of LPS-treated monocytes was assayed for mature IL-1β using a kit from Genzyme (Cambridge, Mass.).

Similar amounts of Ice and Ich-3 transcripts in both PECs and splenocytes were seen. To examine if Ich-3−/− macrophages and monocytes can process pro-IL-1β in culture, PECs from both wild type and Ich-3 mutant mice were isolated. Isolated macrophages labeled with [$^{35}$S] methionine were stimulated with LPS to induce expression of pro-IL-1β and then treated with ATP to induce apoptosis. There was no difference in apoptosis of macrophages stimulated with ATP in both wild type and Ich-3 mutants (data not shown), which is similar to the Ice mutant mice (Li et al., Cell Death & Diff. 3:105–112 (1995)). The release of mature IL-1β in the culture medium after induction of apoptosis by ATP was examined by immunoprecipitation using antibodies specific to IL-1α or IL-1β. The stimulated macrophages from Ich-3 deficient mice released mature IL-1α and IL-1β at the same level as that of wild type macrophages (FIG. 12B).

It was also determined whether Ich-3 mutant monocytes could be stimulated to produce mature IL-1β in vitro. Monocytes were isolated from spleens of both wild type and Ich-3 mutant mice and cultured in the presence of a high dose of LPS or LPS plus nigericin. Secretion of mature IL-1β by monocytes into tissue culture media after LPS or LPS and nigericin stimulation was examined by ELISA. Nigericin is a $K^+$-$H^+$ ionophore that can activate a plasma membrane adenosine triphosphatase (ATPase) and enhances release of mature IL-1β (Perregaux & Gabel, J. Biol. Chem. 269:15195–15203 (1994)). As shown in Table 4, the ability of Ich-3-/- monocytes to secrete mature IL-1β was similar to that of wild type. Thus, wild type and Ich-3 mutant monocytes demonstrated no difference in their ability to secrete mature IL-1β in vitro when stimulated with LPS. These results show that IL-1β release in culture was not reduced by the loss of Ich-3 function, and thus Ich-3 mutant monocytes and macrophages have normal IL-1β converting enzyme activity.

TABLE 4

Secretion of mature IL-1β by monocytes.

| Stimulus | IL-1β Concentration (pg/ml) | |
|---|---|---|
| | Ich-3 +/+ | Ich-3 -/- |
| None | 0 | 0 |
| LPS (1 μg/ml) | 188 ± 57 | 183 ± 35 |
| LPS (1 μg/ml) + nigericin (10 μM) | 460 ± 87 | 580 ± 190 |

Monocytes isolated from Ich-3 mutant (-/-) and wild type (+/+) mice were treated either with LPS (1 μg/ml) or LPS (1 μg/ml) + nigericin (10 μM) for 20 hrs. The supernatant was used for ELISA. The data are mean ± SEM. of monocytes from three individual mice for each genotype.

Example 12

Reduced Germ Cell Endowment and Delayed Follicle Activation in Ich-3Mutant Female Mice Expression of Ich-3 in the ovary was detectable by Northern blot analysis (data not shown). Although Ich-3-/- female mice were fertile and had normal litter sizes, in depth morphometric and histological evaluations of the ovaries revealed three striking phenotypes.

Histological and morphometric examination of mouse ovary

Ovaries were isolated from wild-type or Ich-3 mutant female mice at either 4 days or 6–7 weeks of age postpartum, fixed in neutral-buffered 4% paraformaldehyde, and embedded in paraffin for morphometric and histological evaluations. For all tissues, serial sections (7 μm) were mounted on glass slides, stained with Weigert's hematoxylin pycric acid methyl blue dye, and visualized by light microscopy. The numbers of oocyte-containing primordial, primary and small preantral follicles were estimated using the fractionator and nucleator principles for stereological analysis as described previously described in the art (Gundersen et al., 1988; Ratts et al., 1995). Differences in follicle numbers were analyzed by a one-way analysis of variance followed by Scheffe's test, with significance assigned at P<0.05.

At postpartum day 4 of age, estimates of the numbers of oocyte-containing follicles at the primordial, primary and small preantral stages of development demonstrated significantly less oocyte-containing primordial follicles (FIG. 13A). The oocyte-containing follicles represent the stockpile of germ cells available for ovulation throughout reproductive life, in Ich-3 mutant mice. The reduced endowment of primordial follicles in female Ich-3 mutant mice may be the result of the subsequent degeneration of oocytes in follicles formed during the perinatal period, as remnants of primordial follicle-like structures containing a single layer of fusiform granulosa cells without an oocyte were scattered throughout the ovaries of Ich-3 mutant mice (FIG. 12B). Some of the follicle-like structures contained multiple oocyte-like cells instead of one oocyte as found in wild type primordial follicles (FIG. 12B).

The abnormal structures were never observed in ovaries of wild-type mice (FIG. 12C). Furthermore, not one actively growing immature follicle (either primary or small preantral) could be detected in serial sections of ovaries collected from mice lacking functional Ich-3 (FIG. 12A, insert), indicative of an early defect in the timing of activation and recruitment of quiescent follicles into the growing pool. In contrast to the clear differences in the ovaries of mutant versus wild-type mice early in life, a similar series of morphometric and histological evaluations conducted at 6–7 weeks of age postpartum revealed no discernible differences in follicle numbers or ovarian histology (data not shown).

The role of ICH-3 in female germ cell endowment and ovarian follicular dynamics

The progeny ratio of homozygous Ich-3 mutants to wild-type offspring from heterozygous female and male breedings deviates slightly from the expected Mendelian ratio (30% Ich-3 mutant and 23% wild type vs. expected 25% mutant and 25% wild-type). This finding prompted investigation into the development of the ovary in Ich-3 mutant mice. Initial histological and morphometric examination of ovaries collected from adult mice at 6–7 weeks of age did not reveal any discernible differences in the Ich-3 mutant and wild-type mice.

Further examination of neonatal ovaries, however, revealed striking phenotypic abnormalities in Ich-3 mutant mice. At postpartum day 4, not one actively growing follicle (primary or small preantral) was observed in six mutant ovaries analyzed. In contrast to this, on average there were 600 primary follicles and 100 small preantral follicles per ovary of wild-type littermates. Thus, activation of early follicle growth, as measured by transition of a quiescent primordial follicle to an actively growing stage, is significantly delayed in Ich-3 mutant mice.

It is interesting to draw a comparison with the nematode C. elegans. In C. elegans, ced-3 mutants develop normally despite of 20% excess cells (Ellis & Horvitz, Cell 44:817–829 (1986)). However, one of the most significant defects of ced-3 mutant is a 30% delay in onset of egg-laying (unpublished observation). It takes about 2.5 days for a wild type C. elegans to reach egg-laying stage whereas it takes about 3.5 days for a ced-3 mutant to lay eggs. This defect is fully suppressible by a ced-3 transgene, indicating that this defect is due to a mutation in ced-3 rather than a linked mutation. Moreover, this defect is not caused by problems with the neuronal control of egg-laying system since ced-3 mutants do not exhibit Egl (egg-laying) defect (Ellis & Horvitz, *Cell* 44:817–829 (1986)). It is therefore possible that ced-3 and programmed cell death plays a significant role in the timing of normal egg growth and maturation in *C. elegans*, analogous to the apparent requirement for ICH-3 in early follicle growth activation in the mouse.

Endowment of a normal complement of primordial follicles, the source of the eggs for ovulation throughout life, in the neonatal Ich-3 mutant mouse ovary is also severely affected: at postpartum day 4, wild type female mice have approximately 20,000 oocyte-containing primordial follicles whereas Ich-3 mutant littermates have only 7,000. Cell death plays a predominant role in the establishment and subsequent depletion of the female gonadal germ cell pool in mammalian and avian species (Tilly, J. L., *Frontiers Biosci.* 1:d1–10 (1996)). Of the estimated two million germ cells present in the embryonic human ovary, only 300–350 of these oocytes are released from the ovary through ovulation for potential fertilization. The remaining, and overwhelming majority, of female germ cells are naturally lost directly through attrition during the perinatal period or as a consequence of somatic cell death and follicular atresia during pre- and postpubertal life. Although the regulation of cellular depletion from the ovary remains to be fully elucidated, recent studies have provided evidence that members of the Ice/ced-3 gene family may in fact be involved in ovarian cell death (Flaws, J. A., *Edocri.* 136:5042–5053 (1995)).

In summary, it was found that postpartum day 4 Ich-3 mutant female mice have significantly less primordial follicles in the staring "stockpile", suggesting that these mice: 1) began with a smaller embryonic pool of germ cells to undergo clonal expansion in the developing ovary; or 2) display a defect in clonal expansion of the germ cell pool in the fetal ovary; or 3) exhibit greater losses of oogonia and oocytes during the perinatal waves of attrition. If the latter possibility is true, Ich-3 would play a role opposite of that expected since this gene is a member of the CED-3/ICE family of death-inducing proteases, yet its ablation yields a reduced oocyte survival rate.

Interestingly, by 6–7 weeks of age, differences in numbers of follicles at the primordial, primary or small preantral stage of development in adult Ich-3 mutant versus wild-type female mice were not observed. Since the Ich-3 mutants start off with only one-third the number of primordial follicles per ovary as compared with their wild-type littermates, these findings further support the role of ICH-3 in the timing of early follicle activation and recruitment. For instance, wild-type females, from the time of birth until reproductive senescence, almost continuously "activate" primordial follicles to become a part of the growing follicle pool which will serve as a potential source of the egg for ovulation. The rates of follicle recruitment are such that a delay in only one week in the timing of follicle activation (such as that potentially occurring in Ich-3 mutants) would be sufficient for the wild-type mice to "deplete" their primordial pool to levels observed in the Ich-3-deficient females. Consequently, these findings suggest that although the time in life at which complete follicular exhaustion occurs (reproductive senescence, the menopause in humans) would not be affected by the absence of Ich-3, the timing of puberty may be delayed due to an initially reduced pool of actively growing follicles in Ich-3 mutant ovaries.

In addition to the reduced endowment of primordial follicles in the Ich-3 mutants, neonatal ovaries collected from these mice also appear grossly abnormal in morphology. Reminiscent of the ovarian morphology of Bcl-2-deficient mice (Ratts, V. S., et al., *Endocrinology* 136:3665–3668 (1995)). In contrast to the wild-type ovaries, many primordial follicle-like structures containing a single layer of fusiform granulosa cells surrounding an empty space (presumably where an oocyte once existed), or a complex of multiple oocyte-like cells instead of the normal single oocyte were observed. The empty follicle-like structures suggest that the oocytes previously occupying these spaces have degenerated, which may partially account for the reduced numbers of endowed follicles in the mutants. However, the presence of follicles containing multiple oocyte-like cells in a large complex suggests another possibility: Ich-3 mutants exhibit a defect in early folliculogenesis such that steps leading to the proper formation of a follicle are disrupted and hence granulosa cells surround either too many oocytes, or conversely no oocyte at all. In any case, these findings collectively indicate that Ich-3 is very important for establishment of the female gonadal germ cell pool, early folliculogenesis, and activation of quiescent primordial follicles for recruitment into the growing pool of follicles required for ovulation.

Summary of results concerning the Ich-3 mutant mouse

Observations are presented describing the inactivation by gene-targeting, of a new member of the Ice/ced-3 family of cell death genes, Ich-3. Thymocytes from Ich-3 deficient mice are partially resistant to apoptosis induced by Fas antibody. Ich-3 −/− embryonic fibroblasts are resistant to granzyme B induced apoptosis. Neonatal Ich-3−/− female mice show delayed follicle activation, a reduced endowment of primordial oocytes and abnormal follicles. Like Ice deficient mice, Ich-3 mutant mice are resistant to endotoxic shock induced by lipopolysaccharide (LPS). Production of both IL-1α and IL-1β, a crucial event during septic shock, is severely reduced in Ich-3 mutant mice after LPS stimulation. In contrast to Ice deficient mice, whose macrophages and monocytes cannot process pro-IL-1β in culture after stimulation with LPS and ATP or LPS alone, Ich-3 mutant monocytes and macrophages process and secrete mature IL-1β normally under these conditions.

Similar to Ice, overexpression of Ich-3 induces apoptosis in Rat-1 fibroblasts and Ich-3-induced cell death could be prevented by bcl-2 and crmA. Differing from Ice, however, expression of Ich-3 is highly inducible by LPS, suggesting that Ich-3 may have a regulatory role in both apoptosis and inflammatory responses. ICH-3 does not process proIL-1β directly but overexpression of Ich-3 does stimulate processing of pro-IL-1β by ICE. Stimulation of wild type mice by LPS dramatically induces the production and secretion of mature IL-1β. This response is absent in mice that are deficient for Ice suggesting that ICE is responsible for processing at least 90% of IL-1β (Li et al., *Cell Death & Diff.* 3:105–112 (1995); Kuida et al., *Science* 267:2000–2003 (1995)). Interestingly, it was found that, although ICH-3 does not process pro-IL-1β directly, Ich-3 deficient mice are also resistant to lethal dose of LPS which can be attributed to a lack of IL-1 production. An important difference between Ich-3 and Ice deficient mice is that Ich-3 deficient macrophages and monocytes can process pro-IL-1β normally in vitro when stimulated with LPS and ATP or LPS alone. These results suggest that Ich-3 encodes an upstream regulator of ICE.

Example 13

Reduction of Mortality Due to Endotoxin (Bacterial Lipopolysaccharide) in Normal Animals Control non-mutant mice are treated with a compound that inhibits ICH-3 prior to induction or during shock due to LPS. These compounds may be chosen from the group including but limited to, peptide inhibitors such as YVAD-cmk, Ac-DEVD-CHO, cysteine protease inhibitors or serine protease inhibitors such as trans-epoxysuccininyl-L-leucylamido-(4-guanidino) butane (E64) and leupeptin, calpain inhibitors I and II.

The treated mice and non-treated control mice are injected intraperitoneally with LPS from *Escherichia coli* 0127:B7 (Sigma, St Louis, Mo.) at a dose of 40 mg/kg body weight. The injected mice are monitored for signs of endotoxemia and lethality at least twice daily. The systemic release of cytokines after toxin challenge is determined by ELISA kits for murine IL1-α and IL1-β (Genzyme, Cambridge, Mass.). Blood samples are taken 1–8 hrs after LPS injection.

This treatment should be applicable to any medical condition in which pathways induced by endotoxemia, including ICH-3 and apoptosis are involved.

Example 14

Screening of Compounds that Affect Septic Shock using Ich-3 Mutant Mice

The Ich-3 mutant mice exhibit resistance to endotoxic shock following injection of LPS. This is related to the lack of expression of ICH-3. Using the Ich-3 mouse to screen compounds allows the pre-clinical determination of combinations of compounds which would be be beneficial in treating sepsis in normal individuals, i.e. if one can eliminate the effects of ICH-3 with a drug (i.e. thereby simulating the knock-out mouse), a second drug may potentiate the resistance to sepsis. Alternatively, if a drug decreases the resistance to septic shock, its use may be contra-indicated for therapy. Additionally, the mutant mice may be used for screening compounds for treating infection, the sequelae of thermal injury, major trauma, or combinations thereof by correlating the effect of the compound in question on protecting the animal from the sequelae of sepsis or septic shock.

Compounds to be screened for activity can be administered to the Ich-3 mutant mice using pharmaceutically acceptable methods. See Remington's Pharmaceutical Sciences (1990). Shock is induced as in Example 12 or by any means known to those of skill in the art. Alternatively, other injuries such as thermal injury (see Example 16) may be induced. For example, the compound to be screened can be administered at various concentrations by parenteral injection, infusion, ingestion, and other suitable methods in admixture with a pharmaceutically acceptable carrier. The effect of various concentrations of the screened compound on increasing or decreasing the resistance to sepsis is measured relative to control Ich-3 mutant animals that have not been administered the compound to wild-type animals.

A significant increase in resistance to septic shock of the Ich-3 mutant mice by a screened compound is indicative that the compound would exhibit beneficial effects in the treatment of sepsis, either alone or in combination with a compound that inhibits ICH-3.

Particularly preferred compounds for screening are compounds known to inhibit activities of ICH-3 and ICE in vitro or any other candidate for treating sepsis or septic shock.

Example 15

Screening of Compounds for Affect on Follicle Activation using Ich-3 Mutant Mice The female neonatal Ich-3 mutant mouse exhibits significantly fewer primordial follicles as well as other defects related to folliculogensis. Compounds to be screened for folliculogenic activity can be administered to the Ich-3 mutant mice in a pharmaceutically acceptable excipient. For example, the compound can be administered at various concentrations to mice as an ointment or salve. Alternatively, other pharmaceutically acceptable modes of administration can be used. For example, a pharmaceutical composition comprising the compound can be administered by parenteral injection, infusion, ingestion, skin-patch application, and other suitable methods. The effect of the compound is measured relative to control Ich-3 mutant animals that have not been administered the compound.

A significant enhancement of folliculogenesis in mutant mice by a screened compound would indicate that this compound exhibits beneficial effects.

Particularly preferred compounds for screening are compounds known to inhibit activities of ICH-3 and ICE in vitro.

Example 16

Resistance of Ich-3 Mutant Mice to The Effect of Burns, Bacterial Infection and Sepsis A quantifiable burn and sepsis animal model was established in a variety of mouse strains, BlO, C3H, AKR, BALB/c and C57B16 using a clinical isolate of *Pseudomonas aeruginosa* administered intravenously and intratracheally in varying dosages in the presence and absence of a 10% body surface area (BSA) third degree burn. In this model, viable bacteria were administered intraperitoneally (up to $10^6$) in the presence or absence of a 10% BSA burn to the shaved back of anaesthetized mice using a heated brass probe. Burned animals received saline resuscitation (3–5 ml.) while recovering from anesthesia The time course of infection was followed. At various timepoints following infection, tissues (blood, lungs, liver, spleen) were harvested and immediately ground and plated on blood agar media for quantitative cultures, fixed for histology, frozen for cytokine mRNA assays and mycloperoxidase assays (a quantitative measure of infiltrating neutrophils).

Initial studies focused on the 72 hours following infection based on the observation that survival and bacterial clearance are completed in mice by three days following exposure. In control wild-type mice, bacteria rapidly entered the bloodstream by one hour following ip injection. This bacteremia was cleared by 24 hours. In the burned wild type mice, the same time course of infection was observed with three exceptions:

1) While the Pseudomonas bacteremia was cleared, bacteria due to organisms endogenous to the gastrointestinal tract was observed in the blood for up to 8 hours following thermal injury. These organisms were also found in the liver and lungs at periods up to 25 hours following thermal injury and after clearance of the bloodstream. Organisms isolated included Proteus spp, micrococci, enterococci, and anaerobic gram positive rods. These organisms were present in both lung and liver at 4 hours (75% of all animals in the lung, 100% in the liver), 7 hours (75% lung, 75% liver), and 25 hours (50% liver, 0% lung) following burns. The same pattern of bacteremia due to non-Pseudomonal organisms is observed if Pseudomonas is introduced via the airway (intratracheally up to $10^5$ bacteria).

2) Cultures taken aseptically from the subcutaneous area underneath the burned skin demonstrated no infection with Pseudomonas introduced either ip or intratracheally (it) but 10/12 of these sites were infected with the same endogenous organisms found systemically.

3) Pseudomonas introduced intratracheally was cleared from the lungs more rapidly (i.e., fewer organisms cultured at 2, 4 and 6 hrs) in the burned animals than in the control for the first 7 hours following the burn. However, infection persists at 24 hours only in burned animals (50%). Further, when the number of Pseudomonas organisms introduced intratracheally is increased (500,000 per animal), the number of organisms per gram of lung tissue (wet weight) was increased almost 3.7 fold in burned animals (mean 108,158 colonies per gram in burned animals (sd 13,711) vs mean 29,286 (sd 14,798) p<0.01). Thus, this model is capable of demonstrating both delayed clearance of exogenous (e.g., nosocomial) infection and significant levels of endogenous (i.e., gastrointestinal translocation) infection following a 10% BSA thermal injury.

Bacterial translocation from the gut following burns has been described extensively and is related to activation of cytokines, prostaglandins, neutrophils, with microvascular permeability and edema A number of studies have demonstrated that thermal injury causes activation of neutrophils and transient sequestration of neutrophils in the lungs (and other tissues) largely in the vascular tree.

The suggestion that ICH-3 was involved in the systemic response to injury was based on the initial observations that the ICH-3 knockout mouse was resistant to LPS (See Example 10). This was investigated in more detail.

When 10 mg of *E. coli* LPS was injected intraperitoneally into 10 Ich-3 mutant mice and 10 genetically identical wild-type mice, all of the wild-type animals died within 24 hours while all of the Ich-3 mutant mice survived. It was assumed that the defect was somehow protective against the LPS injury. However, when the degree of inflammation was scored, the Ich-3 mutant mice had greater levels of pulmonary neutrophilic infiltration than did wild type mice despite resistance to LPS. There was, however, a marked reduction in the level of anatomic lung injury in the knockout mice (by a score of 2.7 to 0.8 on a scale of 0–4 for edema, hemorrhage, alveolar proteinosis).

The Ich-3 mutant mice lacked serum IL-1β in response to LPS as measured by ELISA assay, while normal animals had high levels of IL-1β. However, it was already known based on the reports of three laboratories (L. Shornick, M. Tocci, and Immunex, in the Newsletter of the International Cytokine Society, 1994, p. 5) that the IL-1β knockout was completely normal in response to LPS and to injection. Thus, the defect in these animals may not only be that of isolated IL-1β deficiency but there may be additional components which also limit susceptibility to LPS-induced lung injury.

The Ich-3 mutant mice were further studied in groups of 15–20 tail-blot-confirmed ICH-3 knockouts, heterozygotes, and wild types each (depending on the litter size) in the presence and absence of Pseudomonas infection and burn injuries. The clearance of bacteria from the bloodstream was equivalent in wild type and Ich-3 mutant animals. The circulating white blood cell counts were slightly higher in the knockouts than those seen in wild-type animals with normal differential counts.

The histology of the lungs and livers from burned Ich-3 mutant mice and burned wild-type control animals was similar to that of the LPS injected mice: a greater intensity of neutrophilic infiltrate in the knockout mice with a marked reduction in edema and hemorrhage and greater adhesion of neutrophils to the vascular endothelium in the mutant mice. Burned skin in mutant mice also showed a much greater depth of neutrophil infiltration (from the dermis through the subcutaneous fat) than did wild-type animals which showed virtually no neutrophils above the level of the fatty subcutaneous tissue.

Quantitative microbiologic culture data from multiple organs were obtained 24 hours after infection in one group of knockout and of control mice. No statistically significant difference in the clearance of bacteria was detected (p>0.05) between the Ich-3 mutant mice and the wild types. Thus, lung injury was reduced in the presence of increased numbers of neutrophils, while the clearance of bacteria was unaltered.

These observations suggested that: 1) the failure of infiltrating neutrophils to degranulate and, possibly, to die was related to the absence of lung injury and 2) that the profile of cytokines and other mediators in the lungs might be informative with regard to manipulations potentially protective to the lungs in the setting of burns, major trauma, infection and sepsis. Data supports the hypothesis that the lack of lung injury is due to the avoidance of degranulation of infiltrating neutrophils in the burn/sepsis model. Apoptosis of neutrophils appears to be, however, roughly equivalent in knockout and wild-type mice following thermal injury or bacterial infection.

Example 17

Reduction of Mortality Due to Burn Injury and Sepsis in Normal Animals

Under conditions of bacteremia, sepsis and following thermal injury (10% body surface area burn) Ich-3 mutant nice are relatively resistant to development of pulmonary injury. Wild-type animals routinely (100%) develop pulmonary hemorrhage, pulmonary edema, and pulmonary inflammation following Pseudomonas bacteremia. The defect in the Ich-3 mutant mouse appears to block this result.

Control wild-type mice are treated with a compound that inhibits a pathway of apoptosis to mimic the genetic defect of the knockout mice. In this way one protects the lung against injury in common medical conditions. These injuries include but are not limited to sepsis due to bacteria and fungi, burn, major trauma, drug toxicity and other forms of systemic injury including viral infection, parasitemia, endocarditis, brain injury, pulmonary emboli all of which are associated with a syndrome knows as Adult Respiratory Distress Syndrome (ARDS). This is a debilitating and potentially fatal disorder of pulmonary inflammation and injury with fibrosis and results in prolonged hospitalization for mechanical ventilation, frequent superinfection and is often associated with patient death.

The apoptotic pathway involving ICH-3 is inhibited either prior to induction or during injury. The compounds to inhibit ICH-3 may be chosen from the group including but not limited to, peptide inhibitors such as YVAD-cmk, Ac-DEVD-CHO, cysteine protease inhibitors or serine protease inhibitors such as trans-epoxy succininyl-L-leucylamido-(4-guanidino) butane (E64) and leupeptin, calpain inhibitors I and II.

The treated mice and non-treated control mice are then injured as above (See Example 16). Alternatively the mice are injured by routine methods known in the art for producing major trauma. The injured mice are then monitored for the sequelae of injury, which includes but is not limited to signs of bacterial infection, endotoxemia and lethality at least twice daily. Additional sequelae of injury or infection can be readily found in the art, such as for example in Robbins S. L. et al., (*Basic Pathology*, 1987, W.B. Saunder Co.). Changes in the sequelae as recognized by those of skill in the art reflect an altered susceptibility to the injury being examined.

The systemic release of cytokines after toxin challenge is determined by ELISA kits for murine IL-α, IL1-β, IL6, IL10, IL8 (Endogen, Cambridge, Mass.). Animals ar sacrificed amd/or blood samples obtained at time point up to 7 days following the injury. Tissues are analyzed as described in Example 16.

All references mentioned herein are incorporated by reference in the disclosure. Having now fully described the invention by way of illustration and example for purposes of clarity and understanding, it will be apparent to those of ordinary skill in the art that certain changes and modification may be made in the disclosed embodiments and such modifications are intended to be within the scope of the present invention. As examples, the preferred embodiments constitute only one form of carrying out the claimed invention.

What is claimed is:

1. A method for stimulating synthesis of Ich-3 (Caspase-11) gene products in a cell comprising contacting said cell with stimulatory amounts of lipopolysaccharide (LPS) and detecting said Ich-3 gene products.

2. A method for modulating programmed cell death (apoptosis) in a cell comprising:

a) transfecting a cell with the ICH-3 (caspase-11) gene;

b) expressing the ICH-3 protein in said cell; and c) inducing apoptosis in said cell.

3. A method for modulating programmed cell death (apoptosis) in a cell comprising:

a) transfecting a cell with the ICH-3 (caspase-11) gene;

b) expressing the ICH-3 protein in said cell in the presence of ICE; and c) inducing apoptosis in said cell.

4. The method of claim 2 wherein said ICH-3 gene is operably linked to a CMV promoter.

5. The method of claim 3 wherein said ICH-3 gene is operably linked to a CMV promoter.

6. The method of claim 2 wherein said cell is a mammalian cell.

7. The method of claim 3 wherein said cell is a mammalian cell.

8. The method of claim 1, wherein said cell is a mammalian cell.

9. The method of claim 2 wherein said ICH-3 gene has the sequence found in FIGS. 1A–1B (SEQ ID NO:1).

10. The method of claim 3 wherein said ICH-3 gene has the sequence found in FIGS. 1A–1B (SEQ ID NO:1).

11. The method of claim 2 wherein said ICH-3 gene encodes the amino acid sequence found in FIGS. 1A–1B (SEQ ID NO:2).

12. The method of claim 2 wherein said ICH-3 gene encodes the amino acid sequence found in FIGS. 1A–1B (SEQ ID NO:2).

\* \* \* \* \*